(12) United States Patent
Webler et al.

(10) Patent No.: US 8,303,505 B2
(45) Date of Patent: Nov. 6, 2012

(54) METHODS AND APPARATUSES FOR IMAGE GUIDED MEDICAL PROCEDURES

(75) Inventors: William E. Webler, Escondido, CA (US); Mina Chow, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 2030 days.

(21) Appl. No.: 11/293,559

(22) Filed: Dec. 2, 2005

(65) Prior Publication Data

US 2007/0167801 A1   Jul. 19, 2007

(51) Int. Cl.
  *A61B 8/00*   (2006.01)
(52) U.S. Cl. .................. 600/447; 600/437; 600/459
(58) Field of Classification Search ........... 600/437–467
  See application file for complete search history.

(56) References Cited

U.S. PATENT DOCUMENTS

| | | |
|---|---|---|
| 3,585,391 A | 6/1971 | Siedband |
| 4,249,539 A | 2/1981 | Vilkomerson et al. |
| 4,401,124 A | 8/1983 | Guess et al. |
| 4,596,145 A | 6/1986 | Smith et al. |
| 4,694,434 A | 9/1987 | von Ramm et al. |
| 4,697,595 A | 10/1987 | Breyer et al. |
| 4,849,692 A | 7/1989 | Blood |
| 4,869,259 A | 9/1989 | Elkins |
| 4,876,509 A | 10/1989 | Perlmutter |
| 4,905,698 A | 3/1990 | Strohl, Jr. et al. |
| 4,980,905 A | 12/1990 | Meccariello |
| 5,042,486 A | 8/1991 | Pfeiler et al. |
| 5,186,174 A | 2/1993 | Schlondroff et al. |
| 5,201,314 A | 4/1993 | Bosley et al. |
| 5,211,165 A | 5/1993 | Dumoulin et al. |
| 5,230,623 A | 7/1993 | Guthrie et al. |
| 5,259,837 A | 11/1993 | Van Wormer |
| 5,289,831 A | 3/1994 | Bosley |
| 5,343,865 A | 9/1994 | Gardineer et al. |

(Continued)

FOREIGN PATENT DOCUMENTS

WO   WO-9729682   8/1997

(Continued)

OTHER PUBLICATIONS

Abbott Cardiovascular Systems, International search report and written opinion dated Jul. 31, 2007 for PCT/US2006/044508.

(Continued)

*Primary Examiner* — Sanjay Cattungal
(74) *Attorney, Agent, or Firm* — Angela M. Augustus; Blakely Sokoloff Taylor & Zafman LLP

(57) ABSTRACT

Methods and apparatuses for the image guidance and documentation of medical procedures. One embodiment includes combining small field of view images into a recorded image of with a large field of view and aligning the small field of view real time image with the recorded image through correlation of imaging data. A location and orientation determination system may be used to track the imaging system and provide a starting set of image alignment parameters and/or provide change updates to a set of image alignment parameters, which is then further improved through correlating imaging data. The recorded image may be selected according to real time measurement of a cardiac parameter during an image guided cardiac procedure. Image manipulations planned based on the recorded image can be stored and applied to the real time information. The position of the medical device may be determined and recorded through manipulating a cursor in a 3-D image space shown in two non-parallel views.

28 Claims, 21 Drawing Sheets

U.S. PATENT DOCUMENTS

| | | | |
|---|---|---|---|
| 5,368,037 A | 11/1994 | Eberle et al. |
| 5,377,678 A | 1/1995 | Dumoulin et al. |
| 5,381,791 A | 1/1995 | Quian |
| 5,389,101 A | 2/1995 | Heilbrun et al. |
| 5,391,199 A | 2/1995 | Ben-Haim |
| 5,424,637 A | 6/1995 | Oudyn et al. |
| 5,425,382 A | 6/1995 | Golden et al. |
| 5,445,150 A | 8/1995 | Dumoulin |
| 5,546,807 A | 8/1996 | Oxaal et al. |
| 5,603,318 A | 2/1997 | Heilbrun et al. |
| 5,647,360 A | 7/1997 | Bani-Hashemi et al. |
| 5,655,535 A | 8/1997 | Freimal et al. |
| 5,662,113 A | 9/1997 | Liu |
| 5,690,106 A | 11/1997 | Bani-Hashemi et al. |
| 5,738,096 A | 4/1998 | Ben-Haim |
| 5,765,561 A | 6/1998 | Chen et al. |
| 5,766,135 A | 6/1998 | Terwilliger |
| 5,767,669 A | 6/1998 | Hansen et al. |
| 5,769,795 A | 6/1998 | Terwilliger |
| 5,769,843 A | 6/1998 | Abela et al. |
| 5,776,062 A | 7/1998 | Nields |
| 5,782,760 A | 7/1998 | Schaer |
| 5,782,763 A | 7/1998 | Bianco et al. |
| 5,797,849 A | 8/1998 | Vesely et al. |
| 5,820,554 A | 10/1998 | Davis et al. |
| 5,833,608 A | 11/1998 | Acker |
| 5,871,445 A | 2/1999 | Bucholz |
| 5,913,820 A | 6/1999 | Bladen et al. |
| 5,921,933 A | 7/1999 | Sarkis et al. |
| 5,983,126 A | 11/1999 | Wittkampf |
| 5,999,662 A * | 12/1999 | Burt et al. | 382/284 |
| 6,004,269 A | 12/1999 | Crowley et al. |
| 6,004,270 A | 12/1999 | Urbano et al. |
| 6,016,439 A | 1/2000 | Acker |
| 6,018,676 A | 1/2000 | Davis et al. |
| 6,019,724 A | 2/2000 | Gronningsaeter et al. |
| 6,019,725 A | 2/2000 | Vesely et al. |
| 6,057,681 A | 5/2000 | Kipp et al. |
| 6,073,043 A | 6/2000 | Schneider |
| 6,095,976 A | 8/2000 | Nachtomy et al. |
| 6,104,944 A | 8/2000 | Martinelli |
| 6,106,473 A | 8/2000 | Violante et al. |
| 6,112,111 A | 8/2000 | Glantz |
| 6,119,033 A | 9/2000 | Spigelman et al. |
| 6,129,670 A | 10/2000 | Burdette et al. |
| 6,149,592 A | 11/2000 | Yanof et al. |
| 6,154,024 A | 11/2000 | Lewandowski et al. |
| 6,165,164 A | 12/2000 | Hill et al. |
| 6,167,296 A * | 12/2000 | Shahidi | 600/427 |
| 6,190,353 B1 | 2/2001 | Makower et al. |
| 6,216,027 B1 | 4/2001 | Willis et al. |
| 6,226,542 B1 | 5/2001 | Reisfeld |
| 6,226,546 B1 | 5/2001 | Evans |
| 6,233,476 B1 | 5/2001 | Strommer et al. |
| 6,241,675 B1 | 6/2001 | Smith et al. |
| 6,246,231 B1 | 6/2001 | Ashe |
| 6,246,898 B1 | 6/2001 | Vesely |
| 6,261,247 B1 | 7/2001 | Ishikawa et al. |
| 6,266,453 B1 | 7/2001 | Hibbard et al. |
| 6,275,724 B1 | 8/2001 | Dickinson et al. |
| 6,276,211 B1 | 8/2001 | Smith |
| 6,283,947 B1 | 9/2001 | Mirzaee |
| 6,283,951 B1 | 9/2001 | Flaherty et al. |
| 6,285,898 B1 | 9/2001 | Ben-Haim |
| 6,299,579 B1 | 10/2001 | Peterson et al. |
| 6,312,381 B1 | 11/2001 | Knell et al. |
| 6,314,310 B1 | 11/2001 | Ben-Haim et al. |
| 6,317,029 B1 | 11/2001 | Fleeter |
| 6,341,231 B1 | 1/2002 | Ferre et al. |
| 6,352,507 B1 | 3/2002 | Torp et al. |
| 6,352,511 B1 | 3/2002 | Hossack et al. |
| 6,358,247 B1 | 3/2002 | Altman et al. |
| 6,360,027 B1 | 3/2002 | Hossack et al. |
| 6,366,798 B2 | 4/2002 | Green |
| 6,370,417 B1 | 4/2002 | Horbaschek et al. |
| 6,381,485 B1 | 4/2002 | Hunter et al. |
| 6,389,310 B1 | 5/2002 | Demonceau et al. |
| 6,400,981 B1 | 6/2002 | Govari |
| 6,402,762 B2 | 6/2002 | Hunter et al. |
| 6,405,072 B1 | 6/2002 | Cosman |
| 6,409,671 B1 | 6/2002 | Ericksen et al. |
| 6,416,477 B1 * | 7/2002 | Jago | 600/447 |
| 6,424,410 B1 | 7/2002 | Pelosi |
| 6,424,860 B1 | 7/2002 | Karlsson et al. |
| 6,427,079 B1 | 7/2002 | Schneider et al. |
| 6,434,265 B1 | 8/2002 | Xiong et al. |
| 6,442,289 B1 | 8/2002 | Olsson et al. |
| 6,445,943 B1 | 9/2002 | Ferre et al. |
| 6,484,049 B1 | 11/2002 | Seeley et al. |
| 6,490,475 B1 | 12/2002 | Seeley et al. |
| 6,490,476 B1 | 12/2002 | Townsend et al. |
| 6,491,702 B2 | 12/2002 | Heilbrun et al. |
| 6,517,485 B2 | 2/2003 | Torp et al. |
| 6,529,617 B1 | 3/2003 | Prokoski |
| 6,529,758 B2 * | 3/2003 | Shahidi | 600/407 |
| 6,532,036 B1 | 3/2003 | Peleg et al. |
| 6,541,966 B1 | 4/2003 | Keene |
| 6,544,185 B2 | 4/2003 | Montegrande |
| 6,545,678 B1 | 4/2003 | Ohazama |
| 6,554,801 B1 | 4/2003 | Steward et al. |
| 6,561,979 B1 | 5/2003 | Wood et al. |
| 6,572,593 B1 | 6/2003 | Daum |
| 6,577,904 B1 | 6/2003 | Zhang et al. |
| 6,591,130 B2 * | 7/2003 | Shahidi | 600/424 |
| 6,592,520 B1 | 7/2003 | Peszynski et al. |
| 6,595,921 B1 | 7/2003 | Urbano et al. |
| 6,605,095 B2 | 8/2003 | Grossman |
| 6,610,016 B1 | 8/2003 | Violante et al. |
| 6,612,992 B1 | 9/2003 | Hossack et al. |
| 6,628,845 B1 | 9/2003 | Stone et al. |
| 6,631,284 B2 | 10/2003 | Nutt et al. |
| 6,645,195 B1 | 11/2003 | Bhat et al. |
| 6,650,927 B1 | 11/2003 | Keidar |
| 6,662,036 B2 | 12/2003 | Cosman |
| 6,669,641 B2 | 12/2003 | Poland et al. |
| 6,671,538 B1 | 12/2003 | Ehnholm et al. |
| 6,675,032 B2 | 1/2004 | Chen et al. |
| 6,675,037 B1 | 1/2004 | Tsekos |
| 6,676,599 B2 | 1/2004 | Torp et al. |
| 6,689,043 B1 | 2/2004 | McIntire et al. |
| 6,689,065 B2 | 2/2004 | Aksnes et al. |
| 6,692,466 B1 | 2/2004 | Chow et al. |
| 6,716,166 B2 | 4/2004 | Govari |
| 6,741,730 B2 | 5/2004 | Rahn et al. |
| 6,744,933 B2 | 6/2004 | Lai et al. |
| 6,749,554 B1 | 6/2004 | Snow et al. |
| 6,751,492 B2 | 6/2004 | Ben-Haim |
| 6,754,520 B2 | 6/2004 | DeSilets et al. |
| 6,755,787 B2 * | 6/2004 | Hossack et al. | 600/447 |
| 6,755,789 B2 | 6/2004 | Stringer et al. |
| 6,793,647 B1 | 9/2004 | Cryer |
| 6,819,785 B1 | 11/2004 | Vining et al. |
| 6,855,124 B1 | 2/2005 | Gonzalez et al. |
| 6,856,826 B2 | 2/2005 | Seeley et al. |
| 6,856,827 B2 | 2/2005 | Seeley et al. |
| 6,863,655 B2 | 3/2005 | Bjaerum et al. |
| 6,915,003 B2 | 7/2005 | Oosawa |
| 6,923,768 B2 | 8/2005 | Camus et al. |
| 6,968,224 B2 | 11/2005 | Kessman et al. |
| 7,666,140 B2 * | 2/2010 | Kato | 600/443 |
| 7,844,320 B2 * | 11/2010 | Shahidi | 600/424 |
| 2001/0039421 A1 | 11/2001 | Heilbrun et al. |
| 2001/0041888 A1 | 11/2001 | Goldman |
| 2002/0049375 A1 | 4/2002 | Strommer et al. |
| 2002/0151796 A1 | 10/2002 | Koulik |
| 2003/0065260 A1 | 4/2003 | Cheng et al. |
| 2003/0109823 A1 | 6/2003 | Hobot et al. |
| 2003/0135115 A1 | 7/2003 | Burdette |
| 2003/0231789 A1 | 12/2003 | Willis et al. |
| 2004/0006266 A1 * | 1/2004 | Ustuner et al. | 600/407 |
| 2004/0059217 A1 | 3/2004 | Kessman et al. |
| 2004/0066398 A1 | 4/2004 | Dolimier et al. |
| 2004/0106934 A1 | 6/2004 | Grossman |
| 2004/0193053 A1 * | 9/2004 | Kato | 600/440 |
| 2005/0070844 A1 | 3/2005 | Chow et al. |
| 2005/0080333 A1 | 4/2005 | Piron et al. |

| | | |
|---|---|---|
| 2005/0107688 A1 | 5/2005 | Strommer |
| 2005/0182316 A1 | 8/2005 | Burdette et al. |
| 2009/0275830 A1* | 11/2009 | Falco et al. .................. 600/437 |

FOREIGN PATENT DOCUMENTS

| | | |
|---|---|---|
| WO | WO-2004030740 | 4/2004 |

OTHER PUBLICATIONS

Abbott Cardiovascular Systems, International preliminary report on patentability dated Jun. 12, 2008 for PCT/US2006/044508.

Ablitt, N., et al., "Predictive Cardiac Motion Modeling and Correction With Partial Least Squares Regression", IEEE Transactions on Medical Imaging, vol. 23, No. 10, (Oct. 2004), 1315-1324.

Breen, M., et al., "Three Dimensional Correlation of MR Images to Muscle Tissue Response for Interventional MRI Thermal Ablation", Medical Imaging 2001: Visualization, Display, and Image-Guided Procedures, Seong Ki Mun, Editor, Proceedings of SPIE vol. 4319, (2001), 211-220.

Cash, D. M., et al., "Incorporation of a laser range scanner into image-guided liver surgery: Surface acquisition, registration, and tracking", Med. Phys., 30 (7), (Jul. 2003), 1671-82.

Castro, O., et al., "Pulmonary hypertension in sickle cell disease: cardiac catherization results and survival", The American Society of Hematology; Clinical Observations, Interventions and Therapeutic Trials, Blood—vol. 101, No. 4, (Feb. 15, 2003), 1257-1261.

Caversaccio, M., et al., "The "Bernese" Frameless Optical Computer Aided Surgery System", Computer Aided Surgery, vol. 4, (1999), 328-334.

Chung, A. J., et al., "Extraction of visual features with eye tracking for saliency driven 2D/3D registration", Image and Vision Computing, vol. 23, Issue 11, (Oct. 1, 2005), 999-1008.

Dorr, L. D., et al., "Intraoperative monitoring for safety of bilateral total knee replacement", Clinical Orthopaedics and Related Research, No. 396, Lippincott Williams & Wilkins, Inc., (2002), 142-151.

Fuss, M., et al., "Daily ultrasound-based image-guided targeting for radiotherapy of upper abdominal malignancies", Int. J. Radiation Oncology Biol. Phys., vol. 59, No. 4, (2004), 1245-1256.

Gerber, B. L., et al., "Accuracy of contrast-enhanced magnetic resonance imaging in predicting improvement of regional myocardial function in patients after acute myocardial infarction", Circulation, Journal of the American Heart Association, 106, (Aug. 12, 2002), 1083-1089.

Glogar, H. D., et al., "Non-fluoroscopic catheter-based endocardial mapping and mapping-guided percutaneous transmyocardial revascularization", J Kardiol, 8(12), (2001), 503-507.

Gobbi, D. G., et al., "Correlation of pre-operative MRI and intra-operative 3D ultrasound to measure brain tissue shift", Visualization, Display, and Image-Guided Procedures, Seong Ki Mun, Editor, Proceedings of SPIE vol. 4319, (2001), 264-271.

Hilfiker, P. R., et al., "Multislice spiral computed tomography of subacute myocardial infarction", Circulation; Journal of the American Heart Association, 104, (2001), 1083.

Maintz, J. B., et al., "A survey of medical image registration", Medical Image Analysis, vol. 2, No. 1, (1998), 1-36.

Miga, M. I., et al., "Intraoperative Registration of the Liver for Image-Guided Surgery Using Laser Range Scanning and Deformable Models", Medical Imaging 2003: Visualization, Image-Guided Procedures and Display, Proceedings of SPIE vol. 5029, (2003), 350-359.

Mochizuki, T., "Demonstration of acute myocardial infarction by subsecond spiral computed tomography: early defect and delayed enhancement", Circulation; Journal of the American Heart Association, 99, (1999), 2058-2059.

Netsch, T., et al., "Towards real-time multi-modality 3-D medical image registration", ICCV 2001. Proceedings. Eighth IEEE International Conference on Computer Vision, vol. 1, (2001), 718-725.

Ourselin, S., et al., "Block matching: a general framework to improve robustness of rigid registration of medical images", Medical image computing and computer-assisted intervention—MICCAI, (2000), 557-566.

Perin, E. C., et al., "Assessing myocardial viability and infarct transmurality with left ventricular electromechanical mapping in patients with stable coronary artery disease: validation by delayed-enhancement magnetic resonance imaging", Circulation; Journal of the American Heart Association, 106, (Aug. 5, 2002), 957-961.

Peters, Terry M., "Image-guided surgery: from x-rays to virtual reality", Computer Methods in Biomechanics and Biomedical Engineering, vol. 4, No. 1, (2000), 27-57.

Rosen, J. M., et al., "Evolution of virtual reality: From planning to performing surgery", IEEE Engineering in Medicine and Biology, vol. 2, No. 2, (Mar./Apr. 1996), 16-22.

Solomon, S. B., et al., "Three-dimensional CT-guided bronchoscopy with a real-time electromagnetic position sensor: a comparison of two image registration methods", Chest: Official publication of the American College of Chest Physicians, 118(6), (Dec. 2000), 1783-1787.

Sra, J., et al., "Feasibility and validation of registration of three-dimensional left atrial models derived from computed tomography with a noncontract cardiac mapping system", Heart Rhythm Society, 2, (2005), 55-63.

Swan, H. J., "What is the role of invasive monitoring procedures in the management of the critically ill", Cardiovasc Clin, vol. 8, No. 1, (1977), 103-111.

Tremblay, M., et al., "Retrospective coregistration of functional magnetic resonance imaging data using external monitoring", Magnetic Resonance in Medicine, 53, (2005), 141-149.

Van Den Bosch, A. E., et al., "Realtime three-dimensional echocardiography—a perspective", Business Briefing: European Cardiology, (2005), 1-30.

Vander, A. J., et al., "Sensory Physiology", Human Physiology: The Mechanisms of Body Function, Ninth Edition, Chapter 7; McGraw Hill, (2004), 237-239.

Weeks, K. R., et al., "Bedside hemodynamic monitoring—Its value in the diagnosis of tamponade complicating cardiac surgery", J. Thorac Cardiovasc Surg, vol. 71, No. 2, (1976), 250-252.

* cited by examiner

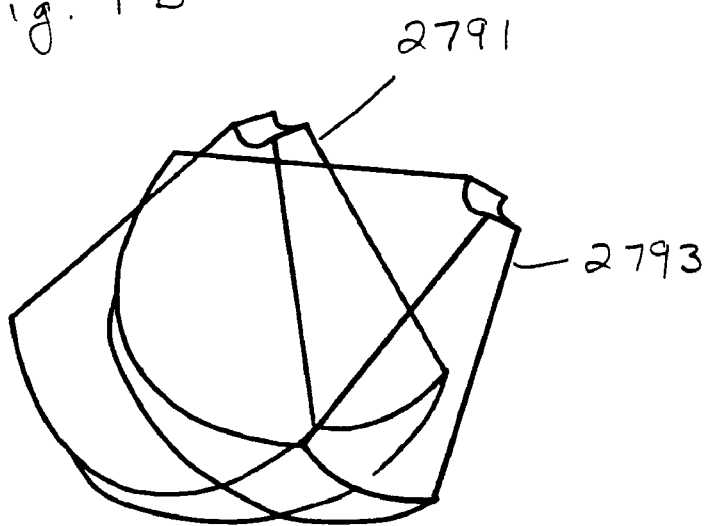

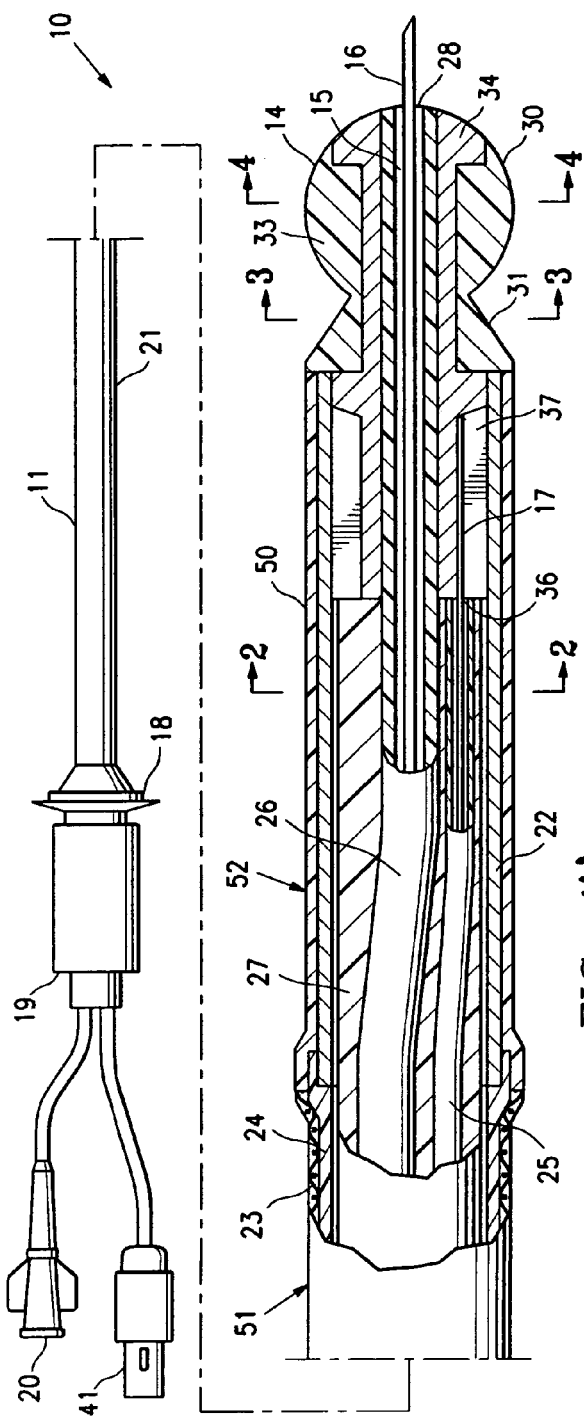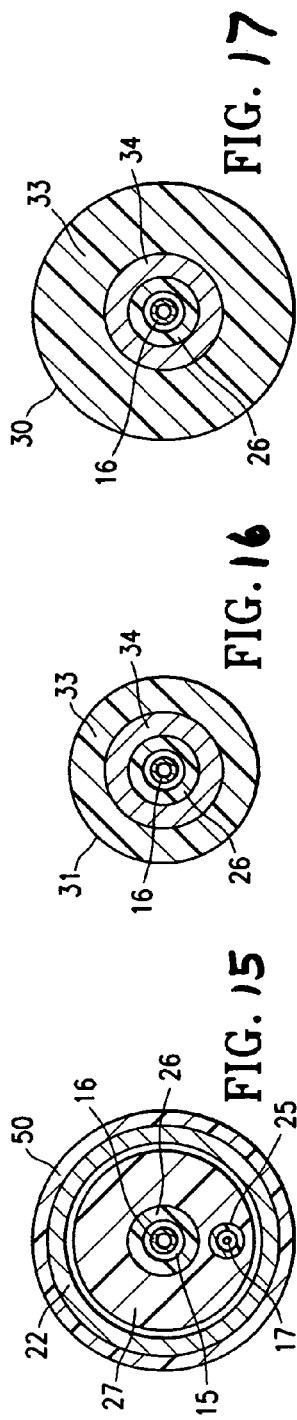
FIG. 14
FIG. 15
FIG. 16
FIG. 17

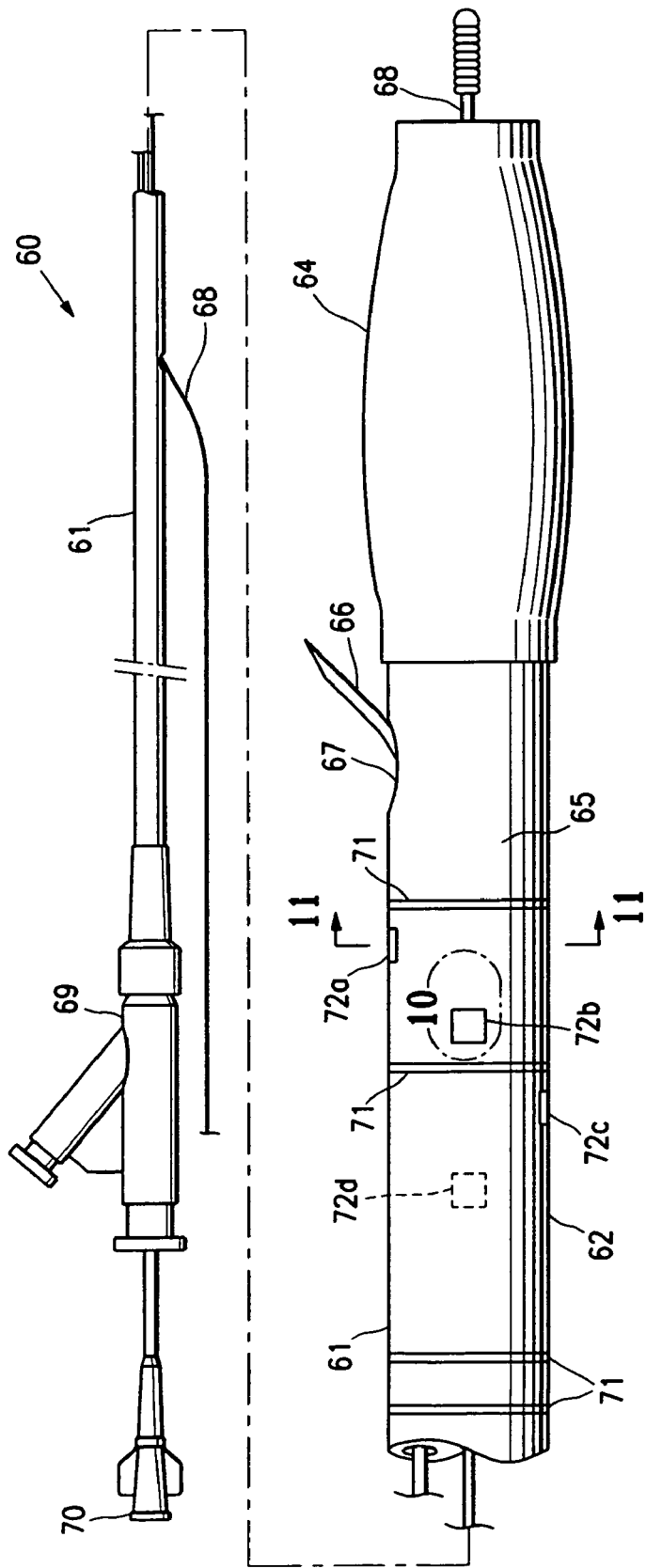
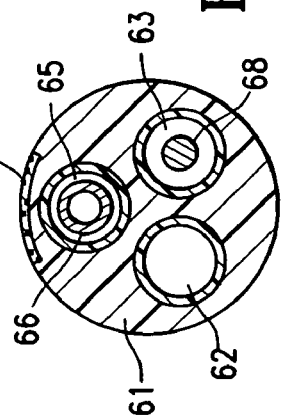
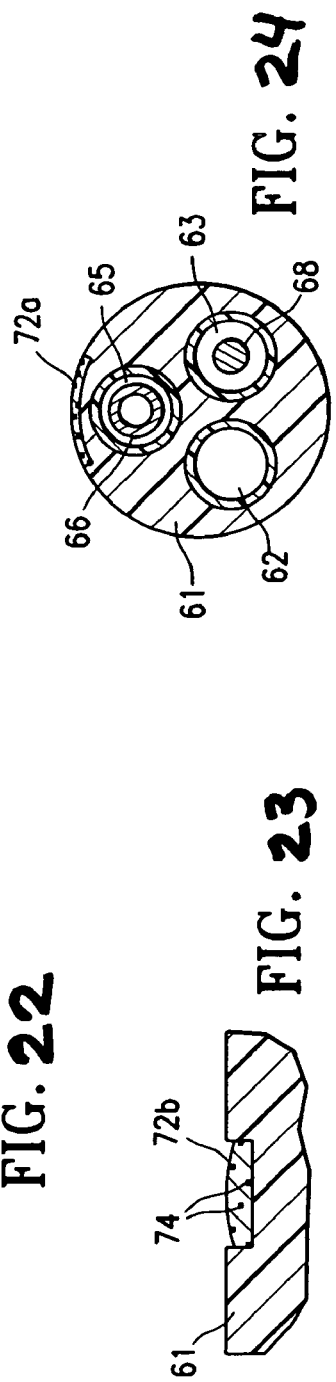
FIG. 22
FIG. 23
FIG. 24

METHODS AND APPARATUSES FOR IMAGE GUIDED MEDICAL PROCEDURES

The present patent application relates to co-pending U.S. patent application Ser. No. 10/390,065, filed Mar. 14, 2003, entitled "Method and Apparatus for Image Guided Position Tracking During Percutaneous Procedures" by inventor William E. Webler, which is hereby incorporated herein by reference.

TECHNOLOGY FIELD

Some embodiments of the present inventions relate to the spatial alignment (which may include scaling) of a real time image/data and a recorded image/data to display a limited field of view real time image in an anatomically correct alignment with the larger field of view recorded image to show the anatomic relationship of the limited field of view image to the overall anatomy image and/or to compensate for undetected motion of the anatomy in the real time image relative to the anatomy in the recorded image. Some embodiments of the present invention relate to imaging and/or tracking of medical instruments relative to the anatomy, and more particularly to the guidance of medical instruments and the documentation of diagnostic and therapeutic information gathered or applied by medical instruments during percutaneous procedures, such as cardiac therapies, using imaging systems.

BACKGROUND

Computer-aided Tomography (CT) (such as X-ray, Positron Emission Tomography (PET), etc.) and Magnetic Resonance (MR) based imaging systems commonly control and sense the location (and/or orientation) of the patient and/or the image sensing/producing equipment to produce a recorded image of a patient's anatomy that is assembled from multiple image data collections from different portions of the patient's anatomy. The patient is typically instructed to hold their breath and remain motionless during the imaging procedure in order to keep anatomy positions as constant as possible in each image data collection and thus, create as continuous and anatomically correct a recorded image as possible out of the assembled multiple image data collections.

When such systems are used in a real time mode, the time required for image data collection and/or image data processing and/or the designed field of view of the image sensing/producing equipment limits the portion of the anatomy that can be displayed in the rapidly updated manner that is referred to as "real time".

Attempting to widen the field of view typically introduces noticeable and annoying time delays between the displayed image and the actual condition of the anatomy and/or requires impractically rapid patient and/or equipment position changes. When attempting to guide a medical device in the anatomy and record locations in the anatomy, real time imaging is desired and these problems become particularly bothersome.

The real time image's limited field of view makes the anatomical context of the real time image or a diagnosis based on tissue image properties and/or their relationship to the adjacent anatomy difficult to interpret. Thus, the location of the medical device relative to the adjacent anatomy or anatomy landmarks as shown in the real time image can be difficult to determine or time consuming to determine.

Additionally, a tissue diagnosis based on the real time image can be difficult to determine or time consuming to determine. Often one must take the additional time to create and examine a recorded wider field of view image to determine a tissue diagnosis or device location relative to the anatomy. Medical operations employing medical devices, especially percutaneous catheter-based procedures, are often best or necessary to perform when the patient is conscious; and these procedures are much longer than the time required to make a recorded image with a wide field of view of the anatomy. It is not very practical to expect the patient to hold their breath in a repeatable manner on command or to be able to remain perfectly still on the positioning table during the medical operation and real time imaging.

While locations recorded in the real time image reference frame will be correct relative to the anatomy in that particular very transitory real time image, the anatomy will move between real time images due to the patient's breathing and/or inability to remain motionless for long periods of time. Therefore, the distances between locations recorded in real time image reference frame and between recorded locations and anatomical structures in real time image reference frame will be uncertain or in error by the amount (and timing) of this uncontrolled patient motion.

This uncertainty or error is undesirable in many situations, such as when attempting to control the spacing of a therapy applied by a medical device using imaging. These problems are greatly accentuated in conventional ultrasonic based imaging systems, because the field of view of ultrasonic systems is typically much smaller than CT and MR based imaging systems. Additionally, the image sensing/producing equipment (the imaging probe) of conventional ultrasonic systems is manually positioned and its location and/or orientation is not controlled or sensed by the imaging system.

There have been various developments in the medical imaging techniques and their applications. Maintz, et al. presented "A Survey of Medical Image Registration" in Medical Image Analysis, Vol. 2, No. 1, pp 1-36, 1998. Terry M. Peters presented "Review—Image-guided surgery: From X-rays to Virtual Reality" in Computer Methods in Biomechanics and Biomedical Engineering, Vol. 4, No. 1, pp. 27-57, 2000.

Friemel, et al. (U.S. Pat. No. 5,655,535) presented a method to obtain compounded field of view ultrasound image from correlated frames of ultrasound image data. Frames of sensed echo signals are processed to detect probe motion without the use of a dedicated position sensor or motion sensor. Correlating the frames is used to detect the motion of the ultrasound probe. Image registration is performed for correlated portions to compound a large ultrasound image.

Burt, et al. (U.S. Pat. No. 5,999,662) presented a method to automatically generating a mosaic from a plurality of input images. In one example of Burt, et al., a scene of interest is illustratively captured in four video frames. Additionally, a person is walking through the scene from left to right. The images of the scene are aligned and combined using batch sequencing to produce a mosaic containing background. The residuals represent object motion relative to the background, e.g., the person walking through the scene. The image alignment process automatically aligns one input image to another input image.

Hibbard, et al. (U.S. Pat. No. 6,266,453) presented a method for automated image fusion /alignment of 3-D images. In the method of Hibbard, et al., a GUI is used to simultaneously display two 3-D image data volumes. One of the 3-D image data volumes is held constant while the other may be scaled, rotated, and translated to align homologous anatomic features. Hibbard, et al. also suggest that the image can be aligned automatically through computation based on mutual information ("MI") maximization and the automated alignment, using MI maximization, may be performed before, after or instead of, manual alignment.

Jago (U.S. Pat. No. 6,416,477) also presented another method to produce spatially compounded panoramic ultrasound images.

Heilbrun, et al. (U.S. Patent Application Publication No. 2001/0039421) presented a method for photogrammetric surgical localization, in which the 3-D framework of the workspace can be aligned with the 3-D framework of any selected volume scan, such as MRI, CT, or PET, so that the instrument can be localized and guided to a chosen feature. To provide object recognition and location of medical instruments and the like in the image field, a digitized image pair made prior to the introduction of the instrument into the workspace is compared to an image pair made with the instrument in substantially complete view, and background subtraction-is used to remove static objects in the image field. After the image has been appropriately filtered to sharpen the image and enhance object edges, edge detection is performed for geometric recognition. Once the instrument is identified, its orientation and tip location are determined in terms of coordinates in the 3-D workspace.

Burdette, et al. (U.S. Patent Application Publication No. 2003/0135115) presented a method to determine the location of a biopsy needle within a target volume. In the method of Burdette, et al., images of the target volume is generated and spatially registered. A three-dimensional representation of the target volume is then generated from the spatially registered images. After the location of the biopsy needle in the three-dimensional target volume representation is determined, the determined biopsy needle location is correlated with the spatially registered images. For example, when the target volume representation is displayed graphically, the target volume representation also includes a graphical depiction of the determined biopsy needle location. The needle may stand out in bright contrast to the surrounding tissues in an ultrasound images, and as such, known pattern recognition techniques such as edge detection methods can be used to identify the needle's location in the ultrasound images. Because the images are spatially registered, the location of the biopsy needle relative to the coordinate system is determinable.

Burdette, et al. (U.S. Pat. No. 6,129,670) presented a system for developing a therapy plan for treatment of an organ of the patient. A translucent volume image of a portion of a patient's body, a separate translucent image of the patient organ and a translucent article image are superimposed to enable viewing of the article image simultaneously with the patient organ and a portion of the patient's body.

Gronningsaeter, et al. (U.S. Pat. No. 6,019,724) presented a method for ultrasound guidance during surgical, therapeutic or diagnostic procedures. One can correlate an in on-site ultrasound 3-D image with a 3-D data set from a previously acquired image data base and make these coordinate sets coincide with each other as well as coincide with the tool location coordinate system. In an example for open brain tumor surgery, Gronningsaeter, et al. suggest that the location of the tool can be detected in the overview image by temporal high pass filtering if the tool is continuously moving. One way to perform temporal high pass filtering is to subtract two 2-D or 3-D data sets to cancel stationary targets and highlight the moving tool. In another example, Gronningsaeter, et al. describe that after a physician marks the desired point for the radiation field center in the ultrasound image, the coordinates of this point are transferred to the coordinate system of the simulator and the direct feedback of target location will aid the placement of radiation fields and their relative angles to the patient.

Urbano, et al. (U.S. Pat. No. 6,004,270) presented an ultrasound system for contrast agent imaging and quantification in echocardiography using template image for image alignment. According to Urbano, et al., a stored template image and a real-time image are simultaneously displayed on an image display. The simultaneously displayed images have a visually perceptible effect when the real-time image becomes closely aligned with the template image at the same selected time period during the physiologic cycle. After alignment is achieved, a difference image is calculated, stored and displayed. The template image improves the alignment process of pre-contrast and post-contrast images, or pre-event/post-event difference images.

Yanof, et al. (U.S. Pat. No. 6,149,592) presented a method to electronically correlate a fluoroscopic image coordinate system and a volumetric image coordinate system and to display the volumetric image data (CT) together with at least a portion of the fluoroscopic images superimposed on the volumetric image data to show an image of said surgical instrument relative to said volumetric image data.

Hossack, et al. (U.S. Pat. No. 6,352,511) presented a medical diagnostic ultrasound system and method for post processing. According to Hossack, et al., for further enhancement of re-persistence, the recovered frames of ultrasound data are aligned or substantially aligned prior to re-persisting. The frames of ultrasound data are aligned as a function of a region of interest.

Nutt, et al. (U.S. Pat. No. 6,631,284) presented a method to combine PET and X-Ray CT tomography for acquiring CT and PET images sequentially in a single device. Nutt, et al. summarized some available techniques to co-register and align functional and anatomical images and their usages.

Seeley, et al. (U.S. Pat. No. 6,856,827) presented a fluoroscopic tracking and visualization system. In the system of Seeley, et al., one image in the display is derived from the fluoroscope at the time of surgery. A fixture is affixed to an imaging side of the fluoroscope for providing patterns of an of array markers that are imaged in each fluoroscope image. A tracking assembly having multiple tracking elements is used to determine positions of the fixture and the patient. One of the tracking elements is secured against motion with respect to the fixture so that determining a position of the tracking element determines a position of all the markers in a single measurement.

Perskey (PCT Publication No. WO 02/096261) presents a method to accurately register three-dimensional CT or MRI images taken prior to an operation and integrate the images with real-time tracking positional data of the patient's body part and instruments operating thereon.

Gobbi, et al. presented "Correlation of pre-operative MRI and intra-operative 3-D ultrasound to measure brain tissue shift", in K. K. Shung and M. F. Insana, editors, *Medical Imaging* 2000: *Ultrasonic Imaging and Signal Processing*, volume 3982 of *Proceedings of SPIE*, pages 77-84, 2000. In the system of Gobbi, et al., a set of infrared LEDs mounted on the ultrasound probe are used to track the location and orientation of the ultrasound probe so that the real time ultrasound images can be overlaid on the pre-operative MRI volume.

Piron, et al. (U.S. Patent Application Publication No. 2005/0080333) presented a hybrid imaging method to monitor medical device delivery and a patient support for use in the method. Particularly, MR imaging is used for the initial identification of tissue targets; and ultrasound imaging is then used to verify and monitor accurate needle positioning. The MR images and ultrasound images are co-registered based on measurements of fiducial markers obtained during the MR imaging procedure.

Keidar (U.S. Pat. No. 6,650,927) presented a method to render diagnostic imaging data on a three-dimensional map. The system of Keidar captures a three-dimensional (3-D) image of the structure including diagnostic information. A 3-D geometrical map of the structure is generated using a probe inserted into the structure. The image is registered with the map, such that each of a plurality of image points in the image is identified with a corresponding map point in the map. The map is displayed such that the diagnostic information associated with each of the image points is displayed at the corresponding map point. Typically, the system includes an ECG monitor to receive signals from one or more body surface electrodes, so as to provide an ECG synchronization signal.

Electrocardiogram (ECG, sometimes abbreviated as EKG) may be used for synchronization in collecting and/or combining data collected at the same or similar times relative to the cardiac cycle, usually based on the "QRS" complex or "R" wave of the ECG waveform. ECG looping of cardiac location specific data includes displaying collected ECG synchronized data/images sequentially through the ECG period, repeatedly in a continuous loop, such as image data and device location and/or orientation data (e.g., device portion position on or in contact with the heart).

ECG synchronization may include the detection and elimination of data from irregular or unusual ECG intervals or waveforms. For instance, modern MRI (Magnetic Resonance Imaging), Ultrasonic and CT (Computed Tomography) 3-D cardiac imaging systems incorporate these processes.

Cardiac catheter 3-D location systems, like the NOGA and CARTO systems, may incorporate these processes. Without ECG synchronization, the motion of the heart can cause very indistinct/low resolution cardiac images and varying device location information that can't be easily interpreted when images or location data or other data collected from different times in the cardiac cycle are combined. The NOGA and CARTO systems can display location data (and processed location data) recorded with ECG synchronization in synchronization with the patient's real-time ECG (synchronized ECG looping).

Some Electrophysiology (EP) navigation/ablation systems contain within them idealized or sample 3-D ECG synchronized images of the heart, which are displayed using synchronized ECG looping. At the same time, a multi-electrode device connected to the system is positioned in the patient's left ventricle (or other cardiac chamber) to record ECG waveforms, usually at 64 positions of known relative spacing. The ECG waveform data from the electrodes is processed to determine (compute) the de-polarization/re-polarization cycle of the adjacent tissues of the heart (the tissue electrical activity that produces the ECG and muscle contraction) and maps this data onto the synchronized ECG loop image data of the idealized or sample heart image, usually by color or pattern coding.

This provides a visual representation of the paths and patterns of the heart's electrical activation for diagnostic purposes (e.g., to identify abnormal cardiac tissue virtual locations that are self-activating or continuously activating each other in a loop and thus, disrupting the normal contraction pattern and/or contraction rate of the heart). This modified image is then recorded and displayed using synchronized ECG looping.

The multi-electrode device is removed from the chamber. When the ablation catheter connected to the system is inserted into the chamber, its tip and other electrode(s) sense ECG waveforms. The system computes at what location within the modified, idealized or sample heart image such a waveform would be produced based on the determined and recorded tissue activation pattern (de-polarization/re-polarization cycle) in the idealized or sample heart image and displays that position (usually as a colored ball or spot) within the idealized or sample heart image. Thus, the ablation catheter operator can guide the tip of the catheter to the damaged/malfunctioning tissue to destroy it and eliminate the aberrant electrical activation pattern.

Vesely, et al. (U.S. Pat. No. 5,797,849) presented a method for carrying out a medical procedure using a 3-D tracking and imaging system. In the system of Vesely, et al., the location of a surgical instrument, such as a catheter, is tracked and displayed relative to its immediate surroundings to improve a physician's ability to precisely position the surgical instrument. An imaging modality system is used to acquires 2-D, 3-D or 4-D image data sets from an imaging source, such as fluoroscopy, an MRI (magnetic resonance imaging), CT (computerized tomography of X-ray images) or 2-D or 3-D ultrasound device, to provide a "template" through or against which the shape, position and movement of instrument 1670 being tracked can be displayed. The template typically takes the form of an image of the environment surrounding the instrument (e.g., a bodily structure). If multiple (3-D) volumes are acquired at different time intervals, a 4-D image is obtained (e.g., 3-D image changing over time). Other methods and systems are also described in U.S. Pat. Nos. 5,343,865; 4,697,595; 4,596,145; 4,249,539; 4,694,434; 5,546,807; 6,241,675; 6,276,211; and 6,545,678.

Based on the 3-D coordinates of the individual transducers mounted to the instrument body, a 3-D image that would represent the position, size and shape of the instrument is constructed. The 3-D image of the instrument is placed in the correct spatial relationship with the underlying images showing the environment surrounding the instrument. For moving image sets, such as 2-D video loops, or 3-D ultrasound loops of the heart, the motion of the image data sets need to be output at a rate that continually matches that of the patient heart beat. To synchronize "video loops" with a patient's heart beat, a raw ECG signal is input into the processing computer.

One difficulty with ultrasound imaging has been visualization anomalies, including artifacts and overly bright images, in the ultrasonic images of catheters. Such artifacts can provide a misleading and inaccurate impression of the shape and/or location of the catheter within the patient. Additionally, catheter elements can appear so bright and large on the ultrasonic image (called "blooming") due to their highly reflective nature relative to the anatomy, especially at the gain settings typically used to image the anatomy, that the image of the adjacent anatomy is obscured by the catheter image. For example, metallic portions of catheters can produce strong/high amplitude echoes (bright images), with a pyramid artifact (i.e., a pyramid shape of reverberation ("ringing") images trailing off in the viewing direction). Similarly, most thermoplastic catheter shafts produce strong/high amplitude direct echoes (bright images). If the gain settings of the ultrasonic imaging system are reduced to improve the image of the catheter (reduce its image and artifact brightness), the image of the anatomy fades significantly to the point of being less visible or not visible at all. Therefore, it would be a significant advance to provide a catheter with improved imaging characteristics by two-dimensional and three-dimensional ultrasonic imaging systems for enhancing the diagnosis and guidance of treatments in the body.

SUMMARY OF THE DESCRIPTION

Some embodiments of the present inventions are summarized in this section.

One embodiment of the present invention includes the spatial alignment of a real time image (e.g., a 3-D image data set) with a recorded image (e.g., another previously recorded 3-D image data set) to display a limited field of view real time image in an anatomically correct alignment with a larger field of view in the recorded image. Spatial alignment of images may include determining one or more parameters of: scale, rotation and translation to match one image coordinate system with another so that the corresponding points captured in the images coincide (approximately or exactly) with each other when the images are superimposed on each other using these parameters. In one embodiment, the spatial alignment of the real time image and the recorded image is performed (or improved) through image correlation to guide and document treatments by a medical device. In one embodiment, image correlation is performed through matching corresponding similar or same information embedded in the images, such as through optimizing mathematically a correlation function, a mutual information function, or others using the pixel data in the images.

In one embodiment, the recorded image and the real time image show at least a portion of a moving organ (such as a heart); and one or more real time hemodynamic or physiologic parameters (such as blood pressure, heart rate, ECG, respiration rate, respiration cycle, hydration state, blood volume, and sedation state) are used to select the corresponding frames of recorded images and real time images so that the images are also hemodynamically and/or physiologically aligned. In one embodiment the images are displayed using synchronized looping derived from the waveform of a physiologic parameter.

In one embodiment, the real time image or an image created at least in part from the real time image data shows a medical device that is not in the recorded image, although in alternative embodiments, the medical device may be in the recorded image. A graphical user interface is presented to show at least two non-parallel, preferably orthogonal, 2-D views of the 3-D image data to allow a cursor which is capable of being positioned in 3-D space on an identified target, such as a tip portion of the medical device, a location of treatment, etc. to be positioned on each of the 2-D views. The position of the cursor can then be identified and recorded in relation with the objects shown in the recorded image or an image created at least in part from the recorded image data. Alternatively, a medical device shown in the real time image but not in the recorded image can be automatically recognized through pattern recognition (e.g., through subtracting, after spatial alignment, the real time image and recorded image from each other to remove background objects and perform edge detection to detect the outline of the medical device, such as a needle, a catheter, etc.).

In one embodiment, the ultrasound probe's location and orientation are tracked to correlate the image coordinate systems of the recorded images and real time images. Such a correlation may be based on the location and orientation tracking system, which is used as a starting point in optimizing image correlation to find the improved spatial alignment of the real time image with the recorded image. In one embodiment, the ultrasound probe's position relative to the anatomy of the patient is manually inputted to the system to provide a starting point. Alternatively or in addition, other image registration methods, such as manual alignment through a graphical user interface, can also be used to provide the starting point of image correlation.

In one embodiment, a sequence of manipulations on the recorded image, such as cropping, zooming, copying, rotating, translating, scaling, etc., are recorded. After the alignment of the real time image and the recorded image, the recorded sequence of manipulations is applied to the real time image (or a combination of the real time image and the recorded image, or the recorded image with superimposed real time information, such as a graphical representation of the real time position of the medical device). In one embodiment, multiple sequences of manipulations may be recorded as templates based on the recorded image. During the medical operation, one of the sequences is selected and applied. Further, in one embodiment, the operator may adjust parameters for a sequence, interrupt and/or add to the sequence and provide further customized input to perform the operation. Thus, the operator may plan 3-D image data viewing operations using the recorded image data set and apply the viewing operations to the real time information such that the real time image is aligned with the recorded image in the resulting display(s). The sequence of recorded manipulation may represent a single resulting view, multiple views, different types of views (e.g. see-through view, surface view), a view, or views at a particular time or time interval in a physiologic cycle (e.g., the cardiac cycle) or a series of views of the 3-D image data (e.g., as a slide show or animation).

One embodiment of the present invention includes aligning smaller field of view real time images with larger field of view pre-recorded images and/or for compensating for undetected motion of the anatomy in the real time image relative to the anatomy in the recorded image. By aligning the real time image and the pre-recorded image, positions (locations and/or orientations) recorded in relation to the real time image will share the same spatial frame of reference as the pre-recorded image. Therefore, location uncertainties and errors introduced by the uncontrolled or not sensed motion of the patient and/or the image sensing/producing equipment will be greatly reduced or eliminated.

One example of an embodiment includes a method to compensate for undetected gross anatomy and/or image sensing/producing equipment movement and/or to align a smaller field of view real time image with a larger field of view recorded image to provide a larger anatomical context to the real time image. For example, before introducing a needle catheter into the left ventricle of a heart, a series of images of the interior surface are obtained. This series of images is used to assemble a view of the interior of the left ventricle, which is larger than each single view of the interior of the left ventricle. The method includes comparing the real time image with the recorded image. The comparison is performed through automatic mathematical matching or correlating one or more portions of similar content in the real time image data and the recorded image data to determine spatial offsets (location and/or orientation) and using the determined spatial location and/or orientation offsets to combine the real time image (and/or information derived from the real time image data) and the recorded image (and/or information derived from the recorded image data) in a more anatomically correct manner for display or other purposes.

In one example, the automatic matching or correlating is performed between subsets of the real time image data and the recorded image data. In one example, the automatic matching or correlating is performed on real time image data and recorded image data that overlap spatially at the spatial offsets being tested as a part of the matching or correlating process. In one example, the automatic matching or correlating is performed between data processed from the real time image data and the recorded image data.

In one example, the recorded image and the real time image are collected using the same dimensional scale. In another example, the recorded image and the real time image are collected using different dimensional scales and the image data is manipulated to share same scale prior to or during the comparison. In one example, the recorded image data set and/or the real time image data set contains information that relates to the dimensional scaling of their image data collection.

In one example of a combined image, the real time image replaces or overlays a portion of the recorded image on the display. In another example of a combined image, the real time image alternates with a portion of the recorded image on the display. In another example of a combined image, the real time image is blended with a portion of the recorded image on the display. In another example of a combined image, the portions of the real time image that are not a part of the recorded image are added to the recorded image to create a wider field of view recorded image. In one example, the displayed recorded image is encoded with diagnostic information. In one example, locations in the combined image are recorded in the reference frame of the recorded image. In one example, locations recorded relative to the real time image are adjusted using the determined spatial offsets such that the recorded location is in the anatomically correct location relative to the recorded image.

In one aspect of an embodiment, a method to guide a medical operation, includes: imaging at least a portion of a medical device and the anatomy during a medical operation, such as a percutaneous procedure, using a real time imaging system; and comparing the real time image with a recorded image to produce a representation of the medical device which is combined with guide information based on the recorded image to display the location of the medical device in relation to the guide information, where the recorded image is recorded prior to the medical operation and/or prior to the real time imaging.

In one aspect of an embodiment, a method to guide and document a medical operation includes: imaging at least a portion of a medical device and the anatomy during a medical operation using a real time 3-D imaging system, such as a 3-D ultrasound imaging system; and comparing the real time 3-D image data with a recorded 3-D image data to produce a representation of the medical device and combining the representation with guide information based on the recorded 3-D image data to show the location of the medical device in relation to the guide information on a display, where the recorded image is recorded prior to the medical operation and/or prior to the real time imaging; and diagnostic and/or therapeutic information is recorded at a medical device location relative to the recorded image and/or guide information.

In one aspect of an embodiment, a method for determining the location of the medical device relative to the anatomy includes: receiving a real time image from the real time imaging system, the real time image data containing image data of at least a portion of the medical device and the anatomy; and comparing the real time image data to a recorded image data to determine a spatial relation between the real time image and the recorded image. In one example, the comparison is performed through automatic matching or correlating one or more portions of similar content in the real time image data and the recorded image data.

In one example, the representation of the medical device in the displayed image includes at least a portion of the real time image data and/or the representation of the medical device is displayed based on data derived at least in part from the real time image data. In one example, the correlation determines a spatial relation or offset that is used to align the display of the real time image data and/or a representation of the medical device and the recorded image data and/or guide information in a combined representation or image which shows the medical device, from the real time image, within a view of the recorded image. In one example, the correlation is performed through automatic matching of image data derived from the real time image data and image data derived from the recorded image data.

In one example, the correlation is performed at time intervals to update the spatial relation or offset using the spatial relation data (e.g., location and orientation offsets) from the previous interval's correlation as the starting point for the search for the best or peak correlation in the current interval.

In one example, the spatial relation or offset is updated to include the effects of displacement(s) and/or rotation(s) introduced and/or sensed by the function of the real time imaging system (e.g., movement of the patient platform in many CT or MRI imaging systems).

In one example, combining the representation of the medical device with the guide information includes blending at least a portion of the real time image with the recorded image; and a weight for said blending is a function of a degree of correlation between the real time image and the recorded image and/or the degree/acceptability of the correlation is indicated in another manner (e.g., an image color change, a label, an indicator, etc.).

In one example, the degree of correlation or the acceptability of the correlation is used to limit and/or label location data that is recorded either alone or in conjunction with other data (e.g., allow suspect data locations to be identified, prevent suspect data locations from being recorded, etc.).

In one example, the recorded image has a field of view broader than the real time image and the recorded image was assembled from a set of images, which were recorded, each of the images in the set being used to create a larger field of view than the field of view in each of the images in the set. In one example, the guide information includes at least one of: diagnostic information recorded in the reference frame of the recorded image (e.g. diagnostic information indicating a measured electrical activity of a portion of myocardial tissue which was measured from within a ventricle of the heart, ventricular wall thickness); and operational information recorded in the reference frame of the recorded image. In one example, the guide information includes the recorded image or an image derived from the recorded image data showing anatomy or a representation of the anatomy captured in the recorded image. In one example, the guide information includes diagnostic information derived from the image data of the recorded image that is coded and/or displayed on/with the anatomy captured in or derived from the recorded image data. In one example, the guide information includes diagnostic information derived from another modality and coded and displayed on the appropriate locations of the anatomy captured in or derived from the recorded image data. In one example, the guide information includes diagnostic information that includes recorded locations and descriptors of a diagnostic result sensed at the current location and/or previous location(s) of a medical device or portions of a medical device.

In one example, the guide information includes operational information that is a recorded location(s), line(s) and/or area(s) of diagnostic and/or therapeutic interest. In one example, the guide information includes operational information that is paired recorded locations and descriptors of a therapy applied at the current location and/or previous location(s) of the medical device or portions of the medical device. In one example, the operational information includes a display of a distance(s) of a cursor, icon, device representation or a portion of a device from the nearest one or more previously recorded therapy locations and/or other recorded locations.

In one aspect of an embodiment, the recorded image is composed of a plurality of recorded images indexed according to one or more parameters describing the timing or portion of the cardiac cycle of a patient during the recording of the recorded image; and the recorded image data is displayed or chosen for other processing according to real time measurements of the one or more parameters during the medical operation. In one embodiment, the parameters include one of: Electrocardiogram (ECG) level (e.g., time after "R" wave); heart sound; blood pressure (e.g., time after average pressure is exceeded with a high positive pressure gradient); ventricular volume; pulse wave; heart motion; and cardiac output.

In one aspect of an embodiment, the plurality of recorded images is indexed or further indexed according to one or more parameters describing a hemodynamic state, parameters affecting a hemodynamic state or parameters affecting the gross position of an organ of a patient, such as at least one of: heart rate; hydration state; blood volume; blood pressure(s); sedation state; ventilation state; and respiration state; and the recorded image is displayed or chosen for other processing according to the current measurements of the one or more of these parameters.

In one aspect of an embodiment, at least one of location data and guide information is determined and/or recorded at a particular time or time interval in the cardiac cycle, preferably at a time or short time interval in the cardiac cycle when cardiac motion is minimal and cardiac dimensions are most consistent and therefore, the best alignment/correlation of the real time and recorded image or image data may be obtained. In one example, the time or time interval in the cardiac cycle of the image/image data alignment is chosen or determined such that at least one set of spatial offsets are updated at or near the particular time or time interval in the cardiac cycle. In one example, a display(s) and/or image data set(s) is created that contains at least one of guide information, the recorded image data, data derived from the recorded image data, real time image data, data derived from real time data, device image data, device icon position data or device position information at the particular time or time interval in the cardiac cycle and which is updated at the cardiac cycle interval or at a multiple of the cardiac cycle interval. Such a display or image data set, a cycle image, may be used along with a combined image display or in place of a combined image display, guide information or recorded image data to provide the means to determine and/or record the most accurate and repeatable location data and/or information paired with location data. For example, the combined image may be displayed and used to guide and position the medical device in the anatomy in real time and the cycle image may be displayed with guide information and used to determine and/or record locations and/or updated guide information. Such a display strategy provides the ability to visualize the real time position of the medical device in the context of the moving anatomy (combined image) and provides a stable, relatively unmoving, anatomy representation (cycle image, without a representation of the medical device prior to the medical operation and with a representation of the medical device during the medical operation) for the recording and/or determination of highly accurate locations and/or data paired with location data. Note that the concepts applied to create and manipulate a recorded image, a combined image or guide information may also be applied to the creation and manipulation of a cycle image. In fact, a cycle image may be thought of (and selected) as a subset of a recorded image, a combined image or guide information, where that subset is the recorded image, the combined image or the guide information at the particular time or time interval in the cardiac cycle.

In one example of an embodiment, the real time imaging system includes a real time 3-D ultrasound imaging system, such as an echo imaging system for transthoracic. echocardiogram (TTE), for transesophageal echocardiogram (TEE) and/or for intracardiac echocardiogram (ICE). The imaging system, which is used to create the recorded image(s), which are combined (e.g. overlaid) with the real time image, may be the same imaging system used to create the real time image(s) or a different imaging system. For example, the imaging system that is used to create the recorded image(s) may be a system, such as a TTE or a TEE or an ICE echo imaging system or an MR or CT or PET type imaging system.

In one aspect of an embodiment, the imaging system for real time images and recorded images is 3-D ultrasonic; and determining the location of the medical device includes: receiving a real time image data from the imaging system, the real time image data including image data of at least a portion of the medical device and the anatomy; and correlating the real time image data and the recorded image data to determine a spatial relation between the real time image and the recorded image. In one example, the correlation is performed through automatic matching of one or more portions of similar content in the real time image and the recorded image and/or imaging probe location and/or orientation data; and the representation of the medical device includes at least a portion of the real time image and/or is displayed based on data derived at least in part from the real time image. The determined spatial relation is used to align the display of the real time image and/or the representation of the medical device and the recorded image or guide information in a combined representation.

In one example of an embodiment, the real time imaging system is 3-D ultrasonic and the recorded image is 3-D, but not ultrasonic (e.g., the recorded image is created from an MRI or CT imaging system); and determining the location of the medical device includes: receiving a real time image data from the ultrasonic imaging system, the real time image including image data of at least a portion of the medical device and the anatomy; and correlating the real time image data to the recorded image data to determine a spatial relation between the real time image and the recorded image. In one example, the correlation is performed through automatic matching of one or more portions of similar content in the real time image and the recorded image and/or ultrasonic imaging probe location and/or orientation data; and the representation of the medical device includes at least a portion of the real time image and/or is displayed based on data derived at least in part from the real time image data; and the determined spatial relation is used to align the display of the real time image and/or the representation of the medical device and the recorded image and/or guide information in a combined representation.

In one aspect of an embodiment, the real time imaging system is 3-D ultrasonic and its imaging probe contains at least a portion of a location and/or orientation detection system such that changes in one or more of the probe's six 3-D location (X, Y, and Z) and optionally orientation degrees of freedom (roll, pitch and yaw) are detected or derived. The 3-D ultrasonic probe may include, for example, components of a magnetic field position determination system, such as the components of NOGA or CARTO systems, in order to determine and record the position of the probe relative to an image being captured at that position of the probe. In one example, the location detection system detects probe location and/or orientation changes relative to the patient platform, the real time imaging system, the Earth/building or some portion of the patient. In one example, the detected imaging probe location and/or orientation changes are processed and applied to the determined spatial offsets in a manner that reduces the number of search degrees of freedom and/or the range of the degrees of freedom search in the comparison or correlation algorithm that aligns the real time image or data and the recorded image or data. Thus position information (e.g. X, Y, Z, yaw, pitch and/or roll) of the probe's position during a real time imaging operation (e.g. an operation in which the probe is capturing at least one image of the heart with an intraventricular needle catheter located within a ventricle of the heart) is used to speed up the process of mathematically correlating the real time image with one or more previously recorded images. The previously recorded images may be the set of images, which are assembled to create a composite view, which has a larger field of view than each of the images in the set of images. The probe's 3-D location during real time imaging may be used to select a starting point for the mathematical correlation operations when searching for alignment between a real time image and a set of previously recorded images. This may occur by recording the 3-D location of the probe when it is capturing the images in the set of images (used to create the composite view) and comparing the 3-D location during real time imaging with those previously recorded 3-D locations of the corresponding images in the set of images. A starting point for the mathematical correlation may be selected by finding the image in the pre-recorded set which is close (based on the 3-D location of the probe when that image was captured) to current real time location of the 3-D probe.

As a further example of using probe position data, if the probe had an orientation change of +2° yaw since the last acceptable determination of the spatial offsets, those spatial offsets would adjusted by the effects of the +2° yaw change of the probe, such that the beginning spatial offsets for running of the comparison, alignment or correlation algorithm in the next interval would be the adjusted spatial offsets. In another instance, if the interval of the running of the comparison, alignment or correlation algorithm is longer than the image updating interval of the real time imaging system, the effects of the +2° yaw change of the probe on the spatial offsets may be applied directly to the real time image, real time image data and/or data derived from the real time image data. These instances are analogous to previously mentioned updating of the spatial relation or offsets to include the effects of displacement(s) and/or rotation(s) introduced and/or sensed by the function of the real time imaging system.

In one example of an embodiment, the real time imaging system captures images of a smaller portion of the anatomy than the recorded image. In one example, at least a portion of a real time image captured from the real time imaging system is overlain on the recorded image. In one example, at least a portion of a real time image captured from the real time imaging system is blended with a corresponding portion of the recorded image. In one example, the system alternates between displaying at least a portion of a real time image captured from the real time imaging system and displaying a corresponding portion of the recorded image. In one example, the field of view of the real time image is indicated in the combined display, such as by a color change, dotted lines, etc. In one example, an iconic representation of the medical device (rather than the actual real time image of the device) is overlain on the recorded image.

In one aspect of an embodiment, the display of the recorded image and/or guide information is manipulated (e.g., cut, cropped, rotated, translated, copied, scale changed, etc.) by the operator and/or according to some algorithm (e.g. a predetermined algorithm) to provide a desired or convenient view(s) of the anatomy or other guide information; and this display manipulation or algorithm is recorded and applied to the real time image, or subsequently recorded information and/or the medical device representation such that the spatial correlation and alignment of, on the one hand, the recorded image and/or guide information and, on the other hand, the real time image, subsequently recorded information and/or the medical device representation is preserved in the combined image display.

In one aspect of an embodiment, determining the location of the medical device in the combined display(s) includes: determining a three dimensional coordinate of the medical device in the coordinate system or reference frame of the recorded image or guide information from a graphical user interface by moving a cursor in the combined display(s) to align it with the applicable displayed portion of the medical device or its representation and recording and/or displaying that location. In one example, the recorded location is paired with recorded diagnostic and/or therapeutic information derived from the use of the medical device to create diagnostic or operational information. In one example, the operational information is displayed and/or encoded into the recorded image or the guide information.

In one example of an embodiment, the real time imaging system is ultrasonic; and determining the location of the medical device relative to the recorded image or guide information includes: identifying a Doppler shifted portion of the medical device from image data captured by the real time imaging system, where the portion of the medical device is vibrated, rotated or otherwise moved to create a Doppler shifted portion of the medical device image data; computing coordinates of the location of that portion of the medical device from the Doppler shifted portion of the image data in relation to the recorded image or guide information using the spatial relationship correlation of the real time and recorded images.

For example, the medical device includes a tip portion of a catheter with an element mounted that is capable of vibrating when activated. In one example, the real time imaging system is equipped to recognize the Doppler characteristics of that portion of the medical device and thus automatically determine its location relative to the recorded image or the guide information.

In one example, the location of the Doppler portion of the medical device is the displayed location of the medical device representation in the combined display. In one example, the determined location is recorded and paired with recorded diagnostic and/or therapeutic information derived from the use of the medical device to create diagnostic and/or operational information. In one example, the operational information is displayed and/or encoded into the recorded image or the guide information.

In one aspect of an embodiment, the real time imaging system is ultrasonic; and determining the location of the medical device includes: determining a delay(s) of an ultrasonic pulse(s) between an imaging probe (which may be composed of multiple transducers) of the real time imaging system and a transducer(s) mounted on the medical device; and computing coordinates of the location using the delay(s). In one example, the medical device includes a tip portion of a catheter with a multi-directional ultrasonic transducer (such a transducer may be composed of one or more transducers). In one example, the medical device, such as a catheter, includes a transducer(s) oriented relative to medical device preset bends or deflection direction such that the transducer(s) may transmit and/or receive an ultrasonic pulse(s) to and/or from the transducer(s) of an imaging probe during the medical operation.

In one aspect of an embodiment, prior to the medical operation, the method further includes: capturing using an imaging system a plurality of images of multiple portions of the anatomy, each of which has a smaller field of view than the anatomy view desired to be captured for the recorded image; and combining the plurality of images to generate the recorded image. In one example, parameters to generate the recorded image from the plurality of images are stored. Alternatively, the recorded image is stored. In one example, the imaging system used to capture the plurality of images prior to the percutaneous procedure is the same as the real time imaging system used during the percutaneous procedure.

The present invention includes apparatuses, which perform these methods, including data processing systems which perform these methods, and computer readable media which when executed on data processing systems cause the systems to perform these methods.

Certain aspects of embodiments of the inventions are directed to an echogenic medical device, such as a needle catheter, which produces an improved ultrasonic image of the device, and a method of performing a medical procedure using a device of the invention. One aspect is directed to a catheter which reduces artifacts in the ultrasound image of the catheter. In one embodiment, the tip of the catheter is directly imaged over a range of angles (relative to the catheter) substantially greater than 180°. Another aspect of the invention is directed to an echogenic catheter shaft construction, in which the amplitude of the direct echoes produced by the catheter shaft are reduced, and/or in which diffuse echoes are produced that facilitates the imaging of the catheter portions that do not produce a direct echo. Another aspect of the invention is directed to an echogenic catheter in which the imaging of a portion of the catheter reveals the rotational orientation of the catheter relative to the imaging direction.

In one embodiment, the echogenic needle catheter has a spherical distal tip which reflects sonic energy more diffusely than a non-spherical distal tip. Non-spherical tips on catheters are capable of directly reflecting sonic energy back to a transducer of an ultrasonic imaging device over range of angles of not greater than about 180° relative to the longitudinal axis of the catheter. For example, catheter tips having a rounded distal end allow for direct ultrasonic imaging of the catheter tip only from the distal front of the catheter tip up to about 90° or perpendicular to each side of the catheter tip. Beyond this range, the non-curved portion of the non-spherical tips are shielded from the sonic energy by the catheter body or produce sonic reflections that do not return directly to a transducer of an ultrasonic imaging device. Thus, unlike a spherical distal tip of the invention, conventional non-spherical distal tips on catheters cannot be directly imaged from substantially behind the catheter tip.

The spherical distal tip of the invention includes a spherical portion or portions that produce direct sonic reflections back to a transducer of an ultrasonic imaging device from a range of angles greater than about 180° (i.e., from a range of angles which extend from in front of to behind the catheter tip). The spherical shape is preferred for the distal tip because the spherical shape will directly reflect sonic energy at substantially the same amplitude over its direct reflection range of angles and will not have the higher amplitude and larger amplitude range of reflected echoes seen from flatter tips or the cylindrical portions of rounded tips. The spherical distal tip thus allows the tip to produce a direct ultrasonic image from a greater range of angles relative to the catheter than conventional tips. Specifically, the tip directly reflects the sonic energy back in the direction of a transducer of an ultrasonic imaging device, with the catheter located at a wide range of angles relative to the viewing direction of the ultrasonic imaging device. As a result, the distal end of the catheter can be manipulated, such as by tendon deflection or insertion into a vessel, and positioned at a greater range of angles within the anatomy yet still have its distal tip reliably imaged by an ultrasonic imaging system. Additionally, the spherical shape of the distal tip is atraumatic to prevent or inhibit disadvantageously injuring the patient's anatomy.

In a presently preferred embodiment, the spherical distal tipped echogenic needle catheter is configured for percutaneous transluminal advancement into a chamber of the patient's heart, although a variety of alternative catheter configurations may be used. The echogenic needle catheter generally comprises an elongated shaft having a proximal end, a distal end, and a needle lumen extending therein, with the spherical distal tip at the distal end of the elongated shaft, and a needle slidably disposed within the needle lumen of the catheter. In a presently preferred embodiment, the spherical distal tip has a lumen in communication with the needle lumen of the shaft and with a port in the in the spherical distal tip which is configured for having the needle slidably extend therethrough. The needle disposed within the catheter shaft has a distal end which extends distally from the spherical distal tip port in an extended configuration.

In a presently preferred embodiment, the spherical distal tip is formed at least in part of a conductive material to function as an electrode. The spherical distal tip electrode is formed at least in part of a metallic material. The metal in the spherical distal tip allows the tip to function as an electrode, primarily for diagnostic purposes, but, alternatively, for therapeutic purposes (e.g., defibrillation), if desired. Additionally, in one embodiment, the tip formed in part of a metallic material is configured to produce a tip pyramid artifact of a desired brightness and duration, as discussed in more detail below. In some embodiments, the presence of the pyramid artifact at a reduced level relative to conventional fully metallic distal tip electrodes is desirable to more reliably differentiate the image of the catheter tip from the image of the catheter body and thus indicate that the tip of the catheter is being imaged, but in a manner that doesn't substantially obscure the image of the adjacent anatomy.

Prior non-spherical distal tip electrodes reflect a large amplitude direct echo and often a large range of echo amplitudes over the range of direct reflecting angles, such that at angles behind the tip a direct echo does not return in the direction of the ultrasonic imaging device probe and, therefore, does not produce a direct image. In contrast, the spherical distal tip electrode of the invention more diffusely and evenly reflects ultrasonic energy. As a result, the spherical distal tip electrode can be imaged from a greater range of angles relative to the viewing direction of the ultrasonic imaging device (e.g., a range of angles greater than 180°; compared to a range of angles of not greater than about 180° for a conventional rounded end distal tip). Also, the echo amplitude of the tip is smaller and less variable over its range of imaging angles than a non-spherical metallic tip.

A catheter distal tip formed at least in part of a metallic material absorbs, stores and then reemits the sonic energy of the ultrasonic imaging device, causing the metal in the tip to ring like a bell, sending out ultrasonic energy until the sonic energy that it has stored is depleted. This absorbed, stored and then reemitted sonic energy is received by the ultrasonic imaging device and creates images behind the catheter tip that decrease in brightness and size as the stored sonic energy is depleted, forming the tip pyramid artifact. On the other hand, polymeric materials produce echoes from their surfaces in the body that are usually of less amplitude than the thick metallic surfaces of conventional electrode tips. Additionally, polymeric materials are generally more dissipative of sonic energy than metallic materials and thus, if any pyramid artifact is produced, it is of smaller amplitude than those produced by completely metallic tips. In one embodiment, the presence of the artifact is desirable to indicate that the tip of the catheter is being imaged. However, a disadvantageously bright/long duration/large tip pyramid artifact obscures the actual image of the catheter tip and surrounding anatomy. A distal tip of the invention, configured to minimize the amount of metallic material at the distal tip, reduces the amount of sonic energy that the tip stores and then reemits to thereby reduce the brightness and duration of the tip pyramid artifact. Additionally, in one embodiment, the spherical distal tip is in contact with a damping (sonic energy dissipating) material, such as many plastic/epoxy/elastomeric compounds and mixtures, which may contain air bubbles, tungsten filings and the like, to reduce the brightness and duration of the tip pyramid artifact. For example, in one embodiment, the spherical distal tip is filled with the damping material, and/or is connected to a proximally adjacent section of the shaft formed, at least in part, of the damping material.

In the absence of a direct echo from the tip, the only ultrasonic image of the tip may be that due to the absorbed, stored and then reemitted sonic energy and that image is located behind the actual location of the catheter tip (due to the delay in reemitting the sonic energy in the direction of the imaging device). As a result, the direct echoes produced by the spherical distal tip of the invention, from a large angular range, prevent or minimize the potential for misreading the position of the distal tip from the ultrasonic image, by avoiding the absence of an imaged direct echo from the distal tip.

In a presently preferred embodiment, the spherical distal tip is formed in part of a plastic/polymer material or materials, to minimize the amount of metal in the tip and thus reduce its echo amplitudes and reduce or eliminate its pyramid artifact. In one embodiment the distal tip has a plastic/polymer wall formed of a material selected from the group consisting of an epoxy, a polyurethane, a silicone, a polyethylene, and an ethylene acrylic acid functionalized polyolefin such as PRIMACOR. In a presently preferred embodiment, the tip is formed at least in part of an adhesive polymer such as PRIMACOR to assure the secure bonding together of metals to polymers or polymers to polymers in many configurations of the spherical tip, especially bonding plastics/polymers to metallic components such as hypotubes, metal shells or to thin coatings/platings of metallic conductors. Adhesive polymers may be incorporated into a spherical tip assembly in a number of ways. For instance, adhesive polymers may be mixed with another polymer to provide that polymer with adhesive characteristics or the adhesive polymer may be put into solution and applied to a surface (i.e. by dipping, spraying, brushing), such that when the solvent evaporates, a thin coating of the adhesive polymer is deposited on the surface to provide an adhesive surface for further processing. The adhesive function of the adhesive polymers is often enhanced by raising the temperature of the adhesive polymer for a short time (i.e. during a molding or forming process, as part of a conditioning cycle) and, thus are often referred to as "hot melt adhesives".

For example, in one embodiment, the spherical distal tip includes a metallic member therein with an exposed surface to function as an electrode. In another embodiment, the spherical outer surface of the tip is defined by a wall formed of a mixture of blended or otherwise combined polymeric and metallic materials. In another embodiment the spherical tip is formed of a polymeric material or materials and/or a mixture of polymeric and metallic materials and at least a portion of its outer surface is a thin metallic layer or layers, which may be deposited or attached by various conventional methods (i.e. sputtering, deposition processes in chemical solutions, pressure bonding). However, a variety of suitable configurations can be used, including a spherical tip formed of a wall of metallic material (although a metallic wall preferably defines a spherical interior chamber to minimize the amount of metal in the tip and thereby reduce the brightness and duration of the tip pyramid artifact). In embodiments in which the wall of the spherical distal tip defines a spherical interior chamber, the chamber is preferably filled with a polymeric material.

In a presently preferred embodiment, the spherical distal tip comprises a wall with a curved outer surface formed at least in part of a polymeric material and having a metallic pin member therein, or having a metallic outer layer thereon.

In one embodiment, an element(s) formed at least in part of a metallic material such as an additional conductive electrode (s) or marker(s) provided on the shaft is proximally spaced a sufficient distance from the spherical distal tip that the ultrasonic images produced by these additional metallic elements do not overlap with those of the spherical distal tip. As a result, the catheter of the invention facilitates accurately interpreting the spherical distal tip's position in the ultrasonic images. Such additional electrodes or markers may also be constructed of a limited amount of metal and/or in contact with sonic energy damping materials to provide the same brightness and artifact reduction benefits as previously described in relation to the spherical tip.

In one embodiment, a catheter of the invention has an outer jacket layer along at least a portion of the catheter shaft, formed of an impedance matching material of approximately a quarter or three quarter wavelength thickness. In one presently preferred embodiment, the layer has a quarter wavelength thickness in order to maximize the destructive interference. However, because the ultrasonic pulse waveform sent out by many echo probes is often many wavelengths long, a three quarter wavelength thickness will also produce destructive interference and can be reasonably effective in reducing the amplitude of reflected sonic energy. For example, in an embodiment in which the center frequency (imaging ultrasonic transducers typically send out sonic pulses that contain a spectrum of sonic frequencies) of the displayed echoes is high and/or the speed of sound in the material is too low, then the material thickness of the jacket might be too small to be efficiently produced/installed at a quarter wavelength thickness. For example, at 6 MHz, silicone has a quarter wavelength thickness of about 0.0015", which may be difficult to process/control, but has a three quarter wavelength thickness of about 0.0045", which facilitates accurately producing the outer jacket layer. Echo TTE and TEE systems, applicable to this technology, are advertised to operate in frequency ranges that go from about 1 MHz to 12 MHz, and a typical cardiac transducer (probe) is advertised to operate in a 2-4 MHz range or in a 3-8 MHz range.

The outer jacket layer is formed of a material with an acoustic impedance which more closely matches that of blood than does the material(s) forming the portions of the catheter shaft underneath the outer jacket layer. "Acoustic impedance" is a material property which may be defined as the velocity of sound in that material multiplied by the density of the material. For example, in one embodiment, the outer jacket layer is formed of a polymer selected from the group consisting of elastomeric polymers, low density polyethylene (LDPE), and ethylene vinyl acetate (EVA), and the underlying catheter shaft comprises a metallic braid or other metallic configuration, and/or a high acoustic impedance polymer or thermoplastic polymer more commonly used to form catheter shaft outer surfaces, e.g., nylons, Pebax, polyethylenes, polyesters, etc. In some embodiments, the outer jacket is coated with a lubricant (i.e. silicone oil based coatings like MDX) or a hydrophilic or a hydrogel coating to substantially reduce the friction and abrasive properties of the outer jacket (hydrophilic or hydrogel coatings must be wetted to reduce the friction and abrasive properties). Preferred practical outer jacket materials are most often soft/elastomeric/low modulus in nature and have rather high coefficients of friction, which may make them difficult to insert into the vasculature and more abrasive to the vasculature than desired, thus, requiring such coatings. Additionally, an irregular/bumpy/dimpled outer jacket OD and/or ID surface is preferred to provide a more scattered echo reflection and thus facilitate imaging of the cylindrical shaft at angles that would not produce a direct echo if the shaft were smooth. As a result of the outer jacket material choice, the reflection of sonic energy off the outer surface of the catheter shaft is reduced from that which otherwise results from a larger acoustic impedance mismatch between blood and the catheter shaft outer jacket. Thus, the outer jacket layer couples more of the ultrasonic energy into the catheter, so that a larger portion of the sonic energy penetrates the outer jacket layer and is transmitted through the catheter or into the shaft of the catheter and less sonic energy is reflected from the surface of the outer jacket. In another embodiment, the outer jacket includes a material/filler (i.e. tungsten fillings) that improves the sonic energy dissipation properties of the outer jacket material to reduce the amplitudes of echoes reflected by the internal portions of the catheter shaft. Sonic energy will pass through the outer jacket to be reflected by the internal portions of the catheter shaft and then back through the outer jacket again to be received by the imaging device and thus imaged. The more dissipative the outer jacket, the less of this sonic energy will be returned to the imaging device. In many embodiments, the material or filler included in the outer jacket also causes the catheter shaft to more diffusely reflect a portion of the sonic energy that penetrates the jacket back to the imaging device, such that portions of the cylindrical catheter shaft that do not produce a direct echo may be more easily imaged. Such materials/fillers may also improve the imaging of the shaft by other imaging modalities, such as fluoroscopy.

In outer jackets with irregular/bumpy/dimpled surfaces, it is preferred that the thickness of the flatter surfaces of the jacket be kept near the ¼ wavelength thickness to reduce the amplitude of the direct reflection. It should be noted that current ultrasonic imaging systems/devices may filter out the lower frequencies to improve the resolution of the displayed image, called harmonic imaging, and which therefore affects the thickness of the quarter or three quarter wavelength outer jacket (a quarter or three quarter-wavelength outer jacket thickness is twice as thick at 3 MHz than it is at 6 MHz). In general, an outer jacket thickness in the 0.001" to 0.008" range is preferred. Below/near 0.001" and coverage of metallic braids or other internal shaft components is uncertain and processing of the jacket tubing becomes a challenge. Above/near 0.008" and the jacket tends to disadvantageously increase the overall profile of the catheter. An elastomeric jacket used to form the outer jacket layer has the property of being expandable (i.e. by air pressure), such that it may be easily extruded as a tube with a wall thickness that is too thick, but then expanded and installed on a shaft in the expanded condition, which reduces the wall thickness to a desired thickness.

By producing destructive interference between the reflected waves from the OD and ID surfaces of the outer jacket, the quarter or three quarter wavelength layer reduces the amount of directly reflected sonic energy from the catheter shaft surface that may be received by the ultrasonic imaging device. Thus, the quarter or three quarter wavelength matching layer reduces the displayed brightness of the catheter body image, to thereby avoid obscuring the image of the adjacent anatomy (e.g., cardiac tissue) and avoid producing a pronounced curved body artifact as discussed in more detail below.

Unlike prior quarter wavelength matching layers provided on transducers to improve the transmission of sonic energy from the transducer into the blood and tissue of the patient's body (and also in the opposite direction), a catheter embodying features of the invention has a quarter or three quarter wavelength matching layer extending along a section of the catheter shaft which is not an electrical to sonic energy and/or a sonic to electrical energy transducer. Thus, catheter has a quarter or three quarter wavelength matching layer which is specifically configured to reduce the direct sonic reflections from a catheter shaft (and which is not configured to more efficiently couple sonic energy into and out of a transducer).

In a presently preferred embodiment, the outer jacket is formed of a mixture of two elastomeric compounds, styrene butadiene styrene and polyurethane, which is extruded into a tube under conditions that produce an irregular and bumpy OD and a smooth ID. The jacket, when installed on a catheter shaft, diffusely reflects sonic energy (low amplitude), allowing the entire shaft covered by the jacket to be imaged and not just the shaft portions that produce a direct echo. Additionally, the direct echo portions of the shaft produce a much reduced image brightness compared to conventional catheter shafts. Also, the jacket eliminates the ringing artifact from a metallic (e.g., NiTi) cage portion of the shaft located at the distal end of the shaft.

By reducing the amplitude of the direct echoes reflected by the catheter shaft and received by the imaging device, the curved body artifact of the catheter shaft is also reduced. Most ultrasonic imaging devices contain an array of small ultrasonic transducers to send and receive ultrasonic energy to form images. These small ultrasonic transducers send most of their sonic energy out in a direction that is generally perpendicular to the surface of the transducer, but, especially in small transducers, a considerable amount of sonic energy also goes out in other directions in a manner commonly referred to as "side lobes". With a conventional highly reflective (high amplitude echo producing) cylindrical catheter shaft, the reflections of these side lobes that return to the imaging device of a 3D echo system from the direct reflecting surface portion of the catheter shaft produces a bright curved image that may be mistaken for an image of the catheter shaft. Additionally, the bright curved image may obscure the images produced by the relatively low amplitude diffuse echoes that may be received by the imaging device from other portions of the catheter shaft, and may also obscure the images of adjacent tissues. By reducing the amplitude of the echoes directly reflected by the catheter shaft, this bright curved image artifact is reduced in size and brightness, while the image brightness of the diffuse echoes from other portions of the shaft and from the tissues are less impacted (ultrasonic imaging systems are designed to amplify low amplitude echo signals more than higher amplitude echo signals).

One aspect of the invention is directed to a method of performing a medical procedure using a spherical distal tipped echogenic needle catheter of the invention. The method generally comprises advancing within a patient's anatomy an echogenic needle catheter comprising an elongated shaft, a spherical distal tip which is preferably formed at least in part of a conductive or metallic material and which has a port at a distal end of the spherical distal tip, and a needle which extends distally from the spherical distal tip port in an extended configuration. The method includes directing sonic energy at the spherical distal tip from an ultrasonic imaging device, such that the spherical distal tip more diffusely reflects the sonic energy than at least a portion of a non-spherical distal tip, to produce an ultrasonic image of the distal tip within the patient.

It is preferred that the catheter be constructed in a manner that allows the catheter lumens to be flushed with water based solutions and avoids air filled voids in the catheter shaft. In one embodiment, the method includes filling the catheter lumens with an aqueous fluid, so that the catheter has a plastic-aqueous fluid interface which reflects less of the sonic energy than the plastic-air interface present in the absence of the aqueous fluid. The plastic-air interface is a stronger reflector of sonic energy than the plastic-blood or plastic-water interface. As a result, the fluid-filled catheter of the invention reduces the amount of sonic energy which is reflected back in the direction of the ultrasonic imaging device probe by enhancing the amount of sonic energy which instead penetrates the catheter and travels through the catheter to exit the catheter on the other side of the catheter directed away from the ultrasonic imaging device probe, and/or by enhancing the amount which is absorbed by the catheter material and diffusely reemitted or dissipated. As a result, the catheter curved body artifact, which can be mistakenly interpreted as illustrating an arching or bending length of the catheter body, is reduced. Thus, the standard Cath Lab practice of filling the catheter lumen(s) with water-based solutions (usually heparinized saline or fluoroscopic contrast) prior to insertion into the body, although usually not sufficient to make a catheter's shaft reflect a sufficiently low amplitude echo to eliminate or adequately reduce the curved body artifact, is nonetheless desirable for ultrasonic imaging.

An alternative embodiment is directed to an echogenic catheter, such as a needle catheter, with echogenic portions arranged in an array to facilitate determination by ultrasonic imaging of the rotational orientation of the catheter relative to a desired location within the patient. In one preferred embodiment, the rotational orientation echogenic portions are on a transvascular needle catheter generally comprising an elongated shaft having a needle lumen in communication with a needle distal port located proximal to the catheter shaft distal end, and a needle in the needle lumen configured for slidably extending through the needle distal port in the catheter shaft. The rotational orientation echogenic portions are more highly reflective than the shaft material adjacent to the portions, and are arranged in an array in which each adjacent pair of portions are circumferentially and longitudinally spaced apart from one another. The rotational orientation echogenic portion(s) oriented toward the ultrasonic imaging device probe will produce the brightest image. The position of the ultrasonic imaging device probe relative to the ultrasonic image of the catheter is shown on the display along with the anatomy. As a result, the rotational orientation of the catheter relative to the anatomy can be determined by the ultrasonic image.

One aspect of the invention is directed to a method of performing a medical procedure generally comprising advancing within a patient's body lumen an echogenic needle catheter having rotational orientation echogenic portions on an outer surface of a section of the catheter shaft, and determining the rotational orientation of the catheter relative to a desired location in the body lumen by directing ultrasonic energy at the shaft section from an ultrasonic imaging device. The sonic energy produces an ultrasonic image of the shaft section in which the rotational orientation echogenic portions do not all appear with an equal brightness for a given orientation. In a presently preferred embodiment, this is used to adjust the rotational orientation of a transvascular catheter's needle distal port within a patient's coronary blood vessel, such as a coronary sinus, vein or artery, to direct the needle into the desired heart tissue and avoid puncturing the free wall of the vessel or puncturing adjacent vessels. The array of rotational orientation echogenic portions typically is formed by two or more, and more preferably three or more echogenic portions. As a result, depending on the circumferential spacing of the rotational orientation echogenic portions, multiple rotational orientation echogenic portions are typically visible in any given ultrasonic image of the catheter but with a different brightness depending on the rotational orientation of the portions relative to the viewing direction of the ultrasonic imaging device. Thus, detailed rotational orientation information is obtained from the ultrasonic image by comparing it to the known layout of the array of rotational orientation echogenic portions. The catheter thus facilitates adjusting the rotational orientation of the catheter within the patient, to accurately position the needle at the desired heart tissue, and avoid adjacent vessels or puncturing the free wall of the vessel.

Thus, one embodiment of the invention is directed to an echogenic catheter configured to reduce or even out artifacts in the ultrasonic image of the catheter (e.g., by correcting inaccuracies in the image shape and/or location of the catheter or components of the catheter, in addition to making the images less bright). In one embodiment, a catheter of the invention has a spherical distal tip which is directly imaged over a range of angles (relative to the catheter) substantially greater than 180°. In another embodiment, an echogenic catheter of the invention allows for the determination by ultrasonic imaging of the rotational orientation of the catheter relative to the patient's anatomy by providing an array of portions of the catheter that have different echogenic properties/image viewing properties. These and other advantages of the invention will become more apparent from the following detailed description and exemplary drawings.

Other features of the present invention will be apparent from the accompanying drawings and from the detailed description, which follows.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The present invention is illustrated by way of example and not limitation in the figures of the accompanying drawings in which like references indicate similar elements.

FIG. 1D shows two 3-D ultrasound imaging volumes generated by, for example, a 3-D ultrasound probe being positioned at two different positions.

10 illustrates a method to display real time images with pre-recorded images according to one embodiment of the present invention.

Figure 11:
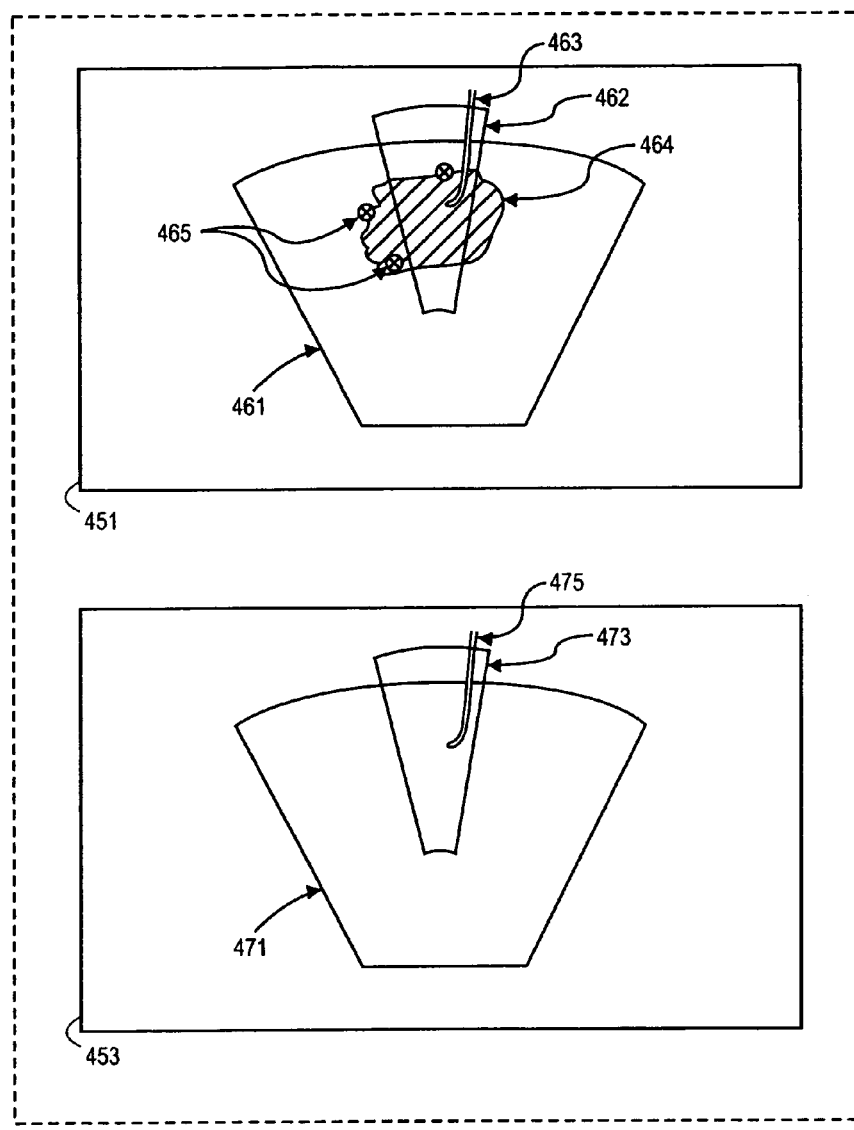

FIG. 11 illustrates another method to provide imaging and guidance information during a treatment; in this method, a first set of images, which includes a recorded image and a near real time image, is displayed concurrently with a second set of images, which includes a recorded image and a substantially real time image, and the second set of images is updated more rapidly than the first set of images.

Figure 12:
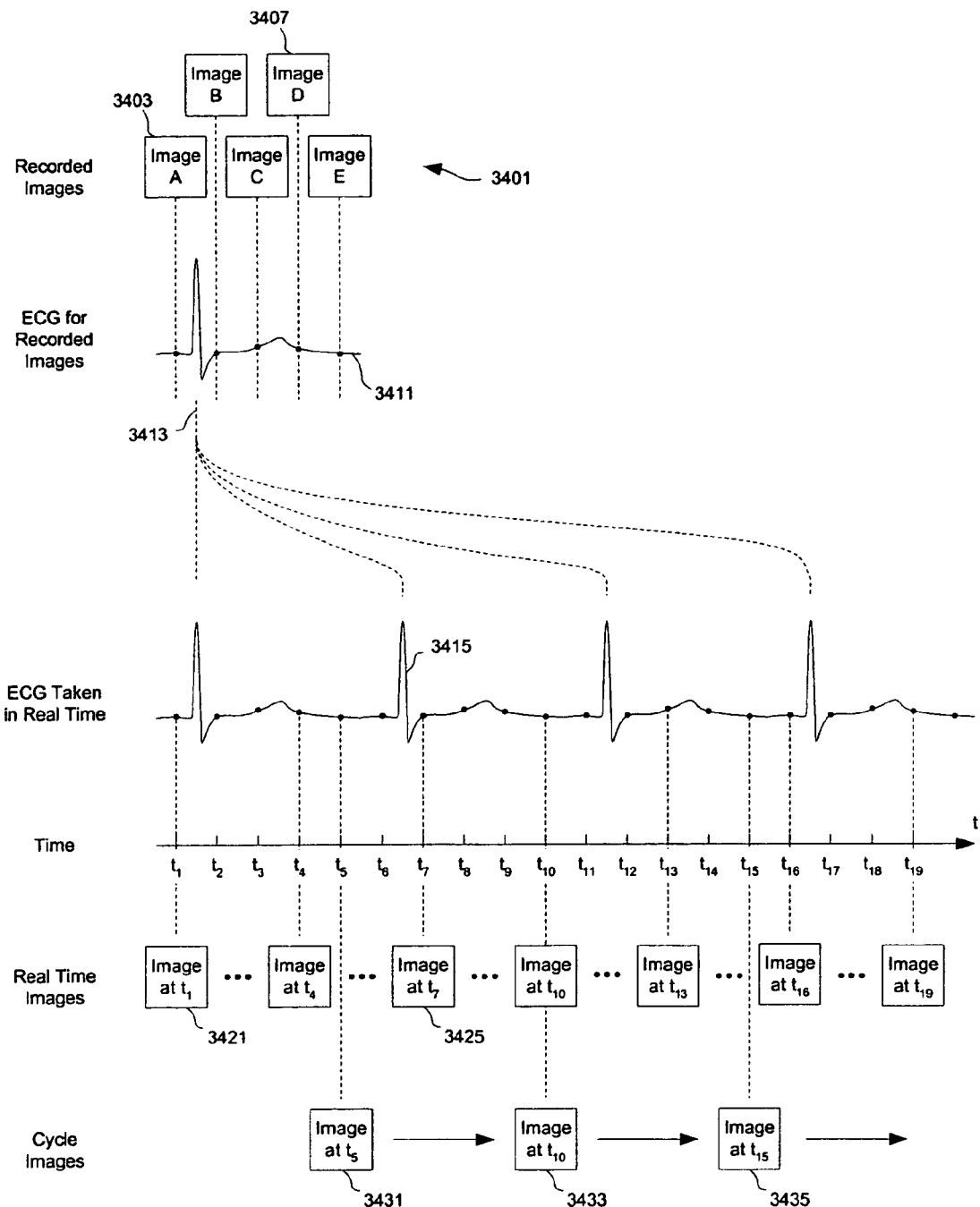

FIG. 12 illustrates a method to display images according to one embodiment of the present invention.

Figure 13:
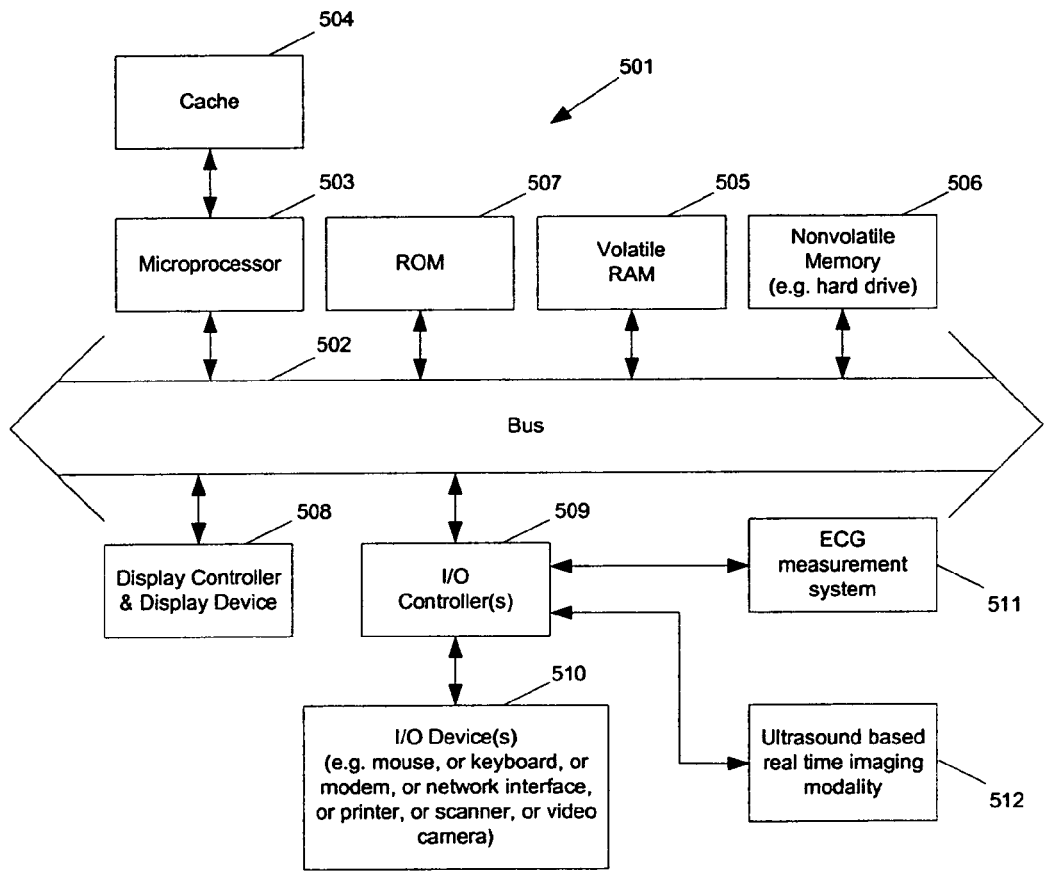

FIG. 13 shows a block diagram example of a data processing system, which may be used with the present invention.

FIG. 14 is an elevational view, partially in section, of an echogenic needle catheter embodying features of the invention, having a spherical distal tip.

FIGS. 15-17 are transverse cross sectional views of the catheter of FIG. 14, taken along lines 2-2, 3-3, and 4-4, respectively.

Figure 18:
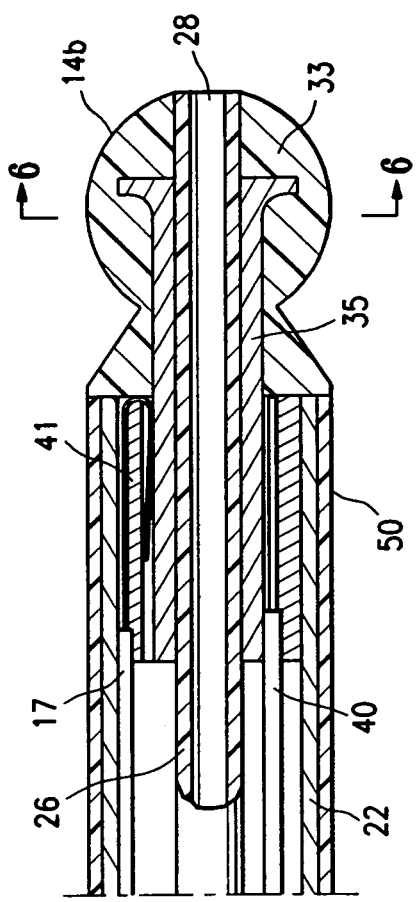

FIG. 18 is a longitudinal cross sectional view of an alternative embodiment of the spherical distal tip having a hypotube connecting member.

Figure 19:
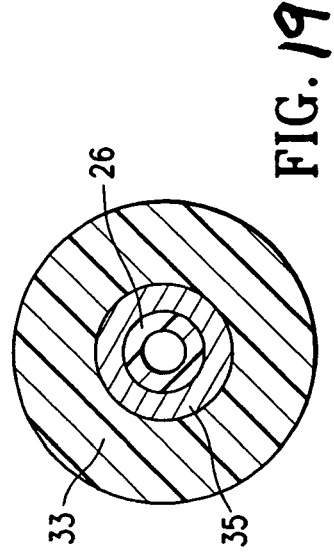

FIG. 19 is a transverse cross sectional view of the catheter of FIG. 18, taken along line 6-6.

Figure 20:
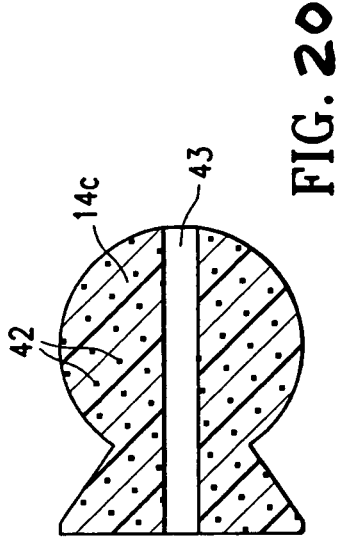

FIG. 20 is an elevational view, partially in section, of a distal end section of an alternative spherical distal tip configuration.

Figure 21:
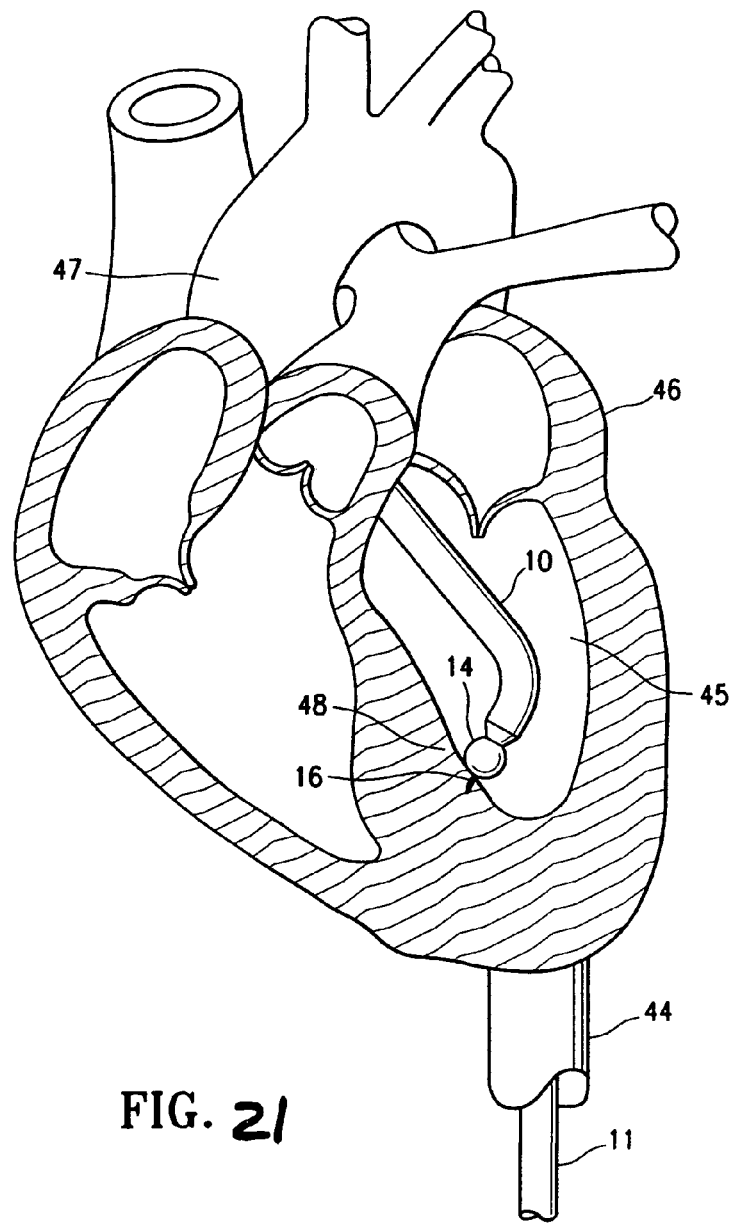

FIG. 21 illustrates the catheter of FIG. 14 within a left ventricle of a patient's heart.

FIG. 22 is an elevational view of an alternative echogenic needle catheter embodying features of the invention, having rotational orientation echogenic portions on an outer surface of the catheter shaft.

FIG. 23 illustrates an enlarged, longitudinal cross sectional view of the catheter of FIG. 22, taken within circle-10.

FIG. 24 is a transverse cross sectional view of the catheter of FIG. 22, taken along line 11-11.

Figure 25:
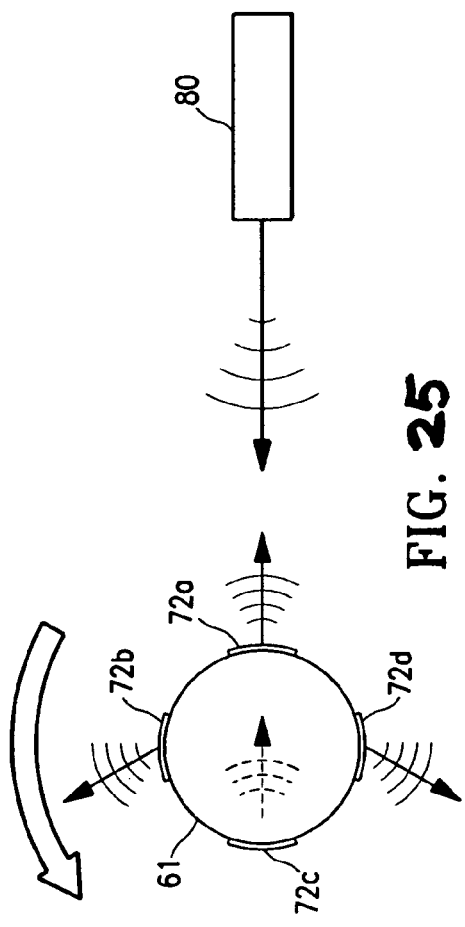

FIG. 25 illustrates the direct reflection of sound waves from an ultrasonic imaging probe relative to a transverse sectional perspective view of the catheter of FIG. 22 taken through portion 72a and looking proximally so that the proximally spaced portions 72b-d are also visible.

Figure 26:
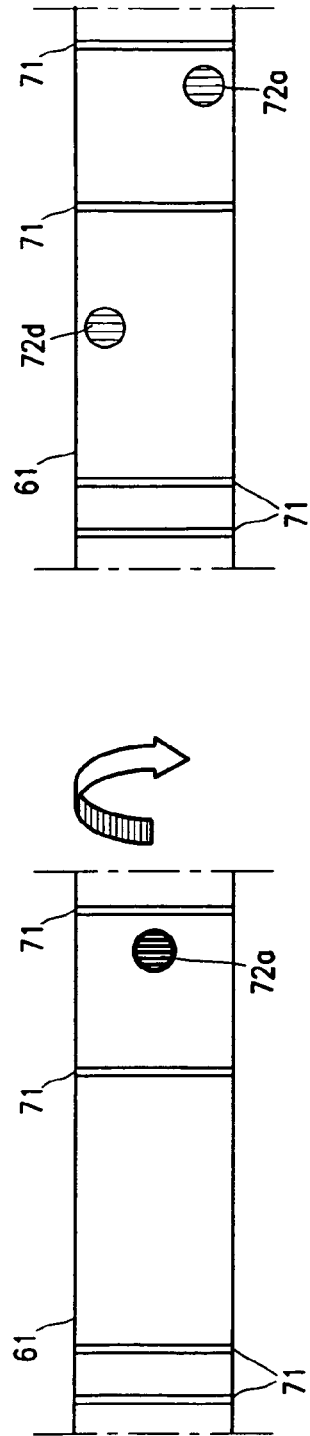

FIG. 26 is a representation of the displayed 3D ultrasonic image of a section of the catheter of FIG. 22 by an ultrasonic imaging device probe oriented relative to the catheter as shown in FIG. 25.

Figure 27:
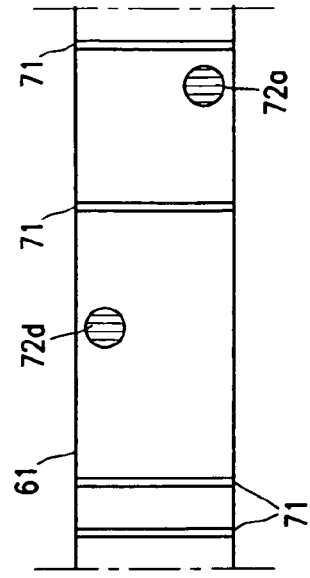

FIG. 27 is a representation of the displayed 3D ultrasonic image after rotation the catheter 45° in the direction of the arrow shown in FIGS. 25 and 26.

DETAILED DESCRIPTION

The following description and drawings are illustrative of the invention and are not to be construed as limiting the invention. Numerous specific details are described to provide a thorough understanding of the present invention. However, in certain instances, well known or conventional details are not described in order to avoid obscuring the description of the present invention.

In the present application, the term "image" is not limited to a 2-D image. The term "image" may also generally refer to a set of 3-D volumetric image data, or a 4D imaging data set that includes a series of 3-D volumetric image data paired with another dimension (such as time interval in relation to the cardiac cycle), or other types of imaging data. In the following description, the word "location" refers to the X, Y, and Z points in space or memory address locations, and the word "position" refers to general position information that may include any or all of the 6 degrees of (motion) freedom of an object in space (including X, Y, Z, yaw, pitch and roll).

At least some embodiments of the present invention involve one or more aspects of image guided medical procedures, such as:

1) preparing recorded images, diagnostic data, planned image viewing options;
2) aligning real-time images (e.g. a real time image of an intraventricular needle catheter with a left ventricle of a heart) with recorded images;
3) determining location/orientation of positions or objects of interest during the medical procedure; and
4) presenting imaging and/or position information to assist and document the medical procedure.

In one embodiment, a recorded image set is prepared before the medical operation (or before the real time display). The recorded image is prepared from a set of images of small field of views to provide a resulting large field of view (e.g. from a composite of the images having small field of view). For example, a real time imaging modality (such as a 2-D or 3-D ultrasound system) can be used to obtain a set of images of small field of views. The small field of view images can be combined into an image of a large field of view, such as a panoramic set. The recorded image may be stored as a set of re-sampled panoramic images or as the original sets of images plus the relations to compose the panoramic images. The same or similar real time imaging modality can also be used to obtain the real time image during the medical operation. This arrangement can reduce the overall modality requirement for the image-guided procedures and provide images of similar structure and quality. However, an imaging modality for the recorded image different from the imaging modality for the real time image can also be used.

Diagnostic data can be derived from the recorded image, or recorded in relation to the recorded image (e.g., in the coordinate system of the recorded image or a coordinate system having a known relation with the coordinate system of the recorded image). Thus, the diagnostic data can be superimposed on the recorded image when needed. Alternatively, the diagnostic data may be "drawn" onto the recorded image.

The recorded image set (e.g. one or more of the images used to create a panoramic image) can be manipulated for viewing. For example, the 3-D image may be manipulated (e.g., cut, crop, rotate, translate, copy, scale, etc.) to generate one or more particular views of the 3-D image. Such manipulations can be recorded for application during the real time medical procedure.

In one embodiment, image alignment of the real-time images and recorded images is performed through comparison/correlation (e.g. a machine performed mathematical correlation operation). The real-time images and recorded images are matched to each other to determine an indication of correlation. The spatial/scaling relation that provides the optimal correlation is determined as the relation for image alignment. For example, a correlation indication can be computed as the test values of rotation, translation and scaling of one image relative to another are changed in a search strategy (e.g., incrementing each test value up or down in turn and computing the new correlation value along with changing the amount of the increment under certain circumstances); and the rotation, translation or scaling test value that improves the correlation value is followed (e.g., incremented in the correlation value improving direction in the next iteration) and the process iterated to find peak correlation values, the test values of which are used as the spatial/scaling relation for alignment. Optionally and preferably, the scaling may be determined from a known or recorded scale relationship between the imaging modalities and/or the imaging data sets may contain scale information to reduce the degrees of freedom for correlation.

Correlations may be based on automatically identified anatomic or image features or specified region(s) of interest. For example, major anatomic features or surfaces can be identified through pattern recognition techniques; and the correlation can be based on matching the identified features or surfaces. In addition, lower to increasingly higher resolution image data may be compared as iterations progress/higher/peak correlation values are obtained to decrease the amount of data that must be processed and thus, speed up the process of finding a peak or near peak correlation value. Usually, 3-D image data is stored (at least at some point) as pixels (a pixel is a brightness number paired with its 3-D location in space, where that 3-D location in space of the pixel is usually known by the location (address) of that number in the storage memory; the pixel number is usually the average value of an image brightness in the center of a small cube or sphere at that 3-D location in space; the pre-determined dimensions of that cube or sphere are the best image resolution that can be stored with that particular predetermined image storage scheme). To produce lower resolution image data, groups of adjacent pixels can have their brightness numbers averaged and the location of this averaged pixel known from the average location of the pixels used. For instance, a 5 by 5 by 5 pixel cube of the high resolution image data may be a first lower resolution to be used for at least a portion of correlation processing. In this instance, the average of all or a portion (e.g., the center 3 by 3 by 3 high resolution pixel cube) of the 625 high resolution pixel brightness numbers in the lower resolution pixel cube becomes the lower resolution pixel number and the location of that pixel is the same as the pixel of the center of that 5 by 5 by 5 pixel cube. In this scheme, if adjacent (not overlapping) lower resolution pixel cubes are used, the amount of image data to process for computing a correlation value can be reduced by a factor of about 625 (depends on the high resolution image pixel dimensions). There are many possible schemes that create lower resolution image data and reduce the amount of data to be processed for at least a (early) part of a correlation process. Regardless of the specific method(s) used, data based on the real-time image and data based on the recorded image are compared to perform the alignment process. Through the comparison based correlation process, an anatomically correct alignment can be obtained.

A search algorithm can be used to search for the highest correlation point from a given starting point of a spatial/scaling relationship. The correlation may be performed periodically during the real time operation; and the image alignment parameters (e.g., rotation, translation and scaling) determined in the previous correlation operation can be used as the starting point of the current correlation operation. For example, the alignment solution in the previous correlation time interval can be used as the starting point for searching the correlation solution at in the current correlation time interval. The correlation process may automatically stop when the solution has converged, or stop based on other criteria, such as searching for a preset time period, searching until an external event occurs, until a preset threshold value of a function related to the degree of correlation/alignment is attained, and/or until a peak value of a function related to the degree of correlation/alignment is attained at the desired least significant digit of variation of the search degrees of freedom. The correlation process may automatically resume at the beginning of the next time interval (e.g., end of last time interval) or at an external event and may perform the correlation using a new/updated real-time image and/or a new portion of the recorded image (e.g., image recorded at a different time in the cardiac cycle).

The correlation can be performed in an apparently continuous fashion (e.g., in a background process) to find the improved alignment parameters of the current real-time image with the corresponding recorded image; a combination of the real-time image and the recorded image can be shown to provide feedback of the current state of alignment and/or for other purposes (e.g., real-time device guidance). For example, the real-time image can be displayed in a translucent way or other combined way over the recorded image. As the correlation process finds its best solution to the alignment parameters (e.g., highest correlation value in the time interval of the real-time image update interval or less), the display of the current or next real-time image is adjusted according to the new solution. Thus, one can graphically observe the progress or adequacy of the correlation process in which the image alignment improves through a number of real-time image updates and/or follows the movements of the patient and/or a portion of the imaging system.

In addition, a different initial image alignment method can be used. In one embodiment, an image alignment method other than alignment through comparing and correlating the image data is used to obtain a starting point for searching the correlation solution through comparing and correlating the image data. For example, a graphical user interface can be provided to receive user input to coarsely align and/or scale the images; and then the system automatically improves the image alignment through comparing and correlating the image data. In another example, a location and orientation tracking system can be used to track the location and orientation of the imaging sensing device (e.g., a 2-D or 3-D ultrasound probe or CT/MRI imaging system) relative to one or more known reference points (a previously sensed and recorded location and/or orientation by the location and/or orientation tracking system may be a reference point) to initially align the coordinate systems of the real time images and the recorded images. In another example, the location of the transducer of the imaging system (e.g., the ultrasound probe) relative to patient or the anatomy of the patient can be manually input into the system to provide a coarse initial alignment. The manual input can be in terms of a set of pre-coded position codes, or a position relation to a standard diagram, or a graphical user interface showing a video image of the patient (e.g., from a video camera) and a representation of the probe (e.g., a cursor). The video image may or may not show an image of the ultrasound probe. When the representation of the probe is in the appropriate position relative to the patient in the video image, the position of the representation of the probe can be considered as the manual input of the probe position. When the video image also shows the ultrasound probe, the user may adjust the input to point the representation of the probe at the image of the probe to provide a more accurate input. Alternatively, or in combination, the probe may be recognized through any automatic pattern recognition technique known in the art to provide a location solution.

The use of an image alignment method other than alignment through comparing and correlating the image data provides a coarsely aligned solution that can be used to reduce the field of search for correlation; and the use of the method of alignment through comparing and correlating the image data provides improved image alignment and reduces alignment accuracy requirement of the other method(s) used. In general, a number of imaging alignment methods and/or portions of image alignment methods can be used alone or in combination to improve the speed, accuracy, efficiency and user friendliness of the system.

Once the real time image and the recorded image are correlated, the real time image and the recorded image can be combined for display. For example, the real time image may be overlaid on the recorded image; or, the corresponding portion may show the real time image and the recorded image in an alternating fashion; or, the real time image may be blended with the recorded image with the anatomically correct alignment. The data processing system may also provide an indication of the degree of the amount of match or correlation between the recorded image and the real time image.

In one embodiment, a location (and/or orientation) of an object is determined based on the imaging data. For example, the medical device in the real time image can be identified through automatic pattern recognition and image comparison between the real time image and the recorded image. After subtracting pre-recorded image and real-time image from each other to cancel out the image of the anatomy and highlight the image of the medical device, the outline of the medical device in the image can be detected through edge detection operations performed automatically on a software controlled data processing system. Characteristic points of the medical device (e.g., tip) can then be determined from the outline of the medical device in the image. In another example, the location as seen in the image can be pointed at using a cursor that is movable in a 3-D space. A representation of the cursor is shown over the image in at least two images with preferably orthogonal viewing directions or planes. When the cursor is seen to be at the desired location in the two image view directions or planes, the location of the cursor coincides with the location in the image. The location can then be determined and recorded.

Alternatively (or in combination), some locations can be determined through a position determining system. For example, the medical device (e.g., catheter) can include a portion that is controllable to vibrate or otherwise provide motion when needed. When vibrating/moving, the Doppler effect of the vibration/movement of the portion in the real time ultrasound image can be detected automatically. This allows the automatic determination of the location (and/or orientation) of the vibrating/moving portion of the medical device. Using the determined spatial offsets between the real time image and the recorded image, the location of the device portion can also be determined relative to the recorded image.

In another example, the medical device can contain an ultrasonic transducer(s) which may produce and/or receive ultrasonic pulses in conjunction with the imaging probe (such as a 3-D ultrasonic probe used to produce a TTE or TEE or ICE echocardiogram) and is connected to the imaging system such that the pulses are detected by the imaging system and thus, the location of that portion of the device relative to the imaging probe/the real time image is detected from the delays between the generation of the pulse(s) and its detection. Using the determined spatial/scaling offsets between the real time image and the recorded image, the location of the device portion can also be determined relative to the recorded image.

After the identification of the medical device (e.g., the detection of the outline of the medical device, the determination of the portion and/or orientation of the tip, etc.), the system shows a representation of the medical device on the recorded image (or a combination of the recorded image and the real time image). The medical device (and/or the real time image) can be visualized according to the image manipulation sequence planned based on the recorded image. For example, one of the recorded image manipulation sequences to generate one or more views of the recorded image can be applied to the 3-D representation of the medical device (and/or the real time image with/without combination with the recorded image) to generate a desired view of the imaged information. The location and/or orientation as seen in the real time image can be recorded relative to the recorded images for later review. For example, the locations selected using a 3-D cursor (in two non-parallel views) or positions of medical devices (and/or associated diagnostic and/or therapeutic information) can be recorded relative to the recorded image (and/or the real time image).

Figure 1A:
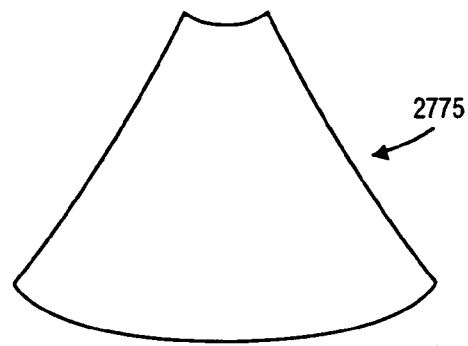
FIG. 1A shows an image area generated by a 2-D ultrasound probe (or a slice, in 2-D, from an image generated by a 3-D ultrasound probe)
Figure 1B:
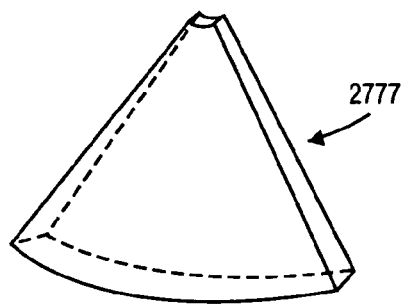
FIG. 1B shows a 3-D ultrasound imaging volume.
Figure 1C:
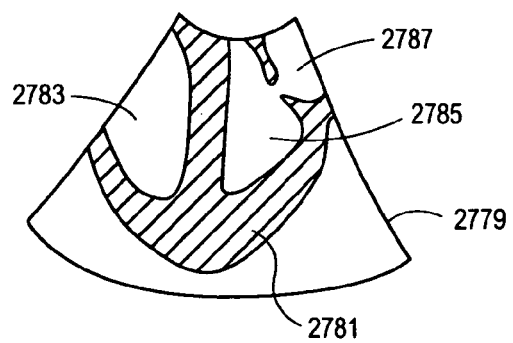
FIG. 1C shows an image in a slice (in 2-D) of a 3-D ultrasound image of the left and right ventricles of a human heart.

Further detailed examples are provided below after a brief discussion about echo imaging and other types of imaging. There are at least two types of ultrasound, or "echo," imaging: 2-D (two-dimensional) and 3-D (three-dimensional). A 2-D echo image is generated by a 2-D echo imaging probe which makes a thin slice-like image with an outline 2775 shaped as shown in FIG. 1A. A 3-D echo imaging probe generates a 3-D echo imaging volume such as the volume 2777 shown in FIG. 1B. The echo imaging probe is located at the top/small end of the fan-like shape for both the 2-D and 3-D imaging shapes. This fan-like shape differs from the imaging shapes that are generated by other types of medical imaging systems such as MRI and CT (e.g. X-ray based) systems. MRI systems and most CT (X-ray based) systems create 3-D image data that represents a rectangular parallelepiped volume (e.g. a box) of space/tissue. Usually, two spatial axes (e.g. x and y axes) of the MRI, CT and echo imaging volume will encompass all (or a sizeable portion) of the imaging region of interest (e.g. a heart chamber, the heart, all or a portion of the chest, etc.) along those two axes and multiple images (e.g. "slices") are collected along the third spatial axis (e.g. the Z axis). It is usually mostly along the third axis (or changes in orientation for 3-D echo imaging) that the images are created and assembled to obtain a wider field of view. Two different positions of a 3-D echo imaging probe may create the two different 3-D echo imaging volumes 2791 and 2793 shown in FIG. 1D, and a slice through one of those volumes, if the ventricles of a heart were imaged, is shown in FIG. 1C. By varying the position (X, Y, Z and orientation) of a 3-D echo imaging probe, a volume of tissue (e.g. a heart) larger than a single imaging volume may be assembled from the set of volumes. Each slice (e.g. a 2-D plane) through a volume of a 3-D echo imaging volume represents a 2-D image such as the image of the ventricles (left ventricle 2785, right ventricle 2783) and right atrium 2787 of the heart 2781 shown in FIG. 1C. In some cases, for 3-D echo imaging, the situation can be more complex due to changes in the probe viewing position on the body (e.g. from a parasternal view (probe between the ribs) to an apical view (e.g. probe under the rib cage)), but these changes will usually represent a new real time image data collection (e.g. the imaging probe is removed from the body and placed in a new position on the body--an example of this type of change is shown in FIG. 1D which shows two different 3-D echo imaging volumes).

Any 3-D image having image data that represents a volume of space/tissue can be sliced (e.g. intersected by a specified 2-D plane) to create a 2-D image of that slice or a 3-D image subset of the 3-D image that would be viewed in one of the directions perpendicular to the plane of that slice, such as a 2-D image slice display format. Interpolation is often used when creating a 2-D view of the 3-D image data on a display device (e.g. a CRT or LCD display of a computer system), especially for 2-D image slices; this interpolation typically involves determining a pixel value (e.g. image intensity) based upon adjacent pixels or image data, and interpolation tends to produce a smoother image. A 3-D image is usually presented on a 2-D display (e.g. a CRT or an LCD display/monitor) in at least one of 3 ways. A first way is a see-through view which presents all of the applicable 3-D image data in the 3-D imaging volume being viewed as it would be seen from a particular point of view, and the user may manipulate that point of view (e.g. by moving the point of view in one or more of X, Y, Z, and also pitch, yaw, and roll). Pixels that would be viewed as being behind another pixel add to the brightness of the pixel in front (relative to the point of view) and smoothing (e.g. interpolation) of the image is usually minimized. A second way is a surface view which connects adjacent pixels at or above a predetermined brightness (e.g. pixel intensity) in the applicable 3-D image data in the 3-D imaging volume being viewed to create surfaces that are usually displayed at about the same level of brightness or as illuminated from a predetermined light source (to impart a 3D quality) and are usually displayed as opaque and do not display pixels below the predetermined brightness level. This view (a surface view) can be thought of as maximal image smoothing. The user can also manipulate their point of view in the surface view (e.g., by moving the point of view in one or more of X, Y, Z and also pitch, yaw and roll). The third way is a 2-D image slice, which has been previously described, of the applicable 3-D image data in the 3-D imaging volume being viewed, and the user may also manipulate their point of view of the 2-D image slice (e.g., by moving the point of view in one or more of X, Y, Z, and also pitch, yaw and roll).

In one embodiment of the present invention, a system uses images obtained at different viewpoints, imaging positions and/or imaging system portions to obtain a set of recorded images of expanded field of view, which may be considered a panoramic view relative to each image, which was used to create the expanded field of view. For example, currently available real-time 3-D echo imaging systems (e.g., 3-D ultrasound), or MRI or CT systems, may not be able to image a large volume of tissue rapidly enough for ECG synchronization without losing resolution. However, these imaging systems can adequately image a small volume of tissue rapidly. In one embodiment of the present invention, an imaging system such as real-time 3-D echo imaging system for TTE (transthoracic echocardiogram) is used to image multiple small volumes of tissue rapidly at different orientations relative to the probe, locations and/or originations; and the images of small volumes with a small field of view are combined into a broad view of a large volume (providing a larger field of view than is provided by the images of small volumes) of the tissue without losing resolution.

Figure 1E:
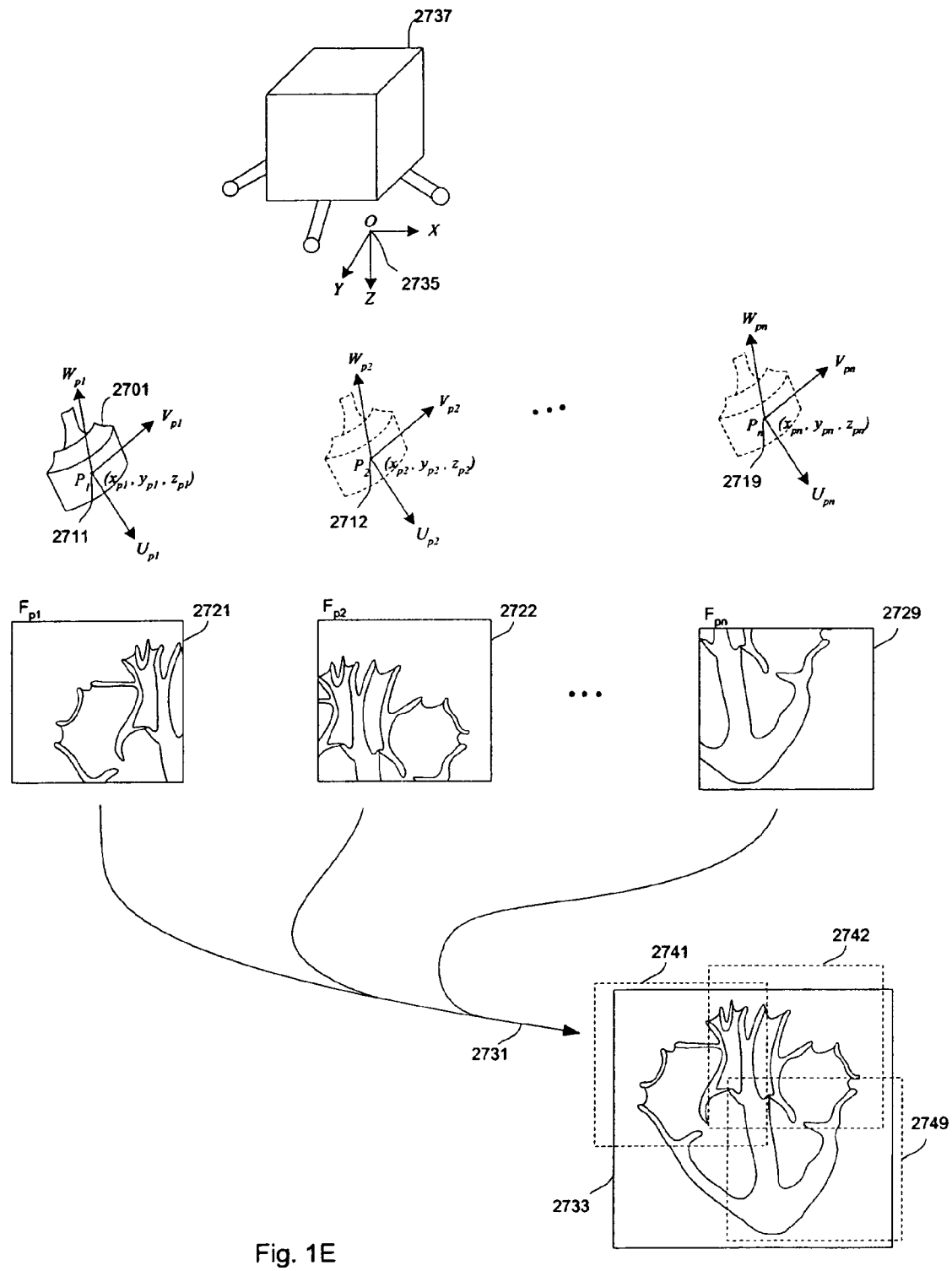
FIG. 1E illustrates a method to generate cardiac images which can be used to guide a cardiac therapy according to one embodiment of the present invention.

FIG. 1E illustrates a method to generate cardiac images, which can be used to guide a cardiac therapy according to one embodiment of the present invention. This embodiment may use 3-D echo imaging systems, and thus the system creates a 3-D imaging volume when an image is captured; FIG. 1B shows an example of such a volume. In order to use less complex drawings, 2-D image slices of these 3-D volumes are shown in FIG. 1E, and the fan-like shape of the slices and volumes has been omitted. In FIG. 1E, an imaging probe (2701) is used to obtain small field of view images (e.g., 2721, 2722, ... 2729) of portions of a heart from different locations and from different orientations of the probe 2701. A position determination system (e.g., 2737) is used to determine the location (e.g., X, Y, Z) and orientation (e.g., yaw, pitch, roll) of the imaging probe (2701) or some portion of the location and/or orientation of the imaging probe (2701). The probe 2701 may be a 3-D echo (ultrasound) probe, which is moved into different locations and orientations (e.g., as shown by the resulting imaging volumes in FIG. 1D) to create the different images. Each location and orientation of the probe 2701 creates a different 3-D imaging volume that is combined to create a composite 3-D imaging volume having a field of view (or volume) that is larger than the field of view (or volume) of the individual 3-D imaging volumes used to create the composite 3-D imaging volume. A 2-D slice from the composite 3-D imaging volume is shown as image 2733.

In FIG. 1E, the position determination system (2737) can be one of various position determination systems known in the art. The position determination system (2737) may be an ultrasonic, gravimetric, magnetic, electromagnetic, electric field and/or mechanical system. For example, the position determination system (2737) may include sensors which receive signals (e.g., ultrasonic, magnetic, laser, infrared, or radio frequency) and/or senses a field property or properties from a transmitter or field generator mounted on or in the imaging probe (2701) to determine the location and/or orientation and/or location and/or orientation changes of the imaging probe (2701). Alternatively or in addition, a receiver or sensors may be mounted on or in the imaging probe to receive signals or sense a field property or properties from the natural environment and/or from one or more transmitters and/or field generators of known and/or fixed location(s) and/orientations. Additionally, position determining system (2737) may be a portion of a position determining system. For example, in a preferred embodiment, the imaging probe (2701) may contain a tilt sensor (also commonly referred to as inclinometers or orientation sensors). Commercial tilt sensors are usually based on the earth's gravitational field (using accelerometers) and/or magnetic field (using magnetometers) and thus require no field generator. However, in a Cath Lab or other environments, a coil(s) or magnet(s) (a magnetic field generator) may be required or desired to improve magnetometer/tilt sensor performance. Tilt sensors containing both magnetometers and accelerometers are capable of providing 3-axis orientation sensing (yaw, pitch and roll). An imaging probe (2701) containing a 3-axis tilt sensor provides orientation data that effectively limits the search range of an image correlation algorithm in the 3 orientation degrees of freedom (yaw, pitch and roll) even though the orientation of the imaging probe (2701) is commonly changed over a wide range during a real-time image data collection. And, since the location degrees of freedom of an imaging probe (2701) (X, Y and Z) are commonly only changed over a small range during a real-time image data collection, the image correlation algorithm will rapidly correlate the real-time images with the recorded images, if the imaging probe (2701) contains a 3-axis tilt sensor. Further, if the probe is operated from outside of the body of the patient (e.g., in a TTE system), the probe location and orientation and/or location and orientation changes can also be determined from the known/sensed dimensions and known/sensed orientations of mechanical structures designed to hold and support the probe. The position determination system (2737) may also use the video cameras to determine the location and/or orientation of the imaging probe (2701) through processing the video frames captured by the video cameras.

The images (2721, 2722, . . . , 2729) are based on a coordinate system that is relative to the imaging probe (2701). When the location and orientation or the changes in location and orientation of the imaging probe (2701) for the corresponding images are known with respect to a common spatial frame of reference (e.g., the frame of reference 2735 of the position determination system, the frame of reference of one of the images to be combined, or any defined or recorded frame of reference), the images can be combined (2731) to form a large view field, such as the image (2733). For example, the images (2721, 2722, . . . , 2729) of portions of the heart can be transformed in coordinates, through rotation and translation according to the location and orientation of the imaging probe, to fill in the corresponding areas and form an overall image (2733) without losing resolution.

For example, according to the location and orientations (2711, 2712, . . . , 2719) of the imaging probe, the images (2721, 2722, . . . , 2729) can be identified as portions (2741, 2742, . . . , 2749) of the combined image (2733). Thus, the combined image (2733) is generated from the images (2721, 2722, . . . , 2729).

In one embodiment, the system determines a partition of the combined image (2733) with non-overlapping regions; and different regions are based on different ones of the original images (2721, 2722, . . . , 2729). For example, the boundary of the non-overlapping regions can be the mid-point to two closest overlapping boundaries of the corresponding original images.

Alternatively, the image content of the original images (2721, 2722, . . . , 2729) in the overlapping regions can be blended to determine the corresponding image content of the combined image (2733). The overlapping original images may be assigned equal weight for blending the images in the overlapping regions. Alternatively, the weight for blending the images can be computed based on the distance to the boundary of the corresponding images so that the weight reduces (e.g., to zero or other values) when the point is at the boundary of the original image.

In one embodiment of the present invention, the system matches the overlapping regions to better align the images taken from different locations and/or orientations so that the accuracy requirement of the position determination system can be reduced and undetected anatomy motion compensated for. Further, in one embodiment, the system detects the overlapping regions with, or without, the help from the operator to combine the original images (2721, 2722, . . . , 2729) into the image (2733) of a large view field. For example, the operator may help the system to detect the overlapping region through dragging the one image to the approximate location with respect to another image (or other images) in a graphical user interface where the original images are displayed as selectable objects. In such an embodiment, the use of the position determination system (2737) can be eliminated. Alternatively, the position determination system (2737) is used to determine the starting point of coarse alignment and/or to detect changes in location and/or orientation from previous alignment solution; and the automatic correlation process improves the alignment through comparing and matching the image information in a limited search range around the starting point (or starting point adjusted by the detected changes) of coarse alignment.

Alternatively, if the position determination system only supplies a portion of the location and/or orientations of the probe, the position determination system (2737) is used to determine the starting point (location and/or orientation offsets) of coarse alignment and/or to detect changes in location and/or orientation from previous alignment solutions of the determined location and/or orientation parameters; and the automatic correlation process improves the alignment through comparing and matching the image information in a limited search range around the starting point (or starting point adjusted by the detected changes) of coarse alignment for the determined location and/or orientation parameters. The location and/or orientation parameters not determined by the position determination system are determined using the automatic correlation process, using a larger search range around the starting point than used with the determined parameters. In a preferred embodiment, the imaging probe contains what is commonly referred to as a tilt or orientation sensor or inclinometer. Tilt sensors are used to determine the orientation (yaw, pitch and/or roll, which may be identified as $\theta_1$, $\theta_2$, $\theta_3$)/orientation changes of an object and are usually composed of gravimetric and/or magnetic based sensors. Miniature 2 or 3 axis tilt sensors are commercially available and may be easily incorporated into an imaging probe. While the magnetic portion of a 3 axis tilt sensor commonly senses the Earth's magnetic field and such a weak magnetic field can be substantially interfered with in many medical environments, it is very simple to provide a much stronger magnetic field that will not be substantially interfered with for the magnetic portion of tilt sensor using such uncomplicated devices as a magnet(s) or a coil(s) carrying an electrical current. Thus, the orientation degrees of freedom/changes in the orientation degrees of freedom may be, at least, coarsely known for the imaging probe in a relatively simple and inexpensive manner.

In one embodiment, the imaging system can provide a measure of the scales of the images the system captures. For example, the imaging system can provide the corresponding real-world scale of the image (e.g., the scale factor(s)) are recorded in a predetermined way in a header of an image data file during image acquisition, the scale setting is read from the system settings during real-time imaging). After the scaling factors between the images are read, the image data may be adjusted to share a common scale and the alignment process can correlate the images to determine the rotation and/or translation parameters without having to determine the scaling factors during the correlation process. Such an arrangement speeds up the correlation process. Alternatively, the correlation process may further include the determination of the scaling factors for improved alignment (e.g., using the scaling factors determined from operator measurements or manipulations as a search starting point).

In one embodiment, a new image data set is generated to represent the resulting large field of view image (2733). Alternatively, the parameters to the composite image (2733) from the small field of view images (2721, 2722, ..., 2729) are stored so that the resulting large field of view image (2733) can be generated from the small field of view images (2721, 2722, ..., 2729) on demand.

In one embodiment of the present invention, the position determination system is fixed, or registered, relative to the patient. Thus, the combined image (2733) can be recomposed based on the original images in or relative to the coordinate system of the position determination system.

In one embodiment of the present invention, the patient may move with respect to the position determination system. The position determination system further determines the location and orientation of the patient, in additional to the location and orientation of the imaging probe. Thus, through the common, fixed reference system of the position determination system, the images taken from different locations and orientations can be converted into a reference system with respect to or relative to the patient for combination into an image of a larger view field.

In one embodiment of the present invention, the patient may move in a limited manner with respect to the position determination system. The position determination system determines the location and/or orientation of the imaging probe. Thus, all or a portion of the movements related to the imaging probe's motion may be removed from the images and the correlation search to align the images limited to the patient's possible motion in the six degrees of freedom.

In one embodiment of the present invention, the location and/or orientation solution of the position determination system is used only to determine the coarse, starting alignment point. An image comparison and matching based correlation process is used to improve the image alignment. Thus, the movement of the patient would not impact on the quality of the resulting image (e.g., 2742), since the image correlation process corrects the offset/error undetected by the position determination system.

Note that in FIG. 1E, the images may be synchronized with ECG looping of the patient for composition. For example, the original images (2721, 2722, ..., 2729) are selected to correspond to the same phase of the cardiac cycle according to ECG looping; and the combined image (2733) with expanded view is also associated with the same phase of cycle of heart beat according to ECG looping. Images of different phases are indexed according to the ECG data so that the combined images can be played back according to real time ECG.

Further, in one embodiment, the images are further indexed with respect to the state of the respiration system and/or other hemodynamic states (e.g., blood pressure, heart rate, hydration state, blood volume, cardiac output, sedation state, ventilation state, respiration state, or others) so that the recorded images can be played back according to the corresponding states during the medical procedure.

In one embodiment of the present invention, a real time 3-D ultrasound echo imaging system is used for recording the 3-D images, which are played back for guidance during the percutaneous procedure. Currently, 3-D echo imaging systems are much less expensive than other 3-D imaging systems, such as a CT and MRI systems, and can be profitably employed when not in use for catheter guidance. Although such an approach can also be used with MRI and CT systems, 3-D echo imaging systems may be preferred because ultrasound based systems have few side effects and fewer usage limitations than other systems, in addition to the low cost. Currently, MRI and CT are more expensive than 3-D echo imaging systems; and, both MRI and CT systems also suffer from field of view problems, in which they can't image a large volume of tissue rapidly (for ECG Synchronization) without losing resolution but can adequately image a small volume of tissue rapidly. Such MRI and CT systems can also be used to capture multiple images for a combined, recorded large field of view images and to capture real time, small field of view images.

In one embodiment of the present invention, a real-time 3-D echo (ultrasound) imaging system is used to guide the medical procedure and to determine the location and/or orientation of the medical device (e.g., catheter) during the medical procedure.

Figure 2A:
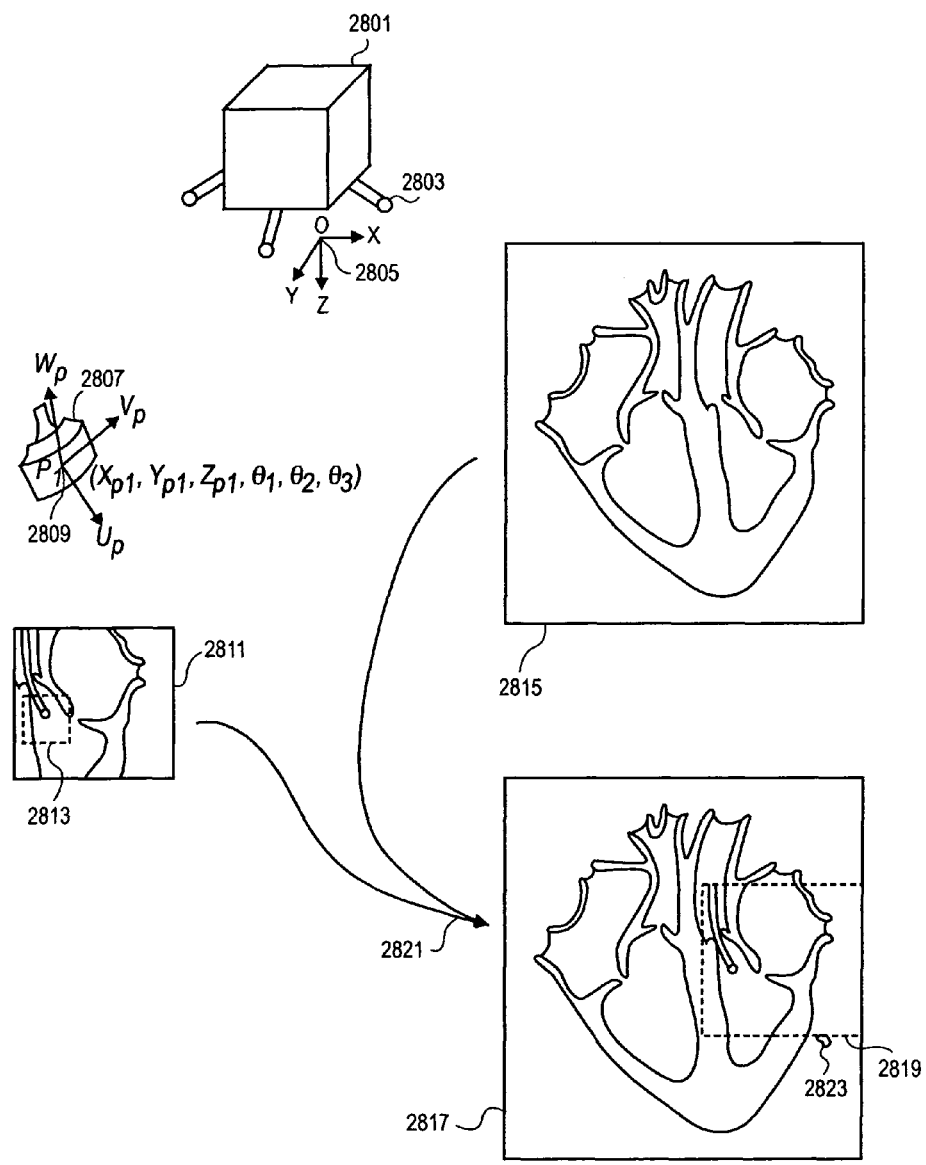
FIG. 2A illustrates a method to guide a cardiac therapy using real time images and pre-recorded images according to one embodiment of the present invention.

FIG. 2A illustrates a method to guide a cardiac therapy using real time images and pre-recorded images according to one embodiment of the present invention. In FIG. 2A, the imaging probe (2807) of a real-time 3-D imaging system is used to obtain the real-time 3-D image (2811) of a portion of the tissue of interest. Due to the limitation in the real-time 3-D imaging systems (e.g., echo imaging system, CT or MRI), a relatively small volume of tissue of a relatively large volume of tissue of interest can be imaged rapidly for ECG synchronization or within a limited period of time. To improve guidance, the real time image of the small volume of tissue is combined (2821) with the pre-recorded images of the large volume of tissue (2815) so that the position of the real-time imaged portion with respect to the relatively large volume of tissue can be clearly displayed (e.g., as image 2817). The embodiment of FIG. 2A may use 3-D echo imaging which creates a 3-D imaging volume when an image is captured; FIG. 1B shows an example of such a volume. In order to use less complex drawings, 2-D image slices of these 3-D volumes are shown in FIG. 2A, and the fan-like shape of the slices and volumes has been omitted.

In FIG. 2A, the recorded image (2815) does not show the medical device, since it is prepared before the medical device is inserted. The recorded image (2815) shows a large portion of the anatomy. The real time image (2811) shows the medical device relative to a small portion of the anatomy. When the real time image is combined with the recorded image, the location and orientation of the medical device relative to the large portion of the anatomy in the combined image (2817) can provide better guidance than the real time image (2811).

In one embodiment of the present invention, the position determination system (2801) is used to determine the location and/or orientation of the imaging probe. The position determination system (2801), including the sensing (or transmitting) devices (e.g., 2803), can be similar to the system as described above for the position determination system (2737), using at least one of ultrasonic, magnetic, electromagnetic, gravimetric and/or mechanical relations to determine the location and orientation and/or the location and orientation changes of the imaging probe (2807). The location of the position determination system (2801) with respect to the patient is fixed, known or also determined using the position determination system (2801) (or a different position determination system not shown in FIG. 2A). The real-time image is then mapped to a coordinate system of the pre-recorded images (2815), which are in a known coordinate system relative to the patient or the imaging probe. Thus, the real time image (2811) can be overlaid as the portion (2819) on the pre-recorded image.

In one embodiment, the position determination system (2801) or a portion of a position determination system (2801)

is used to determine a coarse alignment or a portion of a coarse alignment between the real time image (2811) and recorded image (2815). An image correlation process based on comparing and matching similar imaging information is used to further improve the image alignment, in a way similar to correlating the small field view images in FIG. 1E.

Alternatively, the position determination system (2801) may be eliminated; and the image alignment is performed through the image correlation process based on comparing and matching. There are numerous well known image correlation or registration methods which may be used. For example, image alignment and/or registration techniques which are for aligning images of stars (e.g. Registax) may be used. Alternatively, a graphical user interface provides a cursor (2823), which allows a user to manually adjust the image alignment parameters for a coarse alignment. To provide alignment of two 3-D image data sets, the graphics user interface allows one to adjust the image alignment parameters in two different non-parallel view angles, preferably orthogonal ones, to achieve 3-D alignment. For example, the operator may help the system to detect the corresponding region through dragging the real time image to the approximate location of the corresponding portion of the pre-recorded image in a graphical user interface where the real time image is displayed as a selectable object with the pre-recorded image, or manually adjusting representations of alignment parameters through input devices, such as joysticks, trackballs, sliders or cursor controlled graphical sliders. In such an embodiment, the use of the position determination system (2737) may be eliminated.

In one embodiment, the real time image (2811) replaces the corresponding portion of the pre-recorded image. Alternatively, the real time image (2811) is blended with the portion of the pre-recorded image as if the real time image (2811) (or the pre-recorded image) is translucent. Alternatively, the real time image and the corresponding portion of the pre-recorded image are displayed in an alternating fashion.

In one embodiment of the present invention, the system matches the real-time image to the corresponding pre-recorded image to better align the images (e.g., through mutual information maximization or correlation value maximization). Thus, the accuracy requirement of the position determination system (2801) can be reduced. Further, patient movement can be automatically compensated through the image matching based correlation. Further, in one embodiment, the system detects the corresponding region with, or without, the help from the operator to overlay the real time image (2811) onto the pre-recorded image.

In general, the methods to obtain the recorded images, as illustrated in FIG. 1E, and the methods of recorded image guided procedure, as illustrated in FIG. 2A, can be used together in the one system, or used separately in different systems. For example, the recorded image (2815) of the method of FIG. 2A may be obtained using a method as illustrated in FIG. 1E, or other methods (such as non-real time CT scanning or MRI scanning). Similarly, the combined image (2733) of FIG. 1E may be used as the recorded image (2815) in the method of FIG. 2A, or in other methods (such as using a position determination system to determine the location and orientation of a catheter for overlay on the recorded image, as illustrated in FIG. 17 of U.S. patent application Ser. No. 10/390,065).

In one embodiment of the present invention, the methods of FIGS. 1E and 2A are combined. The recording and the generation of the 3-D guidance images and the overlaying of real-time images for guidance can use the same or a similar 3-D imaging system (e.g., echo imaging system). If the same or a similar 3-D echo imaging system is used for recording the 3-D images, equipment costs are minimized; and no expensive separate position determining system required for guiding the location and orientation of the percutaneous device (e.g., a catheter). Additionally, image characteristics and data file structures will then be the same, making image correlation much easier without format conversion(s).

In one embodiment of the present invention, when the same or a similar 3-D echo imaging system is used for preparing the guidance images and for real-time guidance, the recorded 3-D images and the real-time 3-D images can be arranged to intrinsically have the same patient relative coordinate system for alignment in spatial and/or scaling relations.

Figure 2C:
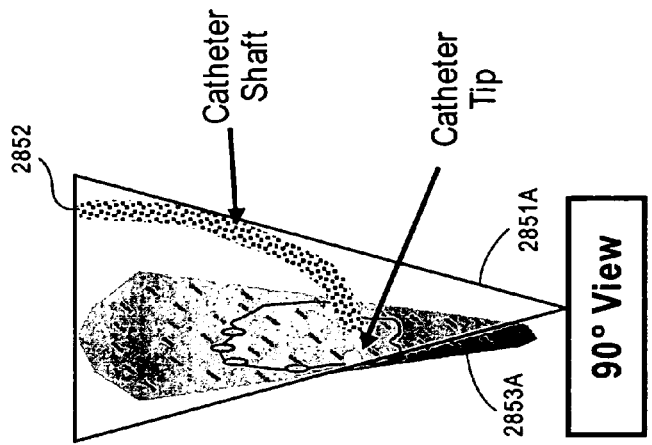
FIGS. 2B and 2C show two different views of the type of images which can be provided by at least some embodiments of the invention.
Figure 2B:
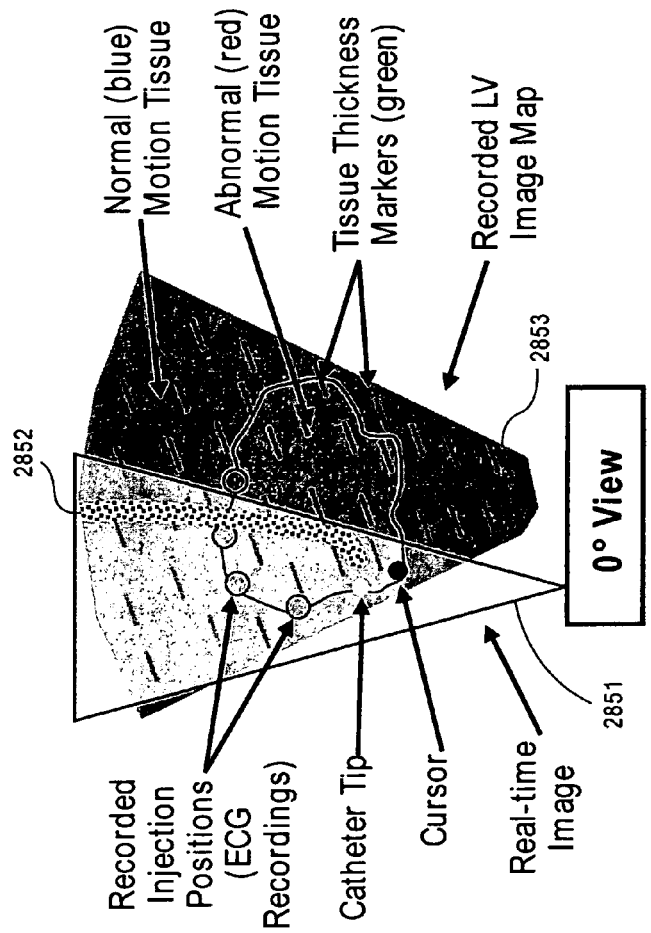

FIGS. 2B and 2C show color images to illustrate certain embodiments of the invention. FIG. 2B shows the display, on a display device coupled to a 3-D echo imaging probe, of a real time image 2851 (shown as a see-through image) of a portion of a left ventricle with the distal end of a needle catheter 2852 in the left ventricle and a previously recorded image 2853 of the same left ventricle which has a larger field of view relative to the field of view of the real time image 2851. The perspective (or point of view) of the images in FIG. 2B is at an orientation of 0° while the perspective of the images in FIG. 2C is at an orientation of 90°. The recorded image 2853 is created by assembling several different 3-D echo imaging volumes obtained by moving the 3-D echo imaging probe to different positions and/or gathering image data from different portions of the imaging probe and capturing a 3-D echo imaging volume at each of the different positions or portions of the imaging probe. The several different 3-D echo imaging volumes are aligned (e.g. through an alignment process that includes automatically aligning and registering the volumes by a mathematical correlation process and/or knowledge of the probe construction) to create a composite of the volumes which is used to generate the image data that is used to display the recorded image 2853.

The recorded image 2853 includes diagnostic information (e.g. normal and abnormal tissue motion indicators) and also includes treatment information (e.g. recorded injection positions). The diagnostic information may be created at the time of creating the different 3-D echo imaging volumes by measuring the motion of selected points, lines or areas along the interior wall (or exterior wall) of the left ventricle at several different points within a cardiac cycle as determined by also monitoring the patient's ECG. The motion of each point, line or area through the cardiac (e.g. ECG) cycle can be determined from the image data in different 3-D echo imaging volumes taken at different times in the cardiac cycle. The measured motions may be depicted by different colors (or using other user interfaces) on the displayed recorded image 2853 so that the operator can see those regions of the myocardium, within the left ventricle, which are abnormal (e.g. ischemic myocardial areas and/or areas affected by a myocardial infarction) and those regions which are normal. The motion information is shown in the examples of FIGS. 2B and 2C by using red to indicate abnormal motion tissue and blue to indicate normal motion tissue. The diagnostic information may also include measurements of the thickness of the myocardium of the left ventricle at various positions, and these thickness measurements may also be obtained from the image data in the different 3-D echo imaging volumes which are collected to create the composite image represented by recorded image 2853. Further diagnostic information (e.g. measurements of cardiac electrical activity) may also be displayed on the recorded image 2853 in certain embodiments; the measurements of cardiac electrical activity may be obtained from an intraventricular catheter which includes an electrode at its distal tip for sensing and measuring cardiac electrical activity at points on the myocardium within the left ventricle. This intraventricular catheter may be the same as needle catheter 2852 or may be a different catheter used at a different time in the treatment or diagnostic procedures.

The recorded image 2853 also includes treatment information in the form of recorded injection positions, which are displayed at the positions of injections of a therapeutic agent (e.g. stem cells designed to become functional, healthy myocardium and/or angiogenesis agents or other types of therapeutic agents) into the myocardium of the left ventricle. A position of injection may be indicated to the system by an operator positioning a cursor, shown in the real time image 2851, on the recorded image at the position of an operator-controlled injection; alternatively, the operator may press a button to indicate that an injection just occurred at the distal end of the catheter 2852, which has a known position derived from the real time image 2851 which is overlaid (and aligned) onto the recorded image 2853. For example, the distal tip of the catheter 2852 is shown in both real time images 2851 and 2851A respectively in FIGS. 2B and 2C, and the position of this distal tip in the coordinate space of the 3-D echo imaging volume used to create real time image 2851 is known relative to the aligned coordinate space of the 3-D echo image volume used to create the recorded image 2853. While certain embodiments may use an intraventricular needle catheter to deliver, through an injection into the interior wall of the left ventricle, a therapeutic agent, it will be appreciated that alternative embodiments may use an ablation catheter (e.g. a laser ablation device at the distal end of the ablation catheter) or other types of treatment or diagnostic catheters. Such alternative catheters can be viewed in a real time image, such as real time image 2851, which is overlaid onto a recorded image, such as recorded image 2853, which is assembled from several previously recorded images.

The 90° view shown in FIG. 2C shows the recorded image 2853A, which is created from the same set of 3-D echo imaging volumes used to create recorded image 2853, at a different view than the view shown in FIG. 2B, and thus the same diagnostic information is shown on recorded image 2853 and on recorded image 2853A, but from a different point of view (a 0° view versus a 90° view). Similarly, the 90° view shown in FIG. 2C shows the real time image 2851A, which is created from the same 3-D echo imaging volume used to create real time image 2851, at a different view than the view shown in FIG. 2B, and thus the catheter 2852 is shown in real time image 2851A in the same position as in the real time image 2851.

A physician or other operator of a treatment catheter or diagnostic catheter may use a 3-D echo imaging probe to create the 3-D echo imaging volumes used to create the recorded image 2853, and may then insert the treatment catheter or diagnostic catheter while using a 3-D echo imaging probe to create a 3-D echo imaging volume used to create the real time image 2851. As the operator moves the catheter, the image of the catheter is revealed in the real time image, which is overlaid onto the recorded image 2853. In this way, the operator is provided with a real time (e.g. within the last image update) or near real time (e.g. within the last cardiac cycle) view of the catheter's distal region on a larger area or volume than is possible with a real time view.

In certain embodiments of a system which generates the images of FIGS. 2B and 2C, it may be desirable to use, for the purposes of generating displayed images, only image data (for both the recorded image, such as recorded image 2853, and the real time image, such as real time image 2851) from a predefined portion of the cardiac cycle where the heart is not rapidly moving (e.g. 400 msec. after the "R" wave, where the timing/delay after the "R" wave or some portion of the ECG waveform could be operator selectable) to record guide and operational information onto the recorded image as well as to compute information such as distances between injection sites. This provides a stable (e.g., nearly no motion) image for marking and for storing guide and operational information and allows the amount of time of almost an entire cardiac cycle for the image correlation process to obtain a near optimal (if not optimal) image alignment, based upon measurement and position accuracy. Also, a separate orthogonal pair of rapidly updated see-through images may be provided to show the real time position of the catheter in the anatomy.

Figure 3:
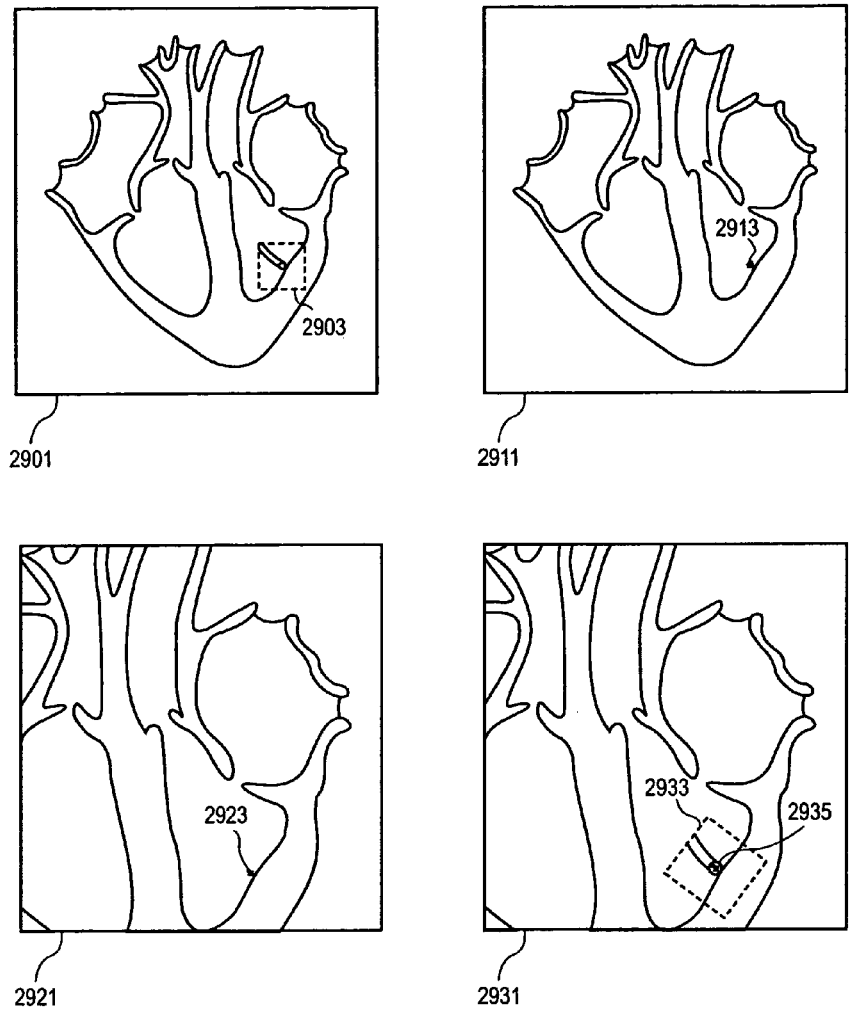
FIG. 3 illustrates examples of using real time images and pre-recorded images in a cardiac therapy procedure according to one embodiment of the present invention.

FIG. 3 illustrates examples of using real time images and pre-recorded images in a cardiac therapy procedure according to one embodiment of the present invention. Screen (2901) illustrates a scenario where a selectively clipped portion (2903) of the real time image (e.g., corresponding to portion 2813 of image 2811 in FIG. 2A) is overlain on the pre-recorded image. Screen (2911) illustrates a scenario where a representation (2913) of the medical device (e.g., the tip of the catheter) is overlain on the pre-recorded image. Screen (2921) illustrates a scenario where an enlarged portion of the pre-recorded image is shown with a representation (2923) of the medical device (e.g., the tip of the catheter) to illustrate the details near the point of interest. Screen (2931) illustrates a scenario where an enlarged portion is displayed with a selectively clipped portion (2933) of the real time image and a representation of the medical device (2935) (e.g., the tip of the catheter).

In one embodiment of the present invention, the location of the catheter tip is determined using the 3-D echo imaging system. After the operator identifies the catheter tip on the displayed real time image(s) from the 3-D echo image system (e.g., in two or more of representations of the 3-D views or two or more of the 2-D views from a 3-D volume) using a graphical user interface, the system determines the coordinates of the identified catheter tip in the real-time image coordinate system of the 3-D echo imaging system. The coordinates can then be converted to the coordinate system of the pre-recorded images.

For instance, a system according to one embodiment of the present invention is set-up to produce two differently oriented views of the same anatomy. There are two trackballs associated with both views, which allows the operator to move a pointer (e.g., a spot or other icon) in the same locations in both views. Preferably, one track ball would move the pointer in, say the X-Y plane and the second track ball would move the pointer in either the X-Z or the Y-Z planes. The trackballs move the pointers in different planes so that the movement of a pointer in the 3-D space is simulated. Preferably, the image orientations are such that one view is a projection of the 3-D image in one trackball plane and the other view is a projection in the other trackball plane and the trackball planes are orthogonal to each other. When the operator has used the trackballs to move the pointer such that the desired location in both views is under the pointer, the X, Y and Z coordinates of the desired location are determined. At this point, the operator may signal the 3-D echo imaging system to input the location in the desired manner (along with any other desired coding at that location). In this way, the operator can identify and/or record the location of the catheter tip from the 3-D echo images. The orientation of the catheter tip can be obtained through identifying another point near/just proximal of the catheter tip.

Figure 7:
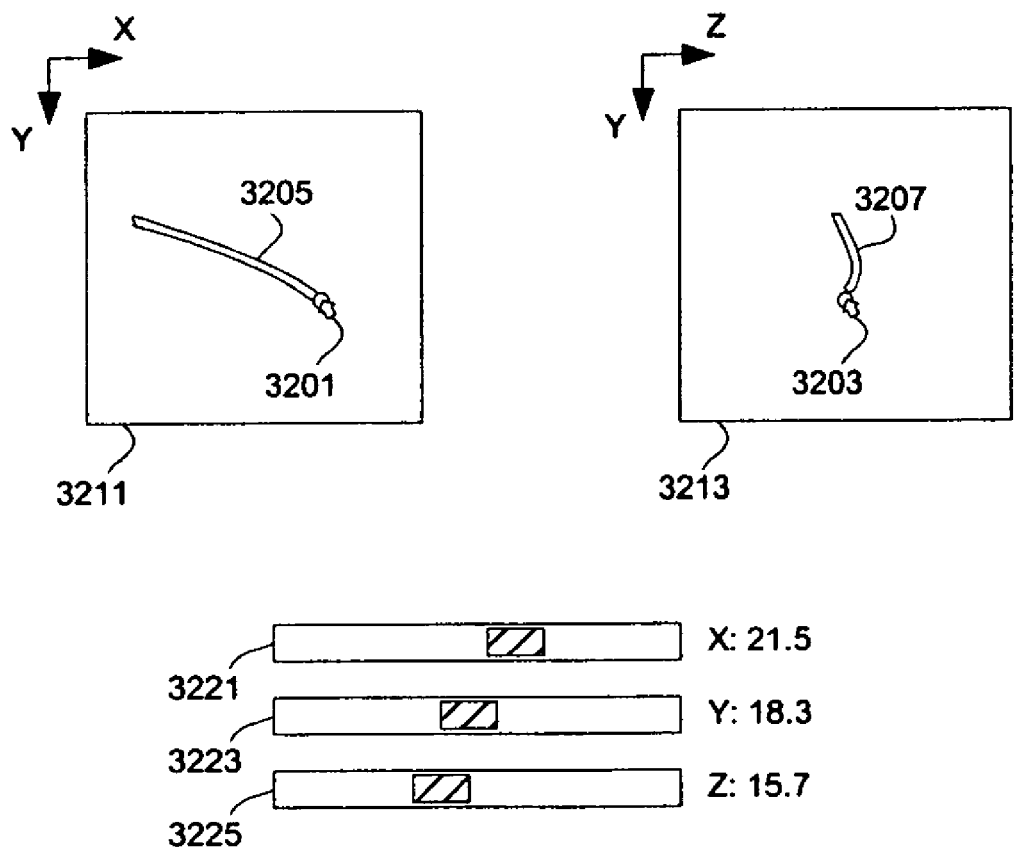
FIG. 7 illustrates a graphical user interface to identify a position of medical device using a 3-D image data set according to one embodiment of the present invention.

For example, FIG. 7 illustrates the cursors in two orthogonal view planes, X-Y plane viewing in the Z direction and Y-Z plane viewing in the opposite of the X direction in the 3-D image coordinate system X, Y and Z. A pointer in the 3-D space X-Y-Z is shown as the pointers (3201 and 3203) in the X-Y view (3211) and Y-Z view (3213) respectively. The sliders (3221, 3223, 3225) illustrate graphically the coordinates of the pointer in the 3-D space. The sliders can be individually adjusted to change the coordinates of the 3-D pointer, which causes the update of at least one of the positions of the pointers (3201 and 3203) in the X-Y view (3211) and Y-Z view (3213). The slides may be manually adjusted. In other embodiments, the cursor controlling device may be a device such as a mouse, trackball, touch pad, etc., or an input device that has 3 degrees of freedom, or a combination of input devices that have at least three degrees of freedom. In one embodiment, the graphical display of the sliders (3221, 3223, 3225) is optional.

When the pointers (3201 and 3203) in the X-Y view (3211) and Y-Z view (3213) coincide with the desired position in both the X-Y view (3211) and Y-Z view (3213), the 3-D position of the 3-D pointer can be taken as the position of the desired point (e.g., the tip of the catheter). Using the spatial/scaling alignment information obtained through image correlation, the 3-D position of the point can also be determined relative to the recorded image.

In one embodiment, the X-Y view (3211) and Y-Z view (3213) show the highlighted image of medical device obtained from subtracting the recorded image from the real time image (after the alignment) to cancel out the anatomy, as illustrated in FIG. 7. Alternatively, the 3-D pointer can be placed in the 3-D real time image to identify the point of interest. Alternatively, the 3-D pointer can be placed in the recorded image with the real time image superimposed on the recorded image.

In one embodiment, the device (e.g., catheter) tip and/or a portion of the device (injection needle) can be vibrated (rotated or otherwise moved) such that the ultrasonic pulses from the imaging probe that reflect off of them are Doppler shifted. Current 3-D echo imaging systems can detect such Doppler shift, as well as the location of the Doppler shifting element(s) of the device. In one embodiment of the present invention, the echo amplitudes of the Doppler shifted signals from the device elements is much greater than the Doppler shifted signals produced by the flowing blood. Thus, the system can automatically identify the catheter location. Such an approach has the advantage that the device (e.g., catheter) doesn't necessarily have to be connected to the 3-D echo imaging system. This eliminates a connection cable; the device becomes easier to manipulate; and more stringent electrical isolation and leakage current requirements are avoided.

In one embodiment, the globe shaped device (e.g., catheter) tip includes an omni-directional ultrasonic transducer and/or a band-like transducer. The transducer is mounted on the device's distal portion and electrically connected to the 3-D echo imaging system. The transducer(s) will receive the ultrasonic pulses from the 3-D echo imaging system's imaging probe, when in its ultrasonic transmit path. The delays between the time the imaging probe's transducers in its array transmit pulses and the time the pulses are received by device mounted transducer(s), together with the known physical positions of the imaging probe's array transducers, provides adequate information for the 3-D echo imaging system to compute the location of a particular catheter mounted transducer in the real-time image. This position can then be used to code that corresponding location either onto or modifying the recorded 3-D echo image data (or a portion of it) with the desired diagnostic or therapeutic (guide or operational) info in the desired manner.

In one less preferred embodiment, the device-mounted transducer(s) may send out an ultrasonic pulse, which is received by the 3-D echo imaging system's imaging probe. The delays between the time the device mounted transducer's transmits the pulse and the time the pulse is received by imaging probe's transducers in its array, together with the known physical positions of the imaging probe's array transducers, provides adequate information for the 3-D echo imaging system to compute the location of a particular catheter mounted transducer in the real-time image. This embodiment is less preferred because the time allotted to transmit the pulse from the catheter to the probe reduces the time available for real-time imaging.

The above methods for location and/or orientation determination can also be used in combination. For example, the positions determined from different methods can be averaged to improve the accuracy and the ease of use.

In one example system, a 3-D TTE, TEE or ICE system contains the means to determine the 3-D location and orientation of the echo probe. Any means known in the art, including ultrasonic, electromagnetic, gravimetric, magnetic and/or mechanical means, can be used. With the determination of the probe's 3-D location and orientation, the 3-D image matrix created from the echo data may be referenced to a fixed external coordinate system, the coordinate system of a previous image or an internally generated coordinate system (such as a modified coordinate system designed to keep the stored image data within a defined memory volume). Thus, as long as the location and orientation of the patient is kept constant, determined or known, the 3-D echo images made from different positions of the probe can be assembled to produce a more complete picture of the anatomy.

In one embodiment, the probe's 3-D location and orientation are used as a starting point to search for better image alignment through comparing and matching imaging information in overlapping regions of the real-time image and the recorded image. For example, the probe's position is used as a starting point in a mathematical correlation process. Thus, the change in the position and orientation of the patient can be automatically compensated in assembling the more complete picture of the anatomy.

Such an approach is especially beneficial for an ultrasonic imaging system that is typically used to image the heart. For instance, in many patients, only portions of the heart can be imaged by the TTE probe at locations between various ribs and under the rib cage. In this system, all of these images can be assembled to construct a complete or a more complete 3-D image of the heart. The images are collected and stored based on their relationship with the patient's ECG. TEE and ICE systems suffer from similar limitations. Some currently available 3-D TTE and TEE systems collect ECG data or have an ECG input terminal. Thus, the assembled images may be replayed in time with the recorded ECG or with minor modifications, in synchrony with the patient's real-time ECG. The operator may choose which image sequences to assemble and store for use.

In one embodiment, an image correlation process, based on comparing and matching imaging information, can be used to improve the alignment solution of the 3-D location and orientation tracking system or to replace the tracking system.

In one embodiment, only a portion of a 3-D location and orientation tracking system is used and an image correlation process, based on comparing and matching imaging information, is used to improve the alignment solution of the location and/or orientation information provided by the 3-D location and orientation tracking system and to generate the location and/or orientation information not provided by the 3-D location and orientation tracking system. Such a partial system as this may improve the speed and quality of the comparing and matching of imaging information while not requiring a relatively complex and expensive 3-D location and orientation tracking system that provides tracking in all 6 degrees of freedom.

One additional useful image manipulation function is a tool (or a display format) to create or provide the orthogonal point of view image display (copy) of the currently manipulated image that would continue to be automatically manipulated in the same manner as its parent image and continues to show what the parent image looks like from an orthogonal viewpoint. Since there are always 4 orthogonal views to any see-through or surface image display, the operator should be able to select between them in the new view. Orthogonal 3-D see-through and/or 3-D surface image pair displays facilitate the 3-D visualization/comprehension of the anatomy and the device location/orientation in the anatomy by the operator. Another operation is to use the previously discussed trackball/other device system with orthogonal views to mark the manipulated/recorded image with location/area/volume specific operational and/or guide information. In one scenario according to one embodiment of the present invention, just prior to treatment, the system is used to create the baseline image matrix of the patient's left ventricle. The image matrix data for the ECG loop can be processed for display after being adjusted, copied, cropped, split, rotated, re-positioned, size adjusted, etc. to provide good views of the interior of the left ventricle. A graphical user interface is provided to allow the user to perform the image manipulations, such as cropping, copying, splitting, rotating, shifting, sizing, annotating, etc. Further, the manipulations may include combining multiple views into one view, such as taking a portion of one view and superimposed it on another view at a selected location.

In one embodiment, the parameters for cropping, copying, splitting, rotating, re-positioning, size adjusting, etc., are recorded so that good or desired views of the interior of the left ventricle can be reconstructed directly from the image matrix and the recorded parameters. When the real time information is available, the recorded parameters can be used to operate on an image set that includes the real time information. The real time information may include the real time image, or the information derived from the real time image, or real time location and/or orientation information of the medical device (e.g., determined through automatic pattern recognition, through a 3-D pointer in the real time imaging space, through Doppler based detection, through a computation based on ultrasound propagation delay, etc.).

Figure 8:
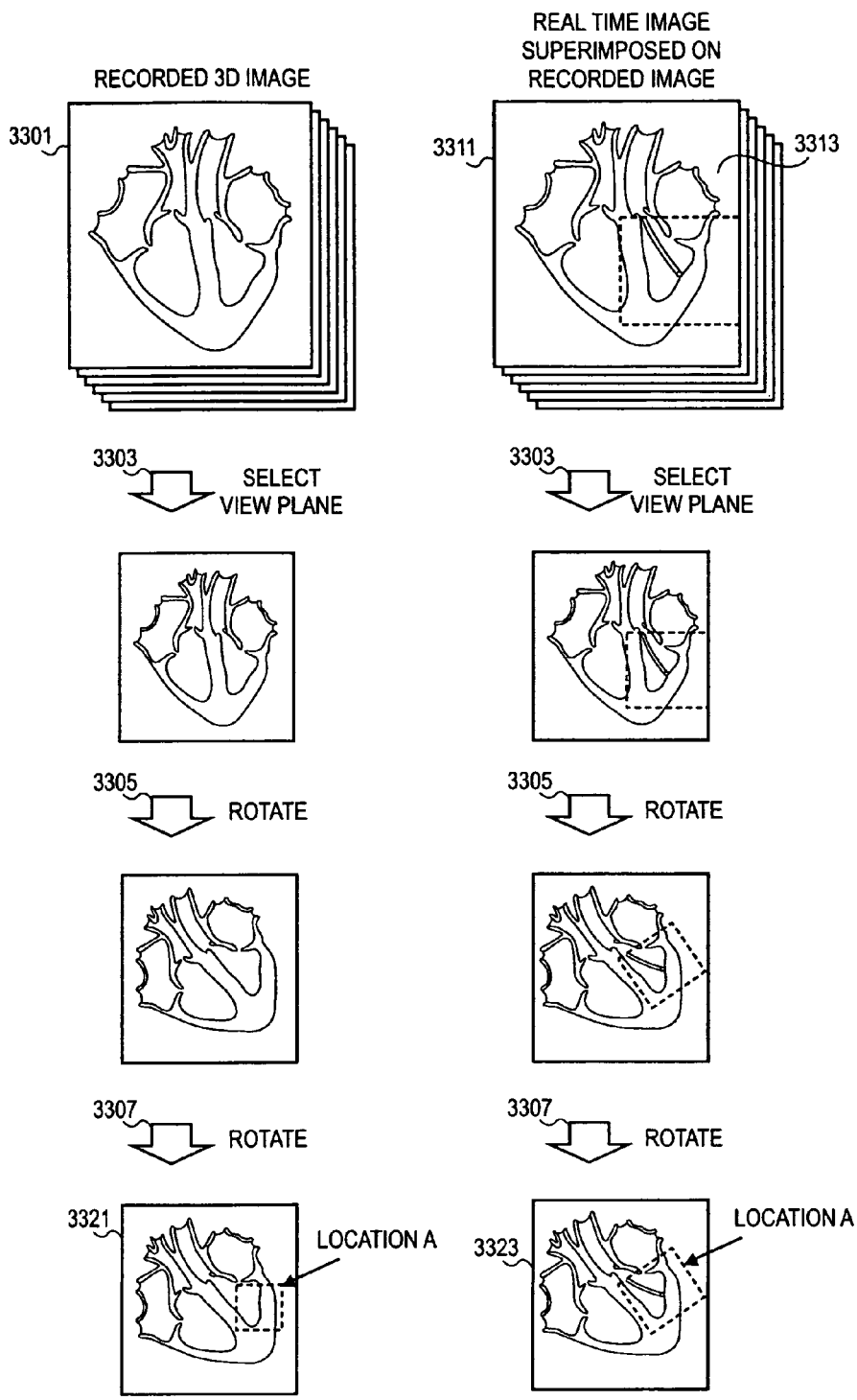
FIG. 8 illustrates an example to plan image manipulations according to one embodiment of the present invention.

For example, in FIG. 8, the recorded 3-D image (3301) can be used to plan a set of image manipulations, such as selecting a view plane (3303), rotating (3305) and annotating (3307), to reach a desirable view (3321) of the recorded 3-D image. The embodiment of FIG. 8 may use 3-D echo imaging systems to create images from 3-D imaging volumes. In order to use less complex drawings, 2-D image slices of these 3-D imaging volumes are shown in FIG. 8, and the fan-like shape of the slices and volumes has been omitted. The sequence of operations (e.g., 3303, 3305, and 3307) can then be stored as a script (e.g., a string of parameters associated with a sequence of identifiers of the corresponding operations). After the real time image (3313) is aligned with the recorded image (3301), the real time image can be superimposed on the recorded image to form the combined image (3311). The operation to combine the images can be performed before a view plane is selected to form the combined 3-D image, or performed only in the selected view plane to form the selected combined 2-D view.

The stored sequence of operations (e.g., 3303, 3305 and 3307) can be applied to the combined imaging information to generate the desired real time view (3323) for an image guided medical procedure. Once the desired view is displayed, the user may further modify the view through further manipulations, the sequence of which can also be recorded for later review.

In one embodiment, multiple instances of manipulation sequences can be recorded independent of image data; and the user interface provides options for the selection of one from the multiple instances, which can then be used to manipulate image data from a number of different patients.

In one embodiment, a sequence of manipulation provides only one view. Alternatively, a sequence of manipulations may provide multiple views, each of which is to be displayed for a user selectable amount of time, time in the cardiac cycle and/or repeating change in viewpoint (e.g., image rotation or rocking back and forth through a range of angles), so that a display according to the sequence of manipulations provides a desired level of animation of a set of desired views of the 3-D image or 3-D image pairs (a set of orthogonal views) and thus, provide a sense of the 3-D image relationships despite the 2-D nature of a display monitor and/or limit the anatomical motion (e.g. cardiac cycle heart wall motion).

The recorded image matrix data for the ECG loop can also be processed for the display to show the left ventricle color-coded or otherwise marked for its amplitude of wall motion. For example, above a certain amount of wall motion within the ECG loop, the heart muscle is considered healthy. Below that amount of wall motion (e.g., wall motion in the opposite direction to that of contracting tissue in systole may indicate recently dead tissue, reduced wall motion may indicate scar tissue, asynchronous wall motion may indicate a contraction wave conduction problem), the heart muscle is considered to be either stunned, dead or having been replaced by scar tissue. The recorded image matrix data for the ECG loop can also be processed in a similar manner to indicate wall thickness. In one embodiment, the actual data in the recorded image data matrix is untouched; only the processing of the data for display purposes is adjusted. In one embodiment, the operational and/or guide data are stored separated with reference to the coordinate system of the image matrix data so that the operational and/or guide information can be selectively displayed over the images of the heart. In one embodiment, the operator/system identifies the locations, areas or volumes on the images to record and save the operational and/or guide information for later use. Further, in one embodiment of the present invention, the operator selectively arranges and records a plurality of viewpoints and scales for visualization of the left ventricle. The stored viewpoints and scales for visualization can be recalled for guidance.

Then, the needle catheter with an echo compatible tip and tip electrode, which may also have a more proximal electrode(s), is inserted into the left ventricle in the normal manner and positioned in the left ventricle for an injection. An echo probe is used to locate the tip of the catheter in the left ventricle. The system is set to a mode where the real-time image is processed and then combined, overlaid or alternated on the display with the baseline (recorded) image matrix (the recorded image(s) and/or assembled and/or manipulated and/or labeled images of the heart, such as recorded image 2853), which is also processed in synchrony with the patient's ECG. The guide or operational information can also be selectively displayed over the images. The operator may update or adjust the guide or operational information as desired; and guide or operational information can be continued to be applied to both the real-time image data and/or the baseline (recorded) image matrix. Thus, when the tip of the catheter is located (e.g., through visualization and identification on the real-time portion of the display), its position relative to the left ventricle anatomy is immediately recognizable. If the ECG from the tip electrode is a high amplitude and on a portion of the left ventricle with below a certain amount of synchronous wall motion, then that location may be determined to be a location of stunned tissue (border zone). If the ECG from the tip electrode is a low amplitude and on a portion of the left ventricle with asynchronous or below a certain amount of wall motion, then that location may be determined to be a location of dead or scar tissue. Thus, the data required for diagnosing the tissue at the current potential injection location in the left ventricle as either healthy, stunned or dead/scarred and either too thick, normal or too thin is presented to the operator. The operator may then record the diagnosis in relation with the baseline (recorded) image matrix in various manners (e.g. as shown in the recorded image 2853 shown in FIG. 2B), although it is preferred that the diagnosis code be visible on the display or visible on another display and not interfere with treatment that is required and the visualization of the orientation/location of the catheter; then, an injection/treatment may be made and recorded in relation with the baseline (recorded) image matrix. The location and/or orientation of the catheter may be adjusted; and the process repeated. After one treatment location is recorded, the system may automatically compare the current diagnosis location with previous treatment locations and provide the operator with the distance(s) to the nearest previous treatment location (s). Thus the treatment may be guided and applied more evenly over the target tissues for spatial dose control.

Although the above example scenario is aimed at the internal surface of the left ventricle, it is noted that the process can also be applied to any chamber, structure or surface of the heart or other organs. When imaging other organs, ECG recording/synchrony may not be required. However, for some organs, like the heart, a further refinement can be made to also record in synchrony with respiration or to control or limit respiration to minimize its effects, especially in systems where the image correlation functions are absent or limited in their effectiveness.

Also, although the above example scenario has focused on 3-D echocardiogram imaging in general, the process may be applied to other ultrasonic modalities that may be available to provide 3-D imaging capabilities. When a TEE ultrasonic modality is used, the 3-D location and orientation determination of the probe may be omitted, if the position of the probe in the esophagus is adequately fixed and provides an adequate view of the entire region of interest. In such a case, the range of the search of the spatial offsets during the image correlation process may be limited enough to provide for the desired speed and quality of an image correlation.

When TTE is used, the patient is generally not heavily anesthetized. A technician can operate the echo system during the treatment; and TTE can generate adequate images on many (e.g., 80-85%) patients.

When TEE is used, the patient is often heavily sedated to endure the discomfort of the probe in the throat. Typically, a trained physician is to insert and position the TEE probe. TEE generally provides images with better quality than TTE; and TEE can generate adequate images in almost all patients. TEE can be used when TTE cannot provide adequate images for the patients because of the anatomy of the patients or because of a higher image quality is required for more accurate and precise device guidance.

ICE involves the insertion of the probe into the venous system. The ICE probe is to be operated by a physician and positioned in the right heart. Typically, a cutdown of the jugular vein is made to insert the ICE probe; and the patient may be anesthetized at a level similar to that of TTE guided catheter-based procedures. ICE can provide excellent image quality and adequate images for almost all patients. Since ICE probes are made smaller to allow blood vessel insertion, the field of view of ICE probes is typically more limited than TTE and TEE probes. ICE has a higher per-use cost, since the ICE probes are typically not re-used (e.g., cleaned or re-sterilized) after having been in contact with blood.

In general, ultrasound based imaging systems are less expensive than other types of imaging systems, such as X-ray or gamma ray based system (e.g., CT, EBCT, multi-axis fluoro, etc.) or MRI based system. Ultrasound based systems are portable to the Cath Lab; and Cardiologists are familiar with the equipment and the interpretation of the obtained images. Ultrasound based imaging systems have no un-addressed safety issues.

Alternatively, X-ray or gamma ray based system (e.g., CT, EBCT, multi-axis fluoro, etc.) can be used with the various embodiments described herein, although such imaging systems have the disadvantage of radiation exposure, especially to the operator(s), and high cost. Such systems are generally not available in the Cath Lab.

Alternatively, MRI based systems can be used with the various embodiments described herein, although such imaging systems have the disadvantage of high cost. There is no widespread availability of such systems in Cath Lab. Typical MRI systems require special device material and designs, some of which increase device size and adversely affect device function.

In one embodiment of the present invention, a catheter has features designed to improve the images obtained from 3-D echo (ultrasound) imaging systems. Some of the features are described below and shown in FIGS. 14-27.

Figure 4:
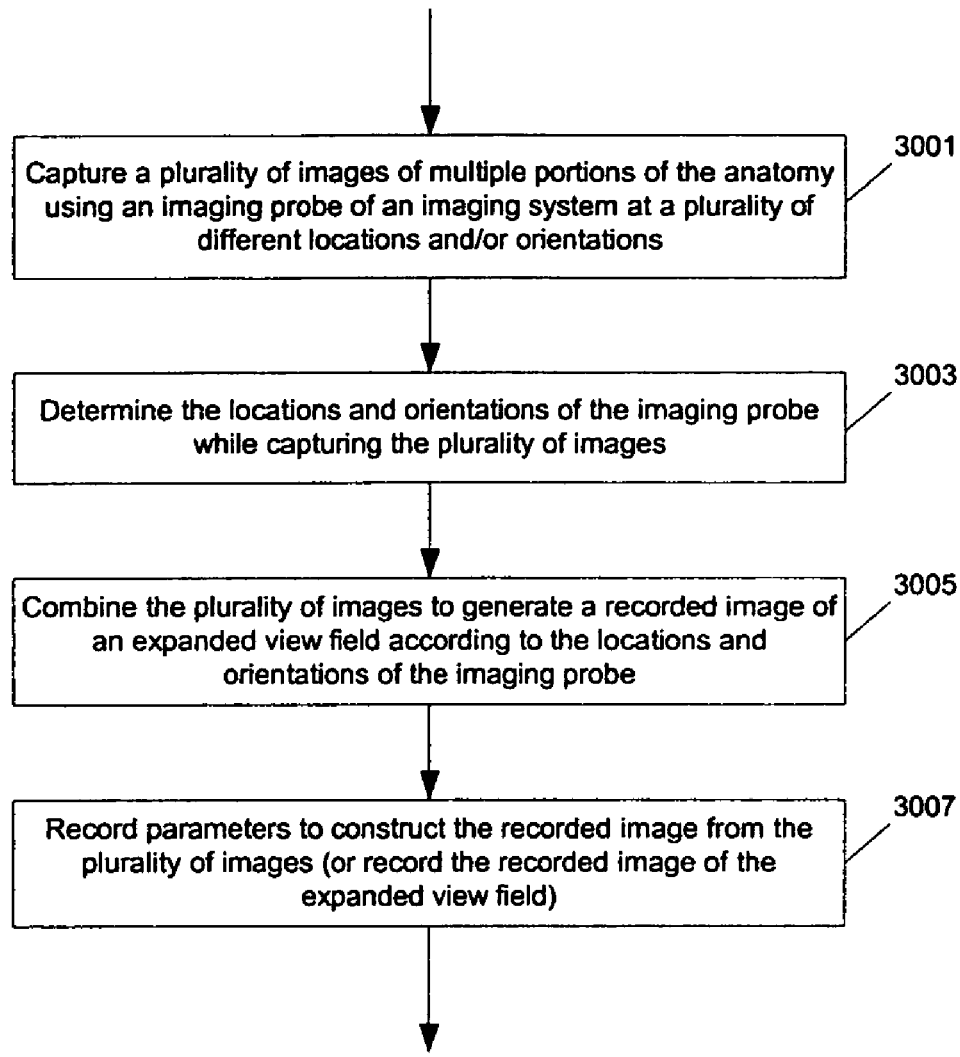
FIG. 4 illustrates a flow diagram of a method to prepare images for guidance during a percutaneous procedure according to one embodiment of the present invention.

FIG. 4 illustrates a flow diagram of a method to prepare images for guidance during a percutaneous procedure according to one embodiment of the present invention. The embodiment shown in FIG. 4 assumes the use of a 3-D echo imaging system to create an expanded (composite) recorded image, such as the recorded image 2853 of FIG. 2B. In FIG. 4, operation 3001 captures a plurality of images of multiple portions of the anatomy using an imaging probe of an imaging system at a plurality of different locations and/or orientations either relative to the patient or relative to the imaging probe.

Operation 3003 determines the locations and orientations of the imaging probe while capturing the plurality of images. Operation 3005 combines the plurality of images to generate a recorded image of an expanded view field according to the locations and orientations of the imaging probe.

Alternatively or in addition, the system may automatically match the overlapping regions to determine the relative location and orientation of the images with respect to each other. Alternatively or in addition, an operator may rotate, scale, move the images with respect to each other to reconstruct a large view of the anatomy from the small views of the captured images and/or provide a starting point for the system to automatically match the overlapping regions to determine the relative location and orientation of the images with respect to each other.

Operation 3007 records parameters to construct the recorded image from the plurality of images (or records the recorded image of the expanded view field).

In one embodiment of the present invention, the anatomy includes a moving organ, such as a heart, which have time-dependent states. One or more parameters, such as ECG, are used to index the images so that the images can be played back in real time according to real time measurements of the parameters.

Figure 5:
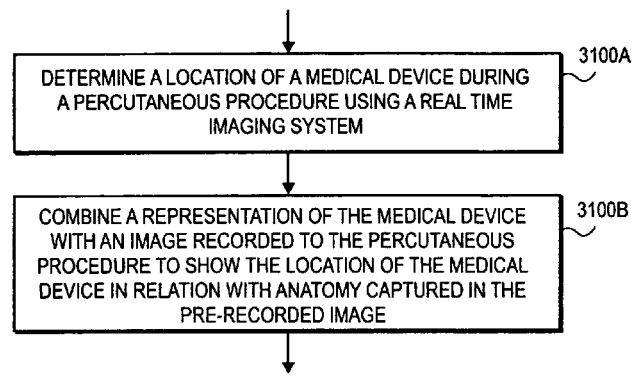
FIG. 5 illustrates a flow diagram of a method to guide a percutaneous procedure according to one embodiment of the present invention.

FIG. 5 illustrates a flow diagram of a method to guide a percutaneous procedure according to one embodiment of the present invention. In FIG. 5, operation 3100A determines a location of a medical device during a percutaneous procedure using a real time imaging system. Operation 3100B combines a representation of the medical device with an image recorded prior to the percutaneous procedure to show the location of the medical device in relation with anatomy captured in the pre-recorded image. The example of FIG. 2B shows such a representation of the medical device overlaid onto a recorded image.

In one embodiment, the real time imaging system is the same as the imaging system used to capture the pre-recorded images prior to the percutaneous procedure.

In one embodiment, the location of the medical device is determined through determining a three dimensional coordinate of the medical device from a graphical user interface showing images of the medical device captured by the real time imaging system. Alternatively, a portion of the medical device is vibrated to show a Doppler shifted portion; and the location of the medical device is determined through identifying the Doppler shifted portion of the medical device using the real time imaging system and computing coordinates of the location from the Doppler shifted portion. Alternatively, an ultrasound transducer(s) is mounted on the medical device (e.g., a tip portion of the catheter); and a delay(s) of ultrasonic pulse(s) between an imaging probe of the real time imaging system and the transducer(s) mounted on the medical device is measured and used to compute the coordinates of the location(s) of the transducer(s).

In one embodiment, at least a portion of a real time image captured from the real time imaging system is overlain on the recorded image. Alternatively, at least a portion of a real time image captured from the real time imaging system is blended with a corresponding portion of the recorded image to provide a translucent effect. Alternatively, at least a portion of a real time image captured from the real time imaging system and a corresponding portion of the recorded image are displayed in an alternating fashion. In one embodiment, an iconic representation of the medical device is overlain on the recorded image, with or without showing the real time image with the recorded image.

In one embodiment of the present invention, no position determination system is used for aligning images. Images are aligned according to automatic correlation between overlapping or common portions of the images. The correlation is determined automatically by a computer system.

In one embodiment, the real-time image data matrix and the guide/map (recorded or baseline) image data matrix are correlated with each other through varying their coordinate systems' spatial relationships. The spatial relationships, such as relative location and orientation and scale, can be varied continuously, intermittently or according to a search algorithm (e.g., a binary search) to find the highest correlation. The spatial relationships that provide the best correlation can be used to align the axes of the images. The correlation for alignment is performed for specific phases in the cardiac cycle (e.g., gated according to ECG). For example, images at the same or nearly the same time in the cardiac cycle can be aligned with each other; and alignments for different instances in the cardiac cycles are performed to obtain the alignment or to update the alignment for or during the entire cardiac cycle.

In one embodiment, spatial relationships for correlation at an image acquisition time in the cardiac cycle are used at only that point in the cardiac cycle. Alternatively, the spatial relationships determined by image correlation at an image acquisition time in the cardiac cycle are used as the starting point for image correlation at the next point in the cardiac cycle.

In one embodiment, only a portion of an image is used to calculate the correlation to reduce the volume or the computations involved and the processing time. For example, the image data may be truncated to only include the image data that encompasses the relevant anatomy. In the real time image, a portion of the image that includes the features that are not present in the recorded guide images, such as the catheter, can be excluded from the correlation operation. In one embodiment, an operator specifies the excluded region (e.g., on a graphical user interface that allows the operator to defined a region through a cursor controlling device, such as drawing a bounding box of the area). Alternatively, the system automatically identifies a point or a plurality of points of the device (e.g., through identifying Doppler shifted point(s) in the images which are produced through introducing vibrations at the corresponding point(s) of the device); and the system then automatically excludes a region based on the point or plurality of points.

In one embodiment, the image data between desired spatial intervals may be omitted based on the desired degree of axes alignment accuracy. For example, if the alignment accuracy is desired to be with 1 mm, the image data at 0.5 mm spatial grid intervals will be more than adequate to produce the desired alignment accuracy. Thus, the resolution of the image may be reduced for the purpose of alignment and thus the amount of image data to be processed may be reduced.

In one embodiment, judiciously selected separate lines, volumes and/or planes of the real time image are used correlate to the guide/map (recorded) image data to produce an adequate alignment. In one embodiment, the compared image data (e.g., to be evaluated by the correlation process) is a processed subset of image data matrices, such as surface image data matrices, gain adjusted image matrices, etc.

In one embodiment, a user interface is used to indicate a degree of correlation. For example, when there is an inadequate correlation (e.g., when a correlation value is lower than a threshold), due to an inadequate real-time image, rapid imaging probe /transducer motion or other factors, the user interface alerts the operator with a red light; and when the correlation is adequate, the user interface shows a green light. In one embodiment, when the correlation is poor, the marking of the locations on the image or other map is disabled. In one embodiment, when the correlation is poor, the real-time portion of the image overlay can change color or blink.

In one embodiment, the real-time image is blended with the (recorded) guide image to provide the appearance that the real-time image is transparent. In one embodiment, a blending factor is based on the degree of correlation. For example, the stronger the correlation is, the heavier the weight is for the real-time image over the guide image to emphasis the content of the real-time image (e.g., the presence of the catheter); the weaker the correlation is, the lighter the weight is for the real-time image over the guide image to wash out the content of the real-time image (e.g., the presence of the catheter) into the guide (recorded) image as background.

In one embodiment, diagnosis information (and/or other information, e.g., guide and operational information) is prepared and recorded based on the spatial relation in the guide (recorded) image, which is then mapped on the real time image according to the spatial correlation between the real time image and the guide (recorded) image. An example of how the diagnosis information, on the recorded image, is combined with the real time image is shown in FIGS. 2B and 2C. In one embodiment, the contrast of the mapped information with respect to the real time image is based on the degree of correlation between the real time image and the guide (recorded) image. For example, when the degree of correlation is improved, the contrast of the mapped information with respect to the real time image is enhanced to clearly show the mapped information; when the degree of correlation degrades, the contrast of the mapped information with respect to the real time image is reduced to indicate the increased uncertainty.

In one embodiment, the imaging modality (e.g., based on Ultrasound, MRI, CT, etc.) that is used to create the guide/map (recorded) images (such as recorded image 2853) is also used to capture the real-time image (such as real time image 2851) of the medical device (e.g., catheter) in the anatomy. In one embodiment, the imaging modality is set up such that the dimensional scales of the image data are the same or have a known (e.g., recorded) relationship. Thus, the computation for the scale correlation is simplified and correlation optimization and axes alignment can be performed more efficiently and rapidly. When the guide/map (recorded) images and the real-time images are not at the same dimensional scale, one or both are rescaled such that they have the same scale before axes alignment (and image(s) display) by correlation. Alternatively, the correlation process further includes the re-scaling factors as part of correlation formulation. Scaling can be done by interpolation in either direction on either set of image data and it is preferred that, if there is a scale difference, that the original image data is not overwritten (lost), but that a scaled recorded image data matrix for correlation and/or display purposes be created with the real-time image data's scale.

In one embodiment of the present invention, a user interface is provided for the operator to manually adjust the spatial correlation relationship for a particular instance of time within a cardiac cycle. The images are "frozen" in time temporally for the manual alignment. For example, the operator can use a cursor control device (e.g., a mouse, a trackball, a joystick, or keyboard) to move a temporal frame of a real-time 3-D image with respect to a corresponding temporal frame of guide/map (recorded) 3-D image to overlay the images on each other. Further, the operator may adjust the scaling when necessary to correlate the images. Once manually correlated using the user interface, the determined spatial correlation relationship can be used a starting point for a rapid, automatic search of correlation relationship for subsequent time instances. Alternately, the 3-D images are shown in synchronization with the patient's real-time ECG and the initial alignment is performed in a similar manner.

In one embodiment, when an ultrasound based imaging modality is used, the probe position used to collect the guide/map (recorded image) data may be configured to be the same or nearly the same as the probe position on the anatomy that is used to collect the real-time images. Such an arrangement allows the system to automatically select a close starting point for axes alignment and correlation. Such an arrangement also provides comparable image intensity to corresponding anatomy in each image data matrix for a rapid correlation optimization and axes alignment. When other types of imaging modalities area used (e.g., CT or MRI), the imaging axes of the map and real-time image data can be suitably constrained for rapid correlation optimization through limiting the patient's position on the bed/platform. Some of the currently available modalities provide such facility to constraint the patient on the same position on the bed/platform.

In one embodiment of the present invention, the imaging alignment methods are also used to correct the axes alignment as a result of gross heart motion in the thorax due to respiration or other patient motion/position change without the necessity of creating an image map (e.g. recorded image data) that is also gated to the respiration cycle and/or the detecting and recording of patient motion. Thus, this method provides a means to minimize the effects of respiration and other patient motion/position change on the accuracy of device location determinations in the anatomy, especially in the left heart, where chamber sizes are less affected by the respiratory cycle. Due to data collection/processing times, image matrix size and hardware complexity and limitations, gating image data to the respiration cycle and/or detecting and correcting for patient motion/position change, as well as gating to the ECG, can lead to a costly system in a therapeutic setting. Especially for right heart applications, the volumetric rate of respiration can be controlled or limited to limit the changes in pleural pressures that change the blood inflow rates to the right heart and thus result in size changes to the right heart chambers. Further, patient motion/position change can be limited to provide the most rapid initial correlation process.

In cases of large patient motion/position change, an initial axes alignment by the operator may be desirable or necessary to gain the first alignment rapidly and correctly. For instance, in one method, the recorded image map and the real-time image are displayed on the same screen together in synchrony with the patient's ECG using the same axis convention and are then moved separately by the operator (e.g., by using trackballs) to align and overlap them in a close to anatomically correct fashion. The position and orientation changes of the images by the operator provide the initial axes alignment correction factors (spatial offsets). The operator then activates the automatic correlation function of the system to vary these factors to obtain the highest correlation in the overlapping portions in the two image data matrices over the ECG cycle or for each real-time image collection. At the highest correlation, the two images will be in the most anatomically correct alignment. Subsequently, no operator input would be required, when the correlation computation is performed to update the axes correction factors at a speed sufficient to follow the applied motion.

In one embodiment of the present invention, the correlation methods described above are further used to accurately piece together 3-D images that share an image portion of the same anatomy. Thus, when an imaging modality captures a desired field of view in more than one image map to adequately image all of the relevant anatomy, the image maps can be combined to form one single 3-D guide/map (recorded) image (data matrix), when the image maps (recordings) have suitable overlapping portions that show the same anatomy. In one embodiment, the set of guide/map (recorded) images of limited views are pieced together to generate a single guide/map (recorded) image as a reference (baseline) for the real-time processing and operating to reduce the processing time. It is more convenient to view and manipulate the resulting documentation on a single guide/map (recorded) image than on multiple images of limited views. For instance, in one method, the two recorded images can be displayed on the same screen together stepping through their ECG timing using the same axis convention and then be moved separately by the operator (e.g., by using track-balls) to align and overlap them in a close to anatomically correct fashion. The location and orientation changes of the images by the operator provide the initial axes alignment correction factors. The operator then activates the automatic correlation function of the system to vary these factors to obtain the highest correlation in the overlapping portions in the two image data matrices over the ECG cycle. At the highest correlation, the two images will be in the most anatomically correct alignment. Correction factors that provide the best correlation for each part of the cardiac cycle (the same time in the cardiac cycle, e.g., equal time after "R" wave), for each portion of the cardiac cycle (the same time interval in the cardiac cycle, e.g., equal durations after equal times after the "R" wave) and/or for the entire cardiac cycle (e.g., the "R" to "R" wave time interval) are obtained.

In one embodiment, the axes alignment correction factors are calculated for each image in the cardiac cycle to help minimize any inaccuracies that may be introduced by respiratory, patient or imaging probe (if an Echo system) motion. A smoothing, data choosing or other type algorithm may then be applied to the overlap and adjacent areas of the two images to create the best image of the overlap and adjacent image areas and the resulting image data from the smoothed area and the remaining areas of the two images saved in a new image matrix, which is the combination of the two original data matrices with their axes aligned. If desired or necessary, additional image portions may be added to the combined image data matrix in the same manner. Thus a recorded image map of the relevant anatomy may be constructed from more than one recorded image.

Figure 6:
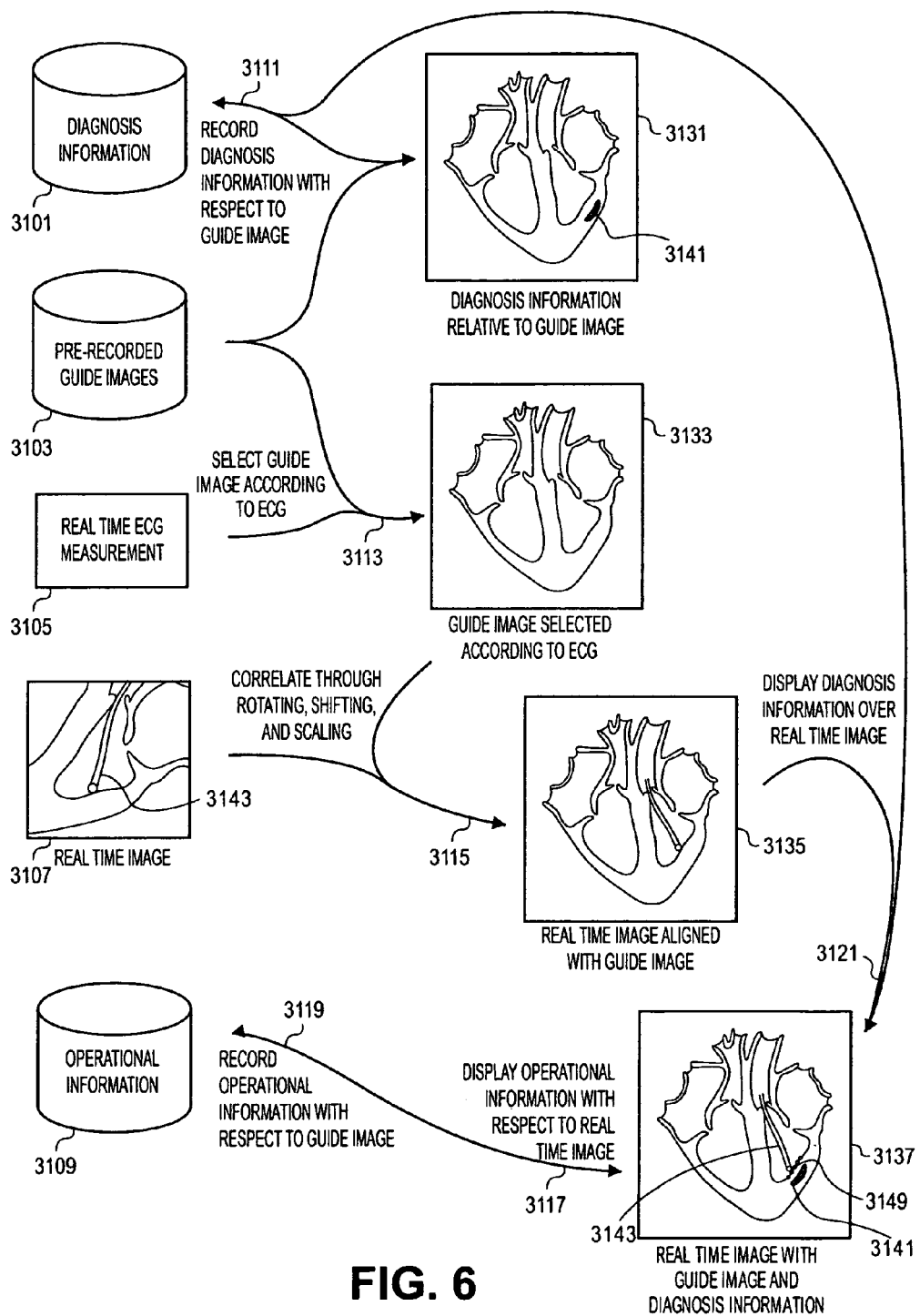
FIG. 6 illustrates the use of real time images and pre-recorded guide images according to one embodiment of the present invention.

FIG. 6 illustrates the use of real time images and recorded images according to one embodiment of the present invention.

In FIG. 6, recorded images (3103), which may be similar to recorded image 2853, are recorded before a percutaneous procedure using imaging modalities, which may be ultrasound based, X-ray or gamma ray based (e.g., CT), or MRI based. In one embodiment, an ultrasound based imaging modality is used, which can be TTE (transthoracic echocardiogram), TEE (transesophageal echocardiogram), or ICE (intracardiac echocardiogram).

In one embodiment, the imaging modality is capable of producing one or more sets of 3-D image information as the recorded guide images for a given position of the imaging probe. When a single set of 3-D image information does not have a field of view large enough for guiding the percutaneous procedure, more than one set of 3-D image information can be used. In one embodiment of the present invention, multiple sets of 3-D image information are taken from the same position of the imaging probe with respect to the patient. Alternatively, the multiple sets of 3-D image information can be taken from a number of different positions. In one embodiment of the present invention, a position determination system is used to track the location and orientation of the imaging probe to align the multiple sets of 3-D image information so that the multiple sets of 3-D image information can be combined into one set with a broad field view that substantially covers the union of the field views of the multiple sets. In one embodiment of the present invention, no position determination system is used to track the position and orientation of the imaging probe. Multiple sets of image information are generated to cover one or more overlapping regions; and the multiple sets of image information are correlated with each other through matching in the overlapping regions to provide one set of image information that has a broad field view covering a major portion of the union of the field views of the multiple sets. In one embodiment of the present invention, both the tracking of at least a portion of the location and orientation of the imaging probe and the correlation of overlapping regions are used to generate the set of image information with a broadened view.

In one embodiment of the present invention, the recorded guide images shows a heart of a patient, such as a recorded guide image 3131 which includes diagnosis information 3141; and different imaging information is collected for different phases in the cardiac cycle (e.g., as indicated by ECG measurement or timing).

In one embodiment of the present invention, at least a portion of the diagnosis information (3101) is generated with respect to the recorded guide images before the percutaneous procedure. For example, portions of heart muscle that are considered to be contracting properly or not contracting properly (e.g., the region shown by diagnosis information 3141) are shown in the recorded guide images such as the recorded guide image 3131. The recorded image 2853 in FIG. 2B also shows an example of such portions.

In one embodiment, the diagnosis information is recorded (in operation 3111) with respect to the guide (recorded) image. In one embodiment, the diagnosis information (3101) is stored separate from the guide images (3103); and the spatial relations of the diagnosis information (3101) are also stored so that the diagnosis information (3101) can be overlaid on the guide images (3103) when needed. Alternatively, a separate set of guide images with the diagnosis information can be prepared.

In one embodiment, the real time ECG measurement (3105) is used to select (in operation 3113) the corresponding guide (recorded) image (3133) for real time guidance during the percutaneous procedure. For example, real time ECG measurements may be used to time when to capture each of the recorded guide images.

In one embodiment, real time images (e.g., 3107), such as the real or near real time image 2851 in FIG. 2B, are also collected during the percutaneous procedure to show the position of the medical device (e.g., catheter 3143) with respect to the anatomy of the patient. In one embodiment, the real time imaging modality is the same, or of the same type, as the imaging modality used to capture the recorded guide images (e.g., using an ultrasound based system). Alternatively, the different types of imaging modalities can be used to scan the real time images and guide images.

In one embodiment, the real time image (3107) is correlated (through operation 3115) through rotating, shifting, and/or scaling to the guide (recorded) image (3133) selected according to real time ECG measurement to create a combined image (such as images 3135 and 3137) of the real time image overlaid and aligned to the guide (recorded) image, such as guide (recorded) image 3133. This correlation typically uses a computer to automatically and mathematically process the two sets of image data, and a mathematically based formula may be used, as part of this process, to produce a result that can be interpreted as a measure of similarity between the sets of image data (or processed image data). Many such formulas, ranging from as simple as the sum of data value differences at each data spatial location to complex comparison formulas, are known in the art. A "search" is typically part of the mathematical process, and the search usually involves a systematic variation in the test location and orientation offsets of one data set relative to another data set. With each variation, a correlation value may be determined in the spatially overlapping data and compared to previous correlation values from other test locations and orientations. Many search methods are known in the art and may include topological mapping.

In one embodiment, no position determination system is used to determine the location and orientation of the real time imaging probe for correlating the real time image with the guide (recorded) image. For example, a data processing system can be used to correlate the images according to the matching of the portions of the images of the same anatomy. The real time image typically may include one or more objects, which are not present in the guide (recorded) images (e.g., the image of the catheter 3143). Such portions of the real time images may not be helpful in the correlation process. In one embodiment, such portions of the real time images are excluded from the correlation computation. For example, one or more regions of the current real time image (3107) which do not include the image of the catheter 3143 can be selected for the correlation computation.

In one embodiment, the real time imaging modality and the imaging modality for the guide images are set up to have a known dimensional relations for the images generated. Thus, a correlation process can use the known dimensional relations for scaling the images for alignment of coordinate axes. Alternatively, the dimensional relations can also be varied to determine the best correlation.

In one embodiment of the present invention, the real time image (3107) has a smaller field of view than the guide (recorded) images. The real time image (3107) is overlaid on the guide image (3133) that is selected according to the real time ECG measurement to show the catheter 3143 in a broad field of view. This is similar to the relationship between real time image 2851 and the recorded image 2853.

Alternatively, a position determination system is used to determine the locations and/or orientations of imaging probes so that the real time images and the guide images can be correlated with each other according to the location and orientation or changes in the location and orientation of the imaging probes. Alternatively, the correlation/alignment process may be based on a combination of the locations and/or orientations of imaging probes and the matching of overlapping regions.

In one embodiment, when the spatial relation between the real time image and the pre-recorded guide image is determined, guide information and diagnostic information stored with respect to the guide images can be overlaid on the real time image. For example, the image (3137) shows the catheter (3143) according to the real time image (3107), a portion of heart muscle that is considered to be abnormal (3141) (e.g., stunned or dead, or having been replaced by scar tissue), and locations (e.g., needle injection locations 3149) where treatment is performed or to be performed.

In one embodiment, the guide information includes the diagnosis information (3101) which can be displayed (through operation 3121) on the real time image, the operational information (3109), such as locations of treatment, which can be displayed (through operation 3117) with respect to the real time image, and the guide image which is selected according to the real time ECG measurement.

In one embodiment, during the percutaneous procedure, further diagnosis information and/or operational information can be identified in view of the display of the real time image and recorded (such as in operations 3111 and 3119) with respect to the guide image. Thus, after the percutaneous procedure, the diagnosis information and/or operational information can be played back over the guide image for review.

In one embodiment, the real time images obtained during the percutaneous procedure are recorded with the corresponding spatial relations that are determined for alignment with the guide images. After the percutaneous procedure, these images can be played back for view.

Figure 9:
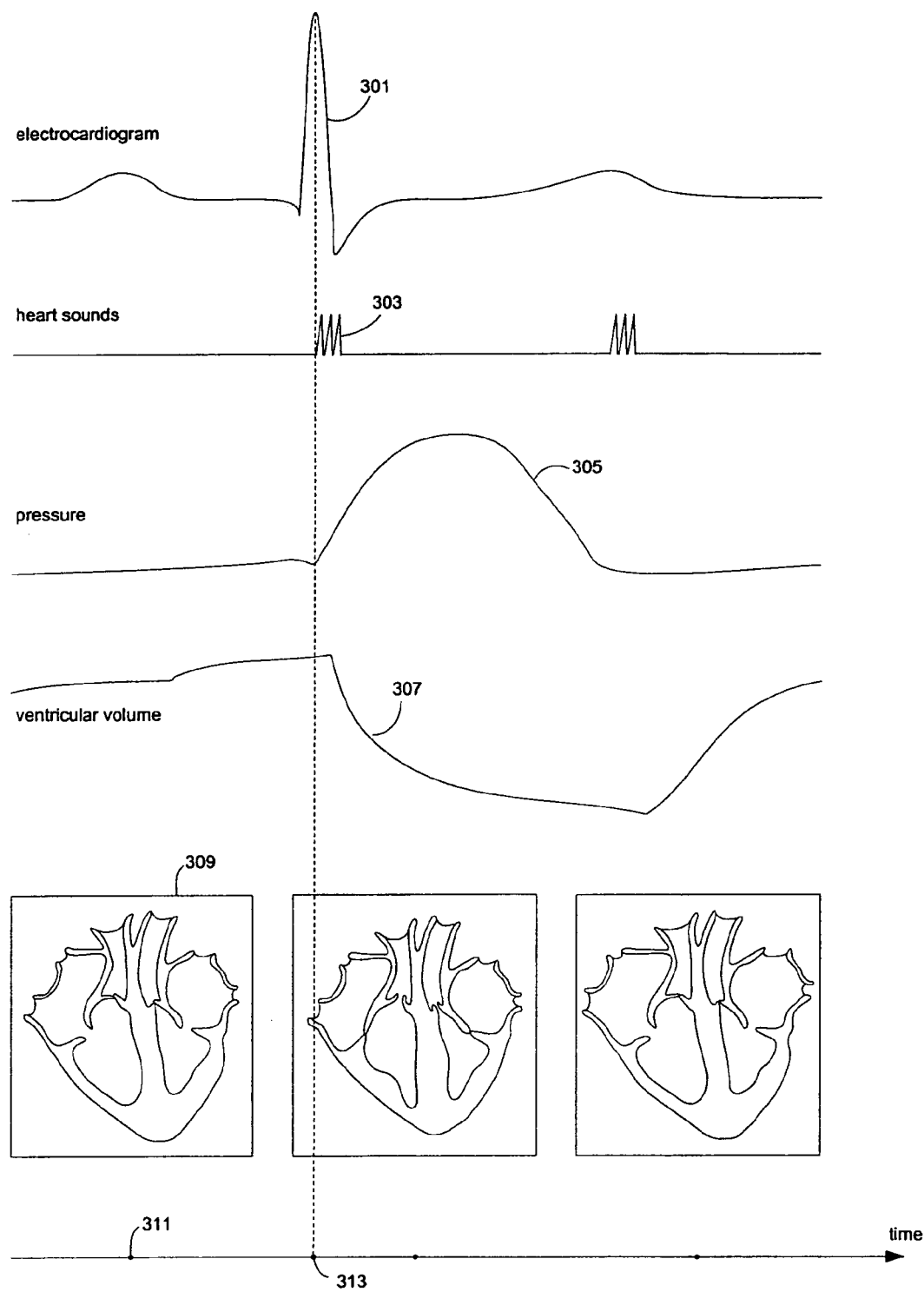
FIG. 9 illustrates various methods to prepare moving images for guiding real time position tracking according to embodiments of the present invention.

FIG. 9 illustrates various methods to prepare moving images for guiding real time position tracking according to embodiments of the present invention. According to one embodiment of the present invention, the images obtained at various instances in the cardiac cycle are associated with the time after a specific feature of the cycle, indicated by a parameter. For example, electrocardiogram 301 can be taken concurrently with the process of scanning the patient for the cardiac images (e.g., image 309). From comparing the timing of the occurrence of the specific feature (e.g., "R" wave at time 313 and the timing of the image generation (e.g., time 311 for image 309), the images of the heart can be correlated with the instances of time after the occurrence of the specific feature (e.g., "R" wave).

When the heart rate is not arrhythmic and doesn't vary greatly during the scanning process, images obtained from multiple cycles can be mapped into various instances in a single cycle, relative to the specific feature. The heart is at its most repeatable positions based on the time of ventricular contraction (time after ECG "R" wave or at end systole for ventricular imaging or time before "R" wave for atrial imaging). When the heart rate is not arrhythmic, but varies greatly during the scanning process, different single cycles may be created for individual heart rate ranges. This may require several scanning processes to fully collect the desired imaging data, but may be necessary for patients with unstable heart rates. However, in the case of arrhythmia (e.g. a PVC, Premature Ventricular Contraction), the images collected in this period can be discarded, as well as the images from the next cardiac cycle. After the heart recovers and returns to a more normal contraction/motion, the positions of the heart will be more repeatable.

Other cardiac parameters (e.g., heart sounds 303, pressure 305, ventricular volume 307, and others) can also be used to gate the cardiac images. For example, pulmonary artery pressure can be used at least as one of the parameters to correlate with the recorded images. The flow-directed balloon-tipped pulmonary artery (PA) catheter, also known as the Swan-Ganz catheter (SGC), has been in widespread clinical use for almost 30 years. Initially developed for cardiac output management of cardiac patients, it now has widespread use in the management of a variety of critical illnesses and surgical procedures. Anesthesiologists typically use it to monitor the condition of their patients during surgery. It is usually used to measure: cardiac output, pulmonary artery pressures and pulmonary wedge pressure (about the same pressure that would be measured in the left atrium). Examples of discussions related to Swan-Ganz catheters can be found in: J. Thorac Cardiovasc Surg, vol. 71, no. 2, 250-252, 1976; Cardiovasc Clin, vol. 8, no. 1, 103-111, 1977; and, Clin Orthop, no. 396, 142-151, 2002.

Further, other parameters that characterizing the state of the heart can also be used for gating the playback of the pre-recorded images. For example, relative wall motions of a heart can be measured in a CT or MR imaging system to correlate with the state of the heart. Real time relative wall motion can be determined using a 3-D position determination system (e.g., by keeping the mapping catheter tip in contact with the wall of the heart). Thus, the pre-recorded images can be played back according to the wall movement of the heart.

In one embodiment of the present invention, images obtained from one or more cycles with the concurrently measured cardiac parameters are used to construct a mapping between a measured cardiac parameter and the cardiac images. For example, the images can be correlated to the ECG level or feature(e.g., for a specific portion of the cardiac cycle); thus, a measured ECG level or feature can be used to determine the corresponding cardiac image. In one embodiment of the present invention, a cardiac cycle is divided into a number of segments, according the features (e.g., the occurrence of maximum and/or minimum points, etc.) so that the time can be benchmarked for each segment individually; and, within each segment, different cardiac images can be constructed as functions of the timing of one or more cardiac parameters. In one embodiment, image scanning is initiated based on the timing of one or more cardiac parameters, such that recorded and real-time images are collected at the same or at nearly the same desired times in the cardiac cycle.

In one embodiment of the present invention, the hemodynamic state of the patient is stable and similar during the imaging operation and during the therapy process so that the image selected or generated from the correlation between the measured cardiac parameters and the recorded images accurately represents the real time state of the heart. In such an embodiment, care is taken to ensure that the patient's hemodynamic state (e.g., blood pressure, heart rate, hydration state, blood volume, cardiac output, sedation state, ventilation state, respiration state, or others) during the 3-D imaging and during the therapy guidance is similar. For example, in both operations, the patient will be supine. Also, the patient is in similar sedation states; and, the time interval between imaging and therapy is minimized such that the disease state does not progress significantly (e.g., causing significant cardiac dimensional changes).

In another embodiment of the present invention, the imaging operation is performed for a number of different hemodynamic states (e.g., blood pressure, heart rate, hydration state, blood volume, sedation state, ventilation state, respiration state, or others) so that the recorded images can be selected or corrected (e.g., using an interpolation scheme) according to the real time hemodynamic state.

In a typical process to obtain diagnostic images, a patient is instructed to breathe shallowly or to hold the breath during an imaging run, since the chest movement can induce changes in the position and shape of the heart. According to one embodiment of the present invention, the patient's ventilation parameters and/or chest position/movement is also simultaneously monitored and recorded during the imaging run so that the cardiac images can be corrected or correlated with the breathing of the patient.

The quality of alignment in cardiac applications can be greatly improved by gating the reference point and/or orientation data relative to a time related cardiac parameter (such as the ECG or a blood pressure waveform) such that the reference points and/or orientations used are at the same or nearly at the same point in the cardiac cycle. Similarly, the quality of the alignment (as well as the location accuracy of the overlay) may be improved by gating the image data collections and the position/orientation data collections in a similar manner and to the same time related cardiac parameter. The quality of the alignment may also be improved by assuring that the hemodynamic state of the patient is relatively unchanged during the recording of the reference points and/or orientations by the imaging system and by the position determination system. Monitoring and controlling such parameters as the patient's blood pressure, heart rate, respiration, hydration state and sedation state can be used to improve the quality of the alignment. Simultaneously gating to a respiratory parameter, such as chest motion or to the cycle of a respirator (if used), and a cardiac parameter can further improve the quality of the alignment. Additionally, ensuring that the patient's hemodynamic and respiratory parameters are relatively the same during the imaging recording (e.g. to capture recorded images such as image 2853) and during the capturing of real-time images improves the location accuracy of the overlay.

Figure 10:
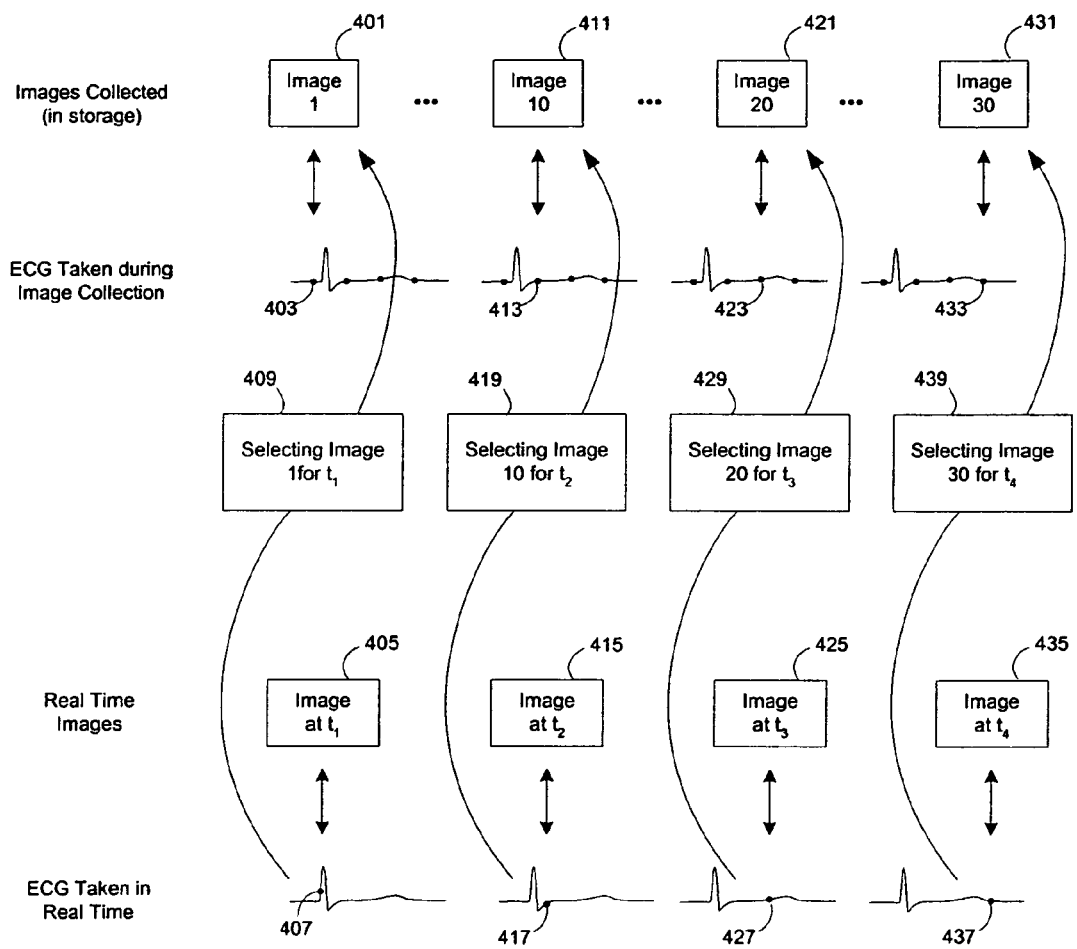

FIG. 10 illustrates a method to display real time images with corresponding recorded images according to one embodiment of the present invention. In FIG. 10, images 401, 411, 421 and 431 represent recorded 3-D images (e.g., from combining multiple sets of small field of view images into a large field of view images using a real time imaging modality, such as an echo or CT or MRI system). Data 403, 413, 423 and 433 represent the ECG taken during the collection of images 401, 411, 421 and 431, respectively, which may be used to create a composite recorded image (such as recorded image 2853). Real time images 405, 415, 425, 435 represent the images obtained at time $t_1$, $t_2$, $t_3$, and $t_4$ during the medical operation. Data 407, 417, 427 and 437 represent the ECG taken when the real time images 405, 415, 425 and 435 are obtained. The collected images (e.g., 401) are correlated to the ECG taken during image collection (e.g., 403). When a real time image (e.g., 405) is obtained and ECG (e.g., 407) is taken substantially contemporaneously with that real time image, that ECG may be matched with the closest ECG taken during the collection of images in order to select the recorded image which most closely resembles the phase of the heart in its cardiac cycle based upon the real time ECG. In one embodiment of the present invention, the recorded image with the closest matched ECG is selected; and, an operation (e.g., 409) is performed to select the recorded images (e.g., 401) for combination and/or correlation with the real time image (e.g., 405).

An alternative embodiment uses the ECG measurements, obtained during the capture of recorded images and real time images, in a different way. Since the ECG is sensed in both the recorded and real-time image data collections, it is possible to gate (e.g. capture) image data collections based on the ECG (e.g. every 33.3 milliseconds after the "R" wave detection). Thus, the recorded images (e.g. recorded images used to create composite recorded image 2853) and the real-time images (e.g. real time image 2851) used in the correlation and/or image overlay processes may always be captured at the same time in the timeline of the ECG. End-systole is a place in the ECG where heart motion is minimized and the heart size and shape is the most repeatable and a predefined period of time, such as 300 milliseconds after the "R" wave is detected, may be used as this same time in the timeline of the ECG. At this same time, the changes of heart size and shape are the most repeatable over a range of heartrates and blood pressures. Thus, the operator may select the end-systole time for the best image correlation. In alternative embodiments, a predefined period of time after another detected portion of the ECG wave may be used.

FIG. 11 shows another embodiment of an aspect of the inventions. This aspect relates to the display of two sets of images: a first set, which includes a first recorded image and a first real time image, and a second set, which includes a second recorded image and a second real time image. The first set is updated at a first frequency (e.g., only once each cardiac cycle such as at a predetermined time after the detection of the "R" wave) and the second set is updated at a second frequency (e.g., once every 33 milliseconds) which is higher than the first frequency. The first recorded image may be a composite of smaller field of view images, and the second recorded image may be a composite of smaller field of view images. The first set may be displayed substantially concurrently with the second set on the same, or a different, display device. The first set may include diagnostic information, and the second set may omit the diagnostic information. FIG. 11 shows an example of the first set 451 and the second set 453. The first set includes real time image 462, which is overlaid (e.g., by automatic, computer implemented correlation) onto a recorded image 461 which may be a composite from smaller field of view images. Real time image 462 and recorded image 461 may be, in at least certain embodiments, similar to real time image 2851 and recorded image 2853 respectively. Thus, real time image 462 may be generated from a 3-D echo imaging probe and show, in see-through view, a portion of the interior wall of the left ventricle, and recorded image 461 may also be generated from multiple images, each generated with a 3-D echo imaging probe, to show a larger field of view centered or positioned around or near the field of view of the real time image to show a larger portion of the interior of the left ventricle. The real time image 462 and the recorded image 461 may be updated only once (or twice) during a cardiac cycle while the second set may be updated very rapidly (e.g., an update of the second set may be every 33 milliseconds). Thus, a new real time image and a corresponding recorded image is displayed, for the first set, once in every cardiac cycle. The first set includes diagnostic information 464 (e.g., an indicator of abnormal tissue motion or abnormal wall thickness), while the second set 453 does not include this information but shows the catheter 463 which is also shown in the real time image 462. Treatment information (e.g., recorded injections 465 or other types of treatment) is also shown overlaid onto the recorded image 461 in the first set. In the second set, the recorded image 471 and the real time image 473 may be, in at least certain embodiments, similar to recorded image 461 and the real time image 462, respectively, except that the recorded image 471 does not show certain information which is shown in recorded image 461. The rapid updating of the second set allows an operator to look at the second set to get gross guide information (e.g., while actively moving the catheter within the left ventricle), and the first set, while updated more slowly, provides a more stable view of diagnostic and other information for measurement, recording and other purposes made easier by the presentation of a stable (relatively unmoving) image.

From this description, a person skilled in the art understands that some of the above-described methods can be combined in various ways. For example, the 3-D image matrix of heart can be generated for a time after a given feature for a number of heart rates or ranges of heart rate. Thus, the recorded image selected for display at the real time depends on the real time heart rate, as well as the time after a given feature. A multidimensional image matrix can be collected and associated with various physiologic parameters or ranges of parameters (image pixel coordinates and, pixel intensity and associated physiologic parameters may each be considered a dimension of the recorded image matrix); and, the real time physiologic parameters and the position of the portion of the medical instrument can be used to determine the image for display. Further variations may be initiated and/or controlled by the operator and/or provided by the equipment manufacturer. For instance, the orientation of the planes of the image slices may be selected by the operator and/or determined to match the orientation of the portion of the medical device. In another example, the views selected to be displayed may be automatically selected to include the last recorded or the current position of the catheter tip. In another instance, the recorded image matrices may be processed prior to medical device use to create/store 3-D surface matrices of interest (from the multidimensional image matrix) for use in later overlaying their projections and a projection of the portion of the medical device. Such an image may then be rotated under operator control to provide a visual sense of the 3-D relationships on a 2-D monitor screen.

In one embodiment of the present invention, the tracked positions are recorded as a function of time such that the positions of the tracked objected can be determined for the instance when an image is to be displayed. A representation of the tracked object is overlaid on the image for display substantially real time.

In one embodiment of the present invention, a real-time position of the portion of the device relative the anatomy (e.g., the real-time position of the catheter tip relative to the heart, as determined from the position tracked by the position tracking system and from the selected cardiac images according to the real time cardiac parameters) is recorded and annotated during a therapeutic or diagnostic operation, in addition to displaying the real-time position of the portion of the device relative to the anatomy. For example, the recorded image matrix (or image data selected or processed based on the real-time condition) can be modified to record such a position; or, a modified copy of prerecorded image data or part of the image data (like time after ECG "R" wave=0 image data) can be created; or, data related to the original recorded image and/or other data derived from the recorded images can be stored in machine readable media to indicate the real-time position of the portion of the device relative to the anatomy; or, the real-time position can be recorded so that it can be displayed in various manners without the recorded image(s). The annotation can be in terms of selected icons/symbols, a color coding, entered writing, the time and/or sequence of the annotation or annotation type, data from a catheter mounted sensor, data from another sensor or other equipment or derived data that indicate diagnostic or therapeutic information about that position and/or information gathered at the time or near the time that the device portion was at or near that position, or other forms and combinations of forms. This type of recording allows a procedure to be well documented for future review and analysis. It also allows the physician to more effectively guide a therapy by allowing other collected diagnostic information to be represented/accessible on/from the image(s)/display and, thus, it is easier for the physician to relate the collected diagnostic information to anatomic and/or other represented diagnostic information. It also allows the physician to more effectively guide a therapy by representing on the image(s) the locations and types of therapy previously applied. It may also be configured to display derived data from the previously recorded positions, real-time position data and/or annotations/annotation data (e.g., display the distance of the current real-time position of the portion of the device from the nearest previously recorded position that had a certain annotation), which would be especially useful in therapies requiring an injection at intervals over a selected tissue surface (spatial dosing). In another example, it may also be configured to display and/or record the change in position, maximum velocity and/or maximum acceleration of a recorded position over an ECG R-R interval or several intervals, which is a good indication of the contractile health of cardiac tissue.

In one embodiment of the present invention, interpolations are performed to provide intermediate frames of images from the collected images so that a smooth video image of the beating heart can be displayed according to the real time measured cardiac parameters, with a representation of the tracked object displayed at a position relative to the heart.

It is understood that parameters related to the shape and position of the heart, such as chest position (and/or movement), hemodynamic parameters, ventilation parameters, and other cardiac parameters (e.g., blood pressure, pulse wave, heart wall motion), can also be used to gate the playback of the recorded images. Indicators based one or more of these parameters can also be generated to gate the playback of the images.

FIG. 12 illustrates a method to display images according to one embodiment of the present invention. In one embodiment, the medical procedure involves the positioning of a medical device relative to an organ that moves in a periodical fashion, such as a heart. The recorded images are indexed according to the parameter that can be used characterize the periodic behavior of the organ, such as ECG of the heart.

For example, in FIG. 12, the recorded images are 3401 (e.g., 3403, 3407) indexed according to the cardiac phase related to the ECG (3411) for the recorded images. Thus, for a given cardiac phase related to the ECG, a corresponding recorded image can be selected from the recorded images. In one embodiment, the ECG (3415) taken in real time is used to determine (e.g., 3413) the current cardiac phase; and a corresponding recorded image can be selected to show the corresponding shape of the heart.

In one embodiment, one display area shows the real time images (e.g., 3421, 3425, etc.). This real time image display area is updated at a period substantially smaller than the cardiac cycle, such that the movement of the heart within each cardiac cycle is shown. The real time images (3421) may be the images captured in real-time from an ultrasound imaging system, or real-time images from an ultrasound imaging system superimposed on the corresponding recorded images selected according to the real time cardiac phases, or recorded images with a representation of the medical device superimposed at the corresponding location (e.g., determined using the real time images from the ultrasound imaging system, or from using other position tracking systems). The real time images (e.g., 3421, 3425) typically show the real time position of a medical device relative to the heart; and the real time images (e.g., 3421, 3425) may further include the information obtained from the recorded images.

Since the heart has different shapes in different cardiac phases, it may be difficult to map a position on the heart in one cardiac phase to the corresponding position in another cardiac phase. Thus, it may be desirable to record the positions relative to the same cardiac phase. Further, since the heart is moving rapidly within a cardiac cycle, it may be difficult to position the medical device accurately based on the real time images that are updated frequently during a cardiac cycle. Thus, in one embodiment, cycle images are also displayed in one display area.

In the display area for the cycle images, the image display is updated at a period substantially the same as the cardiac cycle. Thus, a relatively still display of the image of the heart for the corresponding cardiac phase is thus display. For example, cycle images 3431, 3433 and 3435 correspond to the same cardiac phase (approximately or exactly). The cycle images (e.g., 3431, 3433 and 3435) can be constructed in a way similar to the real time images (e.g., 3421, 3425). The cycle images can be a subset of the real time images selected according to the cardiac phase. Alternatively, the cycle images may be different from the real time images. For example, the real time images may be same as received from the ultrasound imaging system; and the cycle images can be the corresponding real time ultrasound images superimposed on one recorded image (e.g., 3407) that is selected according to the cardiac phase of the cycle images.

In one embodiment, the real time images are displayed in one display area, while the cycle images are simultaneously displayed in another display area. Alternatively, the system can allow the user to switch between viewing the real time images and the cycle images. For example, the period of display update may be adjusted relative to the cardiac cycle so that: 1) when the period is much smaller than the cardiac cycle, the real time movement of the heart is show; and 2) when the period is the same as the cardiac cycle, the relatively still display of the heart for a particular cardiac cycle is shown. Preferably, the particular cardiac phase is such that cardiac motion is minimal and cardiac dimensions are most consistent.

In one embodiment of the present invention, the positions of medical devices and/or therapeutic points and/or diagnosis points are recorded based on the display of cycle images for a particular cardiac phase. The position may be recorded relative to the real time ultrasound images, or the recorded images, or images derived from the recorded images and/or the real time ultrasound images.

In one embodiment, the image correlation operations are performed on or just before the update of the cycle images. Thus, the cycle images present the accurate position of the medical device relative to the recorded anatomy and/or pre-recorded guide information, such as diagnosis information, planned treatment sites, treated sites, etc.

FIG. 13 shows one example of a typical computer system, which may be used with the present invention. Note that while FIG. 13 illustrates various components of a computer system, it is not intended to represent any particular architecture or manner of interconnecting the components as such details are not germane to the present invention. It will also be appreciated that network computers and other data processing systems which have fewer components or perhaps more components may also be used with the present invention. The computer system of FIG. 13 may, for example, be an Apple Macintosh computer.

As shown in FIG. 13, the computer system 501, which is a form of a data processing system, includes a bus 502 which is coupled to a microprocessor 503 and a ROM 507 and volatile RAM 505 and a non-volatile memory 506. The microprocessor 503, which may be, for example, a G3 or G4 microprocessor from Motorola, Inc. or IBM is coupled to cache memory 504 as shown in the example of FIG. 13. The bus 502 interconnects these various components together and also interconnects these components 503, 507, 505, and 506 to a display controller and display device 508 and to peripheral devices such as input/output (I/O) devices which may be mice, keyboards, modems, network interfaces, printers, scanners, video cameras and other devices which are well known in the art. Typically, the input/output devices 510 are coupled to the system through input/output controllers 509. The volatile RAM 505 is typically implemented as dynamic RAM (DRAM), which requires power continually in order to refresh or maintain the data in the memory. The non-volatile memory 506 is typically a magnetic hard drive or a magnetic optical drive or an optical drive or a DVD RAM or other type of memory systems, which maintain data even after power is removed from the system. Typically, the non-volatile memory will also be a random access memory although this is not required. While FIG. 13 shows that the non-volatile memory is a local device coupled directly to the rest of the components in the data processing system, it will be appreciated that the present invention may utilize a non-volatile memory which is remote from the system, such as a network storage device which is coupled to the data processing system through a network interface such as a modem or Ethernet interface. The bus 502 may include one or more buses connected to each other through various bridges, controllers and/or adapters as is well known in the art. In one embodiment the I/O controller 509 includes a USB (Universal Serial Bus) adapter for controlling USB peripherals, and/or an IEEE-1394 bus adapter for controlling IEEE-1394 peripherals.

In one embodiment of the present invention, ECG measurement system 511 (and/or measurement systems for other cardiac parameters, hemodynamic parameters, ventilation parameters, chest position/movement, position of operation platform relative to a reference position) is coupled to I/O controller 509 so that the data processing system 501 can gate the playback of pre-recorded images (e.g., stored on nonvolatile memory 506). Ultrasound based real time imaging modality 512 (or CT or MRI based real time imaging modality) is coupled to I/O controller 509 so that the data processing system determines the position relative to the heart in images played back according to the input from ECG measurement system. In one embodiment of the present invention, data processing system 501 performs the image processing based on stored image matrices to provide different views, image slices, surfaces and others according to real time condition. In one embodiment of the present invention, data processing system 501 is also used to perform data processing for the imaging system (e.g., a CT or MRI based imaging system). Alternatively, data processing system 501 receives image data through a communication link (e.g., network interface 510) or a removable medium (e.g., a zip diskette, a CD-R or DVD-R diskette, removable hard drive, and others).

It will be apparent from this description that aspects of the present invention may be embodied, at least in part, in software. That is, the techniques may be carried out in a computer system or other data processing system in response to its processor, such as a microprocessor, executing sequences of instructions contained in a memory, such as ROM 507, volatile RAM 505, non-volatile memory 506, cache 504 or a remote storage device. In various embodiments, hardwired circuitry may be used in combination with software instructions to implement the present invention. Thus, the techniques are not limited to any specific combination of hardware circuitry and software nor to any particular source for the instructions executed by the data processing system. In addition, throughout this description, various functions and operations are described as being performed by or caused by software code to simplify description. However, those skilled in the art will recognize what is meant by such expressions is that the functions result from execution of the code by a processor, such as the microprocessor 503.

A machine readable media can be used to store software and data which when executed by a data processing system causes the system to perform various methods of the present invention. This executable software and data may be stored in various places including for example ROM 507, volatile RAM 505, non-volatile memory 506 and/or cache 504 as shown in FIG. 13. Portions of this software and/or data may be stored in any one of these storage devices.

Thus, a machine readable media includes any mechanism that provides (e.g., stores and/or transmits) information in a form accessible by a machine (e.g., a computer, network device, personal digital assistant, manufacturing tool, any device with a set of one or more processors, etc.). For example, a machine readable media includes recordable/non-recordable media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.); etc.

FIG. 14 illustrates a needle catheter which embodies features of the invention. In the embodiment illustrated in FIG. 14, the needle catheter 10 comprises an elongated shaft 11 having a proximal shaft section and a distal shaft section and a needle lumen 15, and a spherical distal tip 14 at the distal end of the shaft 11. A needle 16 is slidably disposed within the needle lumen 15 of the shaft, with an extended configuration in which the needle distal end extends distally from the distal end of the shaft (see FIG. 14), and with a retracted configuration (not shown) in which the needle distal end is proximally retracted into the catheter lumen. In the illustrated embodiment, the catheter 10 has a deflection member 17 (e.g., a tendon wire) connected to a deflection control mechanism 18 at a proximal adapter 19, for deflecting the distal end of the catheter 10. To effectively deflect the distal end of the catheter the deflection member 17 is preferably near the surface of the shaft in the deflecting (curving) portion. However, a catheter having a spherical distal tip in accordance with the invention can have a variety of suitable catheter configurations including a non-deflecting configuration. The proximal adapter 19 on the proximal end of the shaft has a port 20 configured for providing access to the needle 16 for delivery of an agent, or for aspiration, through the lumen of the needle 16. A variety of operative connectors may be provided at the proximal adapter depending on the desired use of the catheter 10. FIGS. 15-17 illustrate transverse cross sectional views of the catheter 10 of FIG. 14, taken along lines 2-2, 3-3, and 4-4, respectively.

In the embodiment of FIG. 14, the shaft comprises a tubular body member 21, which in one embodiment has a relatively flexible distal portion 52 and a relatively less flexible proximal portion 51. A variety of suitable catheter shaft designs can be used with the spherical distal tip of the invention, including deflectable needle catheter shafts described in U.S. Ser. No. 10/676,616, incorporated by reference herein in its entirety. The proximal portion 51 is typically formed at least in part of metal, such as a polymer reinforced with a braided or coiled metallic filaments or a hypotube or slotted metallic tube, although it may alternatively or in addition consist of a high modulus polymer. In the illustrated embodiment, the shaft 11 has a braided body layer 23 extending distally from a proximal end section of the catheter, and comprising a polymeric material encapsulating a wound tubular support layer typically formed of braided filaments of a metal such as stainless steel. The braid is encapsulated by an outer layer which is typically formed of multiple sections of differing durometers/polymers joined end to end to provide a stiffness transitions along the length of the catheter. The braid is formed over a polymeric core layer 24.

In the illustrated embodiment, the distal portion 52 of the tubular body member 21 of the shaft 11 comprises a cage typically formed of a slotted metallic tube. The compression cage 22 is configured to deflect laterally as discussed in the '616 application, incorporated by reference above. The cage 22 is typically covered with an outer jacket layer 50, which in one embodiment is an impedance matching quarter wavelength layer as discussed in more detail below.

In other embodiments, the cage 22 may be a wire, wires, a construction of wires, a thin metallic strip(s) or a combined construction that provides a restoring force to the deflection distal section of the shaft 11.

An inner tubular member 26 extending within the tubular body member 21 defines the needle lumen 15 of the shaft. The inner tubular member 26 is formed of a single layered, integral one-piece tube extending from the proximal to the distal end of the catheter, or alternatively of multiple sections of tubing with communicating lumens, and/or a multilayered tube(s). The deflection member 17 extends within a lumen of a second inner tubular member 25, and is secured to the shaft adjacent to the distal end of the distal portion 52 of tubular body member 21. In the illustrated embodiment, a stabilizing tubular member 27, typically comprising a dual lumen extrusion, is positioned within at least a section of the cage 22 to stabilize the position of the inner tubular members 25, 26 therein. The stabilizing member 27 is formed of a single section or multiple longitudinally adjacent sections of the tubing, and has a proximal end typically located within the cage 22 or a short distance proximal thereto. In one embodiment, the acoustic impedance of both the outer jacket and distal catheter shaft polymers (polymer mixtures) is adjusted using tungsten filings to attain both a low direct resultant reflected echo amplitude, but also the desired visibility under fluoroscopy. The stabilizing tubular member 27 may be processed in conjunction with the cage 22 such that the cage 22 is coated or covered by the material of the stabilizing tubular member 27. This coating or covering of the metallic cage 22 (or wire(s) or strip(s)) provides a more even acoustic impedance (places where metal is versus places where metal isn't) to the inside of the shaft for the outer jacket 50 to be matched to, as will be discussed in more detail below. In alternative embodiments, the stabilizing tubular member 27 is omitted.

The catheter spherical distal tip 14 extends distally of the distal outer surface of the shaft, and has a spherical portion 30 and a proximal support portion 31 which has a proximal end connected to the distal end of the distal portion 52 of tubular body member 21. In a presently preferred embodiment, a proximal end section of the distal tip 14 is bonded, for example using an adhesive, to the inner surface of the cage 22, although a variety of suitable configurations can be used to attach the spherical distal tip including a spherical distal tip formed integrally with the shaft 11.

The spherical portion 30 has a curving outer surface extending around the circumference of the distal tip to an included angle substantially greater than 180°. The outer diameter of the spherical distal tip 14 is a rigid (i.e., non-collapsing/expanding) outer diameter, which is typically approximately equal to the outer diameter of the distal portion 52 of the tubular body member 21 to provide the greatest range of imaging angles. The spherical distal tip 14 has a lumen extending therethrough which forms a distal section of the needle lumen 15 and which is in communication with a port 28 at a distal end of the spherical distal tip 14. In the embodiment illustrated in FIG. 14, a distal section of the inner tubular member 26 defines the lumen within the spherical distal tip 14. However, a variety of suitable configurations may be used including an embodiment in which the distal end of the inner tubular member is proximal to the distal end of the catheter.

In the illustrated embodiment, the proximal support portion 31 has a conically shaped section with an outer surface tapering distally to a smaller outer diameter. The support portion 31 is formed of a sufficiently strong material(s) to securely connect and support the spherical distal tip 14 during use of the catheter 10. The length and tapering angle of support portion 31 is preferably chosen such that it will not shield or block the spherical distal tip portion 30 from sonic energy over the designed range of distal tip imaging angles. Additionally, the spherical distal tip portion 30 and support portion 31 are configured to avoid catching on portions of the anatomy (i.e. valve to papillary muscle chordae) or on portions of the insertion devices (i.e. an introducer, a guide catheter) during positioning or withdrawal. Specifically, the tapers and curved surfaces of the spherical distal tip portion 30 and support portion 31 are designed limit the forces that may be applied to the anatomy or other devices by the spherical distal tip 14 before the catheter deflects enough to disengage from the obstruction.

In a presently preferred embodiment, the tip assembly is insert molded of a polymer/plastic 33 around a high strength support member such as a machined hollow pin 34 (see e.g., FIG. 14), or short length of stainless steel hypotube 35 with a flared end at/near the center of the spherical tip (see e.g., FIG. 18). The plastic material 33 is a damping material to dissipate sonic energy at the tip 14. The conical portion 31 of the tip assembly is typically molded from the same material as the spherical portion 30, and a portion of the pin 34 or hypotube 35 extends proximally out of it.

Once mounted on the catheter, the proximal end of the pin 34 or hypotube 35 resides inside the catheter shaft 21 and attaches the tip assembly to the distal end of the catheter shaft. Thus, while the tip assembly has a substantial metallic portion (i.e., the pin 34 or hypotube 35), it is covered and in contact with a plastic that has damping qualities, and it has at least a section not exposed directly to the sonic energy, to limit its impact on the ultrasonic imaging of the tip. The catheter tip 14 is configured for mechanically strong, secure attachment and support, while nonetheless minimizing the amount of metal at the catheter distal end in order to minimize the brightness and duration of the tip pyramid artifact in the ultrasonic image of the catheter distal end.

The spherical distal tip 14 preferably functions as an electrode, and thus has a conductor (e.g., a metal wire) electrically connected thereto. In the embodiment illustrated in FIG. 14, the deflection member 17 is electrically connected to the pin 34 so that the member 17 doubles as a deflection and a conduction wire. However, a variety of suitable configurations can be used including embodiments in which a separate conduction wire is provided which extends the entire length of the catheter or which extends between the deflection member and the spherical distal tip. Therefore, it should be understood that in alternative embodiments, the shaft 11 may include a separate conductor lumen extending within the tubular body member 21. The conduction wire is soldered, welded, mechanically crimped or imbedded or otherwise electrically connected to the spherical distal tip 14.

Although not illustrated, at least a second electrode is typically provided on the shaft 11, with a corresponding electrical conductor. The second electrode, functions, for example, as a reference electrode for the spherical distal tip electrode. The second electrode is preferably provided on the proximal portion 51 of the tubular body member 21 so that it is located out of the heart chamber, preferably superior to the heart chamber, such as in the aortic arch or a vena cava, for tip tissue contact/tissue ECG monitoring applications and/or about one centimeter behind the tip for ECG anomaly detection applications. In applications where pacing is anticipated to be required, many electrodes may be spaced along the distal portion of the catheter shaft, such that, at least, one electrode (with a surface electrode) or electrode pair will pace successfully at the current catheter position. The conductor wire(s) electrically connect to an electrical connector 41 which is provided at the proximal adapter 19 for connecting the catheter 10 to diagnostic or therapeutic equipment (not shown).

In the embodiment illustrated in FIG. 14, the metallic pin 34 has a proximal end 36 electrically connected to the deflection/conductor member 17 and has an exposed distal end at the distal end of the spherical distal tip 14 to form the distal tip electrode. The pin 34 has two grooves (illustrated with broken lines in FIG. 14) on opposite sides of the proximal section of the pin 34, and the distal end of the deflection/conductor member 17 is within one of the grooves.

FIG. 18 illustrates an alternative embodiment in which spherical distal tip 14b has a hypotube 35 which does not have an exposed distal surface. As a result, to function as an electrode, at least a portion of the outer surface of polymeric layer 33 of the tip 14b is coated or otherwise provided with a conductor (metallic) outer layer(s) such as, for example, a gold outer layer and a copper inner layer. The conductor (metallic) coating is very thin, and is not illustrated in FIG. 18. The thin metallic coating(s) on the tip has too little mass/size to store much sonic energy, and is also in contact with the damping plastic, and is so thin that a part of its reflective properties are determined by the properties of the plastic behind it. The thin metallic coating(s) (not shown) form a wall preferably having a spherical outer surface, and a spherical inner surface defining a spherical interior chamber, with the plastic 33 filling the spherical interior chamber around the needle lumen of the spherical distal tip. FIG. 19 illustrates a transverse cross section of the tip 14b of FIG. 18, taken along line 6-6.

In the embodiment illustrated in FIG. 18, a separate conduction wire 40 is electrically connected to the hypotube to electrically connect to the outer conductor (metallic) coating. A band 41, typically formed of metal, connects the deflection member 17 between the hypotube 35 and the cage 22, in the illustrated embodiment. Although not illustrated in FIG. 18, the shaft would typically include a needle 16 in inner tubular member 26, and one or more additional inner tubular members, which are similar to inner tubular member 25 of FIG. 14, and which contain the deflection member 17 and/or conduction wire 40 in the embodiment of FIG. 18.

FIG. 20 illustrates a longitudinal cross sectional view of an alternative embodiment of a spherical distal tip 14c embodying features of the invention, having a wall formed of a mixture of a polymeric material and a metallic material 42. The mixture is blended or otherwise combined and comprises a sufficient amount of metallic material 33 so that the spherical distal tip 14 functions as an electrode when electrically connected to diagnostic or therapeutic equipment. In a presently preferred embodiment, the polymer/metallic material mixture has about 80% to about 98% metallic materials 33 by weight. A variety of suitable materials can be used including metallic materials 33 selected from the group consisting of tungsten, tungsten iridium, stainless steel, gold or platinum and a variety polymeric materials are suitable including those selected from the group consisting of epoxies, silicones and thermoplastics.

In the embodiment of FIG. 20, the wall of the distal tip 14c has a spherical outer surface and an inner surface defining a needle lumen 43 within the spherical distal tip, so that the tip 14c has a thickened wall portion which fills the space between the needle lumen 43 therein and the spherical outer surface of the distal tip 14c. The lumen 43 defined by the wall is configured for being in communication with a proximal section of the needle lumen 15 of the inner tubular member 26, or, alternatively, for receiving a tubular member such as a distal section of the inner tubular member 26 or a separate tubular member.

Thus, in the embodiment illustrated in FIG. 20, the polymer/metallic mixture is molded or otherwise shaped to form the spherical distal tip wall extending from the outer to the inner surface of the tip 14. Alternatively, the metal/polymer mixture can be used to form an outer layer on a spherical distal tip similar to the embodiment discussed in relation to FIG. 18. Polymer/metal mixtures which contain a sufficient amount of polymer to facilitate working with the mixture typically do not contain a sufficient amount of metal to be conductive. Therefore, In a presently preferred embodiment, such polymer/metallic material mixtures are made conductive by first mixing the metallic material with the polymer or the polymer parts while the polymer or the polymer parts are in a liquid state, and the non-conductive mixture is then applied to the spherical tip, and the tip is subjected to heat and pressure in a mold constructed to allow the polymer to flow out of the mold while most of the metallic material is retained within the mold. In this way the concentration of the metallic material is raised to the point that many of the metallic material particles contact each other and thus, a conductive layer is former on the spherical tip (or also on other portions of the tip). Several cycles of the addition of the non-conductive mixture and the re-application of heat and pressure may be required in some processes to create a conductive tip of the desired shape and dimensions.

The spherical distal tip 14 has a uniformly curving outer surface extending around the circumference of the tip 14. The outer diameter of the spherical distal tip 14 is preferably equal to or less than the outer diameter of a portion of the shaft 11 which defines the distal outer surface of the shaft proximally adjacent to the spherical distal tip 14 (although the outer diameter of the spherical portion 30 of the distal tip 14 is greater than a distal section of the conically shaped portion 31). Minimizing the outer diameter (OD) of the distal tip 14 so that it is not greater than the OD of the catheter shaft is preferable in order to minimize the size of the introducer (OD/ID) required at the catheter insertion site which has to accommodate the catheter therein. A larger introducer OD causes a larger puncture wound, which studies have shown have a greater incidence of complications such as pain, bleeding, infection and extended healing times. Typical catheters used to inject substances may range in size from about 4 F (about 1.3 mm OD) for vessel needle or other injections to about 9 F (about 3 mm OD) for ventricular needle or other injections. The spherical portion 30 of the distal tip may have a smaller radius than catheter body radius to help minimize the brightness and duration of the echo and tip pyramid artifact of the ultrasonic image, however; all other things being equal, the smaller the radius of the spherical distal tip, the smaller the range of angles from which that tip may be imaged.

Although generally not preferred due to concerns regarding effective sterilization, an alternative spherical distal tip (not shown) can have a hollow structure with a spherical wall defining a hollow interior chamber (i.e., not filled with plastic 33) and optionally formed of metal or a polymer-metal blend to function as a distal tip electrode.

FIG. 21 illustrates the needle catheter 10 with the distal end of the catheter 10 within the left ventricle 45 of the patient's heart 46. The catheter 10 is typically advanced in a retrograde fashion within the aorta 47, via the lumen of an introducer sheath which is inserted into the femoral artery. The catheter 10 illustrated in the embodiment of FIG. 14 is not configured for advancement over a guidewire, although in alternative embodiments and delivery sites, such as into veins or arteries, a guidewire lumen is provided in the shaft 11 for slidably receiving a guidewire therein. Additionally, in such vessel applications, the guidewire and catheter may be inserted into position using a guiding catheter that is first inserted into the introducer. In this intracardiac application, a deflecting mechanism is desired. By activating the deflection member 17 using the deflection control mechanism 18 the distal end of the catheter is caused to deflect away from the longitudinal axis of the shaft 11. With the distal end of the spherical distal tip 14 thus positioned in contact with a desired site of the ventricle wall, electrical data can be collected from the spherical distal tip electrode 14. The electrical data (e.g., tissue contact ECG) facilitates tissue diagnostics (in combination with echo image ventricle wall motion measures) to determine if the site should be treated or not. The site can be treated by direct injection of a therapeutic agent, such as a biological or chemical agent, from the needle 16. FIG. 21 illustrates the distal end of the spherical distal tip 14 and the port 28 against the ventricle wall, with the needle 16 in the extended configuration advanced out the port 28 and into the cardiac tissue 48 of the ventricle wall. Multiple sites within the left ventricle can be thus accessed and treated using the catheter of the invention.

Although illustrated in the ventricle, a catheter of the invention can be used to inject into the vessel wall or through the vessel into the myocardium or other adjacent tissues. Thus, although the distal needle port 28 is in the distal-most end of the spherical distal tip 14 coaxial with the longitudinal axis of the catheter in the embodiment of FIG. 14 (with the needle extending aligned with the longitudinal axis of the catheter), in alternative embodiments (not shown; e.g., those for injecting into or through a vessel) the catheter 10 has a needle port configured to direct the needle at an angle away from the longitudinal axis of the catheter. For example, the port through which the needle extends can be located eccentric to the longitudinal axis of the catheter or in a side wall of the catheter proximal to the distal end of the spherical distal tip.

Ultrasound can be used in conjunction with the catheter supplied ECG to provide tissue diagnostics by visualization of the wall motion and thickness. Additionally, the catheter 10 facilitates using ultrasonic imaging for visualization and positioning of the catheter 10. Specifically, with the catheter 10 distal end in the left ventricle (or other desired location within the cardiac anatomy), sonic energy is directed at the spherical distal tip 14 from an ultrasonic imaging device (not shown). The ultrasonic imaging device is typically an external device, a TTE probe (Transthoracic Echo, probe on the chest), although a TEE probe (Transesophageal Echo, probe in the throat), an ICE probe (Intracardiac Echo, probe in a cardiac chamber) or an IVUS (Intravascular Ultrasound, probe in a vessel) can alternatively be used.

The spherical distal tip 14 reflects the sonic energy more diffusely than a non-spherical tip, to provide an ultrasonic image of the distal end of the catheter from a wide range of angles relative to the viewing direction of the ultrasonic imaging device. Additionally, the spherical distal tip 14 formed of a polymeric and metallic materials uses less metal in the distal tip than a solid metal distal tip or band electrode, and the metallic portions are in contact with the sonic energy damping plastic material 33, so that the tip pyramid artifact has a desired low level of brightness and shorter duration or is absent entirely from the display.

In one embodiment, during ultrasonic imaging of the catheter 10, one or more of the lumens of the catheter shaft are filled with an aqueous fluid so that a plastic-aqueous fluid interface is formed which reflects less sonic energy than a plastic-air interface. Specifically, the ultrasonic image is produced with the aqueous fluid within the needle lumen 15 of the shaft. In embodiments having one or more additional lumens, in addition to the needle lumen 15 of the shaft, the one or more additional lumens are preferably also filled with the aqueous fluid during ultrasonic imaging. For example, the lumenal space, if any, of the tubular body member 21, between the inner surface of the tubular body member 21 and the outer surface of the inner tubular members 25, 26, is preferably filled with the aqueous fluid during ultrasonic imaging.

In a presently preferred embodiment, the catheter 10 has an impedance matching outer jacket layer 50 on an outer surface of at least a portion of the shaft 11, configured to decrease the reflected wave ultrasonic signal of the catheter. The impedance matching outer jacket layer 50 typically extends along at least a portion of the distal section of the shaft, and preferably is not provided on the proximal section 51. In the illustrated embodiment, the layer 50 has a distal end located proximal to the conical portion 31 and the spherical portion 30 of the spherical distal tip 14. The layer 50 is formed of a polymeric material, which in one embodiment is selected from the group consisting of a low density polyethylene (LDPE), EVA, or elastomers including neoprenes, silicones, SBS's (linear styrene-butadiene-styrene triblock copolymers, SB's (Radial styrene-butadiene block copolymers), SIS's (linear styrene-isoprene-styrene triblock copolymers), butadienes and polyurethanes. In an embodiment in which the layer 50 is formed of an elastomer such as polyurethane, a lubricious surface coating (not shown) is typically provided on an outer surface of layer 50 to decrease the relatively high friction of the elastomer. Although not illustrated, the outer jacket layer 50 preferably has an irregular wall thickness forming a rough outer surface.

In the embodiment illustrated in FIGS. 14 and 18, the outer jacket layer 50 is on an outer surface of the compression cage 22, with a proximal end bonded to a distal end of the multi-layered braid reinforced body of the proximal shaft section. In one embodiment, the layer 50 is fusion bonded to an underlying polymeric layer (not shown) formed of a compatible polymer. For example, in one embodiment, the layer 50 is formed of LDPE, and an underlying polymer layer forming part of the distal section 52 of the tubular member 21 is formed of a high or medium density polyethylene (HDPE, MDPE). However, the layer 50 can alternatively be friction fit onto the shaft, as for example in the embodiment in which the layer 50 is formed of an elastomeric material such as polyurethane, and the elastomeric layer 50 is applied by allowing a temporarily expanded layer 50 to retract down onto the shaft 11.

The impedance matching outer jacket layer 50 has an acoustic impedance which is between an acoustic impedance of blood and an acoustic impedance of the adjacent layer of the section of the shaft underlying the outer jacket layer, such that it more closely matches the acoustic impedance of the blood than does the polymeric material forming the outer layer along the distal section 52 directly underneath the outer jacket layer 50. For instance, the acoustic impedance of blood is about $1.4 \times 10^5$ gram/(cm$^2$sec), silicone is about $1.6 \times 10^5$ gram/(cm$^2$sec), soft polyurethane is about $1.8 \times 10^5$ gram/(cm$^2$sec), HDPE is about $2.2 \times 10^5$ gram/(cm$^2$ sec) and stainless steel is about $46 \times 10^5$ gram/(cm$^2$ sec). The large mismatch between the acoustic impedance of the material(s) forming the distal section 52 (i.e., in the absence of the layer 50), would cause a large proportion of the ultrasound wave to be reflected off the blood/catheter interface. The impedance matching outer jacket layer 50 is formed of a material which provides an intermediate impedance between blood and the material forming the distal section 52, so that at each material interface there is less mismatch, and more of the ultrasound wave propagates forward, rather than reflecting backward.

The impedance matching outer jacket layer 50 preferably has a thickness of a quarter or three quarter wavelength of the center frequency of the ultrasound waves emitted by the ultrasound imaging device or displayed by the ultrasonic imaging system, so that destructive interference occurs between the reflected waves from the outer and inner surfaces of the jacket layer 50. The acoustic properties (e.g. acoustic impedance) of the outer jacket layer 50 (and/or the inner portions of the distal catheter shaft 11) may be chosen or adjusted such that the amplitudes of the reflected waves from the outer and inner surfaces of the jacket layer 50 are more equal and thus destructively interfere to produce a lower amplitude resulting reflected echo. Such adjustments may be made according formulas relating acoustic impedance to acoustic reflection and relating the physical properties of materials and mixtures to their acoustic impedance, as are well known in the art. The quarter or three quarter wavelength, impedance matching outer jacket layer 50 facilitates producing an ultrasonic image of the catheter shaft 11 at the perpendicular (direct echo) viewing direction which is not disadvantageously bright, to minimize the catheter curved body artifact in 3D echo systems.

The thickness of the quarter or three quarter wavelength layer is determined based on the speed of sound in the polymeric material of the layer and the desired frequency setting of the ultrasonic imaging device. For example, in one embodiment, the quarter wavelength impedance matching layer 50 is selected from the group consisting of a polyethylene layer having a thickness of about 0.0049 inches, and a polyurethane layer having a thickness of about 0.0044 inches, for use with ultrasonic imaging at a center frequency of 4 MHz. It should be noted that the values given above are typical of LDPE and soft polyurethanes, however, there are many polyurethane and polyethylene formulations that have a different sound velocity properties.

FIG. 22 illustrates an elevational view of an alternative needle catheter 60 embodying features of the invention, having rotational orientation markers. In the embodiment of FIG. 22, the transvascular needle catheter 60 generally comprises an elongated shaft 61 having a proximal section, a distal section, and a needle lumen 65 (see FIG. 24) in communication with a distal port 67 which is in a side wall of the distal shaft section and which is spaced proximally from the distal end of the catheter, and a needle 66 slidably disposed in the needle lumen. Although not illustrated, the shaft 61 typically has reinforcements, such as metallic braided reinforcing filaments embedded in the polymeric material of the wall of the shaft 61. FIG. 22 illustrates the needle in an extended configuration, extending out the port 67 away from the longitudinal axis of the catheter 60. A proximal adapter 69 on the proximal end of the shaft has a port 70 configured for providing access to the needle 66 for delivery of an agent, or for aspiration, through the lumen of the needle 66. A variety of operative connectors may be provided at the proximal adapter depending on the desired use of the catheter 60. The catheter 60 can have a variety of suitable shaft configurations and/or operative distal ends, as are conventionally known. For example, for details regarding suitable transvascular needle catheter designs suitable for use with embodiments of the invention, see U.S. Pat. Nos. 6,283,947; 6,692,466; 6,554,801; and 6,855,124, incorporated by reference herein in their entireties. For example, in one embodiment (not shown), a distal end portion of the needle lumen extends along a proximal tapered section of the inflated balloon such that the extended needle is directed away from the longitudinal axis of catheter shaft.

The catheter shaft 61 has marker bands 71 on at least the distal section 62, which in a presently preferred embodiment are formed of a material having echo reflective properties which are different (preferably more highly reflective) than the adjacent portions of the catheter shaft. For example, in one embodiment the marker bands 71 are formed of a metal or a polymer/metallic material mixture. The marker bands 71 may or may not also be visible under fluoroscopy.

A plurality of rotational orientation portions 72a-72d are on an outer surface of the catheter shaft 61, and are formed of a material having echo reflective properties which are different (preferably more highly reflective) than the adjacent portions of the catheter shaft. In a presently preferred embodiment, the rotational orientation echogenic portions 72 are formed of the same material as the marker bands 71, such as a metal (i.e. gold, tungsten, tungsten-iridium), a higher acoustic impedance polymer, or a metal filled polymer. Thus, portions 72 may, or alternatively may not, additionally be visible under fluoroscopy. In the embodiment shown in FIG. 23, illustrating an enlarged partial longitudinal cross section of the catheter of FIG. 22, taken within circle-10, the rotational orientation echogenic portions 72 are formed of a mixture of a polymeric material and a metallic material 74. The polymeric/metallic material mixture facilitates bonding the portions 72 to the outer surface of the polymeric shaft 61, as for example by adhesive or preferably by fusion bonding. Alternatively, portions 72 may consist of metal, and in one embodiment (not shown), portions 72 formed of metal are soldered or otherwise connected to a metallic braided reinforcement within the polymeric wall of the shaft 61 for secure attachment.

In a presently preferred embodiment, the portions 72a-d all have the same size, shape, and material composition configured to produce an echo (image) on the ultrasonic image of the catheter which is not overly bright. The relative thickness of the rotational orientation echogenic portions 72 may be somewhat exaggerated in the figures for ease of illustration, and is preferably selected to avoid disadvantageously increasing the profile of the catheter. The rotational orientation echogenic portions 72 typically have a thickness of about 0.001" to about 0.008" and a length/width of about 0.010" to about 0.040", and may project slightly above the outer surface of the shaft 61 or be wholly or partially recessed within the outer surface (e.g., jacket layer) of the shaft 61, and are preferably slightly recessed below the outer surface of the shaft.

In a presently preferred embodiment, the shaft has an outer polymeric jacket layer with holes in it in which the rotational orientation echogenic portions 72 are placed and bonded to the shaft, and the portions 72 are formed of a metal, a metal filled polymer, or a high acoustic impedance plastic, with a curved outer surface to provide a direct image at the desired range of probe angles relative to the catheter shaft. Such a configuration facilitates ultrasonic imaging of the shaft (due to the jacket), and determining proximal and distal locations from markers 71, and determining rotational orientation from markers 72 which are easily imaged when on the side of the catheter facing the imaging probe.

FIG. 24 illustrates a transverse cross sectional view of the catheter of FIG. 22, taken along line 11-11. In the illustrated embodiment, the shaft 61 has an inflation lumen 62 and a guidewire lumen 63 in addition to the needle lumen 65 of the shaft 61. In the illustrated embodiment, the catheter 60 is configured for rapid exchange, with a guidewire 68 slidably disposed in guidewire lumen 63 and through a guidewire proximal port spaced distally from the proximal end of the shaft. However, a variety of suitable catheter shaft designs can be used as are conventionally known. A balloon 64 on the catheter distal section has an interior in fluid communication with the inflation lumen 62 for inflating the balloon. The inflated balloon 64 can be configured for a variety of suitable functions including to facilitate positioning the needle distal port 67 of the shaft against the vessel wall, or to anchor the catheter within the vessel lumen, or to occlude the vessel lumen. However, a variety of suitable shaft configurations can be used including shafts which do not have balloon 64, inflation lumen 62, and/or guidewire lumen 63, or which have one or more addition lumens such as a fluid delivery lumen configured for delivery of fluid such as medication or contrast agent to the patient from a port in the shaft distal section. Similarly, in alternative embodiments, the shaft 61 includes one or more additional needle lumens with additional needles slidably disposed therein (not shown).

Under ultrasonic imaging, the distal most marker band 71 in the embodiment of FIG. 22 illustrates the longitudinal location of the needle port 67 of the shaft 61. However, because the marker bands 71 are uniform around the entire circumference of the catheter shaft 61, the ultrasonic image of the marker bands 71 will appear irrespective of the rotational orientation of the catheter. Practical injection needles 66 are generally too small to reflect sound waves well enough to be imaged by echo systems. Also, the needle 66 is often shielded from the sound waves by the catheter shaft 61. Thus, the needle 66 will not be seen/be distinguishable in the ultrasonic image.

The rotational orientation echogenic portions 72 are arranged in an array in which each adjacent pair of portions 72 are circumferentially and longitudinally spaced apart from one another. In the embodiment of FIG. 22, four portions 72a-d are proximally adjacent to the needle port 67, and are circumferentially spaced apart in 90° intervals around the circumference of the shaft. However, alternative numbers and spacings can be used depending on factors such as the desired orientation determination performance characteristics of the catheter, the echogenicity and orientation of the portions 72, and the catheter shaft design. In a presently preferred embodiment, at least 4 portions 72 are provided.

FIG. 25 shows a perspective transverse view of the catheter of FIG. 22, through portion 72a, and looking proximally so that the proximally spaced portions 72b-d are also visible, to illustrate the direct reflection of sound waves from an ultrasonic imaging probe 80. The portion 72a that is directly in the path of the sound wave and presents a face surface that can directly reflect an echo back to the probe 80, will be imaged the brightest. The portion 72c on the side of the catheter opposite to the ultrasonic imaging probe 80 will produce a direct reflection, but because the sound waves that hit it and its reflected echo must pass thru the catheter body, its echo will have a small amplitude and be displayed much less bright (or not at all) than the portion 72a (some of the sonic energy is reflected off the catheter body/blood interface and some of the sonic energy is dissipated as heat in the plastic catheter body). The two portions, 72b and 72d, which are 90 degrees from the portion 72a (i.e., the face surface of each portion 72b and 72d is oriented at 90 degrees from the path of the sound wave) will produce an echo directed away from the ultrasonic imaging device probe and will therefore not be imaged.

FIG. 26 is a representation of the displayed 3D ultrasonic image of a section of the catheter of FIG. 22 by the probe oriented as shown in FIG. 25. Only portion 72a with its most direct reflected echo shows up in a distinguishable manner in this representation. In alternative embodiments, the other portions 72b-d could be made distinguishable in the view of FIG. 26, but will be much less bright than portion 72a (e.g., using portions 72 formed of more highly echogenic materials/structural shapes, or different echo system display settings). FIG. 27 is a representation of what the same image in FIG. 26 would look like if the section of the catheter in FIG. 26 were rotated 45° in the direction shown by the arrow in FIGS. 25 and 26. In this case, both portions 72a and 72d are in the direct path of the probe's sound waves and are only 45° from the most direct reflection path shown in FIG. 25. Thus, they are equally bright, and brighter than portions 72b and 72c, but dimmer than portion 72a was in FIG. 26 (the brightness being represented in the figures by the degree of shading). In other embodiments, the outer surfaces of the portions 72 could be curved such that 72a and 72d were equally as bright as portion 72a was in FIG. 26.

At least at 45° intervals in the embodiment of FIG. 22, the rotational orientation of the catheter 60 relative to the probe 80 may be easily distinguished by distinctive echo images of this section of the catheter 60. Thus, the rotational orientation of the needle 66 (or any other feature locked to the catheter body) can be determined from the 3D echo image. Additionally, the distal end of this catheter section is distinguishable from its proximal end by the marker bands 71. Because the needle 66 is near the distal marker band 71, the location of the needle 66 in the ultrasonic image is known. It should also be evident that, when in the patient's body, a 3D image of the patient's body tissues would be present and thus, the location and direction of the needle travel would be known relative to the imaged anatomy. This is true in any projection, if the position/direction of the probe 80 is known or indicated on the image. Thus, the catheter 60 facilitates directing the needle 66 into the desired anatomy in the desired direction by observing a 3D image display, and manipulating the catheter (rotational and/or longitudinal manipulations) as needed. It should also be evident that many modifications can be made to distinguish other rotational orientation intervals or other catheter features. The number and location of the rotational orientation echogenic portions 72 and the number and positions of marker bands 71 are selected to preferably provide incremental information regarding the rotational orientation of the catheter and the proximal and distal ends of the orientation indicating section of the catheter shaft. Thus, a small amount of rotation produces a distinguishable change in the ultrasonic image of the array of portions 72, providing highly detailed information about the catheter rotation. For example, the array of portions 72 of the embodiment of FIG. 22 would produce a different image depending on whether the catheter was rotated 45° clockwise or counterclockwise. Additionally, due to the number and spacing of the rotational orientation echogenic portions 72 in the embodiment of FIG. 22, the catheter 60 does not have to be rotated to determine the rotational orientation of the catheter in the patient's body, because one or more of the portions 72 will be visible in an ultrasonic image of the catheter.

In one embodiment, a method of the invention includes overlaying or alternating a 3-D echo image of a needle catheter of the invention with an image (such as a 3-D echo, 3-D biplanar fluoro or CT image) of the patient's blood vessels adjacent to the needle catheter. The blood vessel image is typically obtained using contrast injections into the arteries and/or veins. By overlaying or alternating the images, the method thus avoids injecting the needle into the adjacent blood vessels during a procedure using a transvascular or intraventricular needle catheter of the invention.

While the present invention is described herein in terms of certain preferred embodiments, those skilled in the art will recognize that various modifications and improvements may be made to the invention without departing from the scope thereof. For example, the damping features of the distal tip electrode may be used to reduce the ultrasonic imaging artifacts of other elements such as other electrodes or markers on the catheter. Additionally, while discussed primarily in terms of a needle catheter, it should be understood that a variety of medical devices can be used which embody features of the invention including surgical and implantable devices, and other catheters such as balloon catheters, guiding catheters, ablation catheters, device delivery catheters and catheters that accommodate or incorporate sensors (i.e. temperature, chemical, oxygen, etc.). For example, the needle can be eliminated and solution infused through the empty lumen of the catheter (e.g., to inject directly into the bloodstream just proximal of the area to be treated). Additionally, in vessel injection systems, the spherical tip will likely not need to function as an electrode, so the conduction requirement may be omitted.

Thus, the echogenic catheter features being disclosed are applicable to all types of catheters/other devices that may be guided by ultrasound and/or must be present in the anatomy during ultrasonic imaging. Additionally, although the catheter features are useful for use with 2D or 3D ultrasonic imaging systems, it should be noted that for the purpose of catheter guidance, a 3D echo system is preferred to the "slice" image provided by a 2D echo system. A 2D echo system produces images that are like viewing a very thin planar slice thru the anatomy and the catheter, making it extremely difficult to distinguish/find a catheter, follow a catheter to its tip or other relevant portion and determine where in the anatomy the relevant portion of a catheter is located/oriented or is located/oriented relative to a previous location/orientation. A 3D echo system produces images that can either be a see-through representation of large 3D volume of the anatomy and catheter or a 3D surface image of the same. In a 3D image, anatomic reference points abound in the image and, with a properly echogenic catheter (as described in this application), all portions of the catheter in the image volume may be seen, and the direction of the catheter shaft relative to the anatomy is easily visualized as described herein.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A system for imaging a body to guide a medical operation, the system comprising:
    a transducer to scan an anatomy;
    a signal processing unit coupled to the transducer to generate a plurality of first images of the anatomy including a heart, each of the first images corresponding to a particular position and orientation of the transducer relative to the anatomy;
    means for combining the plurality of first images of the anatomy into a recorded image of the anatomy, the recorded image having a field of view of the anatomy larger than each of the plurality of first images;
    means for obtaining a real time image of the anatomy during the medical operation, the real time image having a field of view of the anatomy smaller than the recorded image, the real time image containing an image of a medical device used in the medical operation in a portion of the anatomy;
    means for receiving real time measurements of a cardiac parameter;
    means for determining a cardiac phase in which the real time image corresponds to based on the real time measurements of a cardiac parameter;
    means for selecting the recorded image based on the cardiac phase from a plurality recorded images that are associated with different cardiac phase of the heart, before aligning the real time image with the recorded image; and
    means for aligning the real time image with the recorded image through correlation of imaging data from the real time image and the recorded image to determine a spatial relation between the real time image and the recorded image.

2. The system of claim 1, wherein the recorded image contains no image of the medical device in the portion of the anatomy.

3. The system of claim 1, further comprising:
    means for displaying, on a display area, an image containing information derived at least partially from the real time image of the anatomy; and
    means for updating the display area with information derived at least partially from real time images of the anatomy at a period substantially equal to a cardiac cycle of the heart.

4. The system of claim 1, wherein the transducer is ultrasound based; and said means for obtaining the real time image of the anatomy couples to the transducer and the signal processing unit to obtain the real time image.

5. The system of claim 4, wherein at least one of the first images and the real time image is selected from the group consisting of: transthoracic echocardiogram (TTE) images, transesophageal echocardiogram (TEE) images, and intracardiac echocardiogram (ICE) images.

6. The system of claim 1, wherein the medical device comprises a tip portion of a catheter with an omni-directional ultrasonic transducer.

7. The system of claim 1, further comprising:
    means for displaying at least a portion of the anatomy based on both the real time image and the recorded image.

8. The system of claim 7, wherein the portion of the anatomy is displayed with a portion of the real time image superimposed on the recorded image.

9. The system of claim 7, wherein the real time image and the recorded image are displayed on a display surface in an alternating way with anatomically correct alignment on the display surface.

10. The system of claim 1, further comprising:
    means for obtaining an image highlighting the medical device through subtracting the real time image and the recorded image;
    means for detecting an outline of the medical device through edge detection in the image highlighting the medical device; and
    means for determining a location of the medical device from the outline of the medical device.

11. The system of claim 1, wherein the real time image is obtained through an ultrasound based imaging modality; the medical device includes a portion controllable to move; and the system further includes:
    means for detecting a location of the medical device through recognizing a Doppler shifted portion of image data corresponding to the portion of the medical device which is controllable to move; and
    means for displaying a representation of the medical device over the recorded image according to the location of the medical device.

12. The system of claim 1, wherein the real time image is obtained through an ultrasound based imaging modality; and the system further includes:
    means for determining an ultrasound propagation delay between a portion of the medical device and an imaging probe of the ultrasound based imaging modality;
    means for determining a position of the portion of the medical device using the ultrasound propagation delay; and means for displaying a representation of the medical device over the recorded image according to the location of the medical device.

13. A method to guide a medical operation, the method comprising:
    obtaining a plurality of first images of an anatomy comprising a heart;
    combining the plurality of first images of the anatomy into a recorded image of the anatomy, the recorded image having a field of view of the anatomy larger than each of the plurality of first images;
    obtaining a real time image of the anatomy during the medical operation, the real time image having a field of view of the anatomy smaller than the recorded image, the real time image containing an image of a medical device used in the medical operation in a portion of the anatomy;
    receiving real time measurements of a cardiac parameter;
    determining a cardiac phase in which the real time image corresponds to based on the real time measurements of a cardiac parameter;
    selecting the recorded image based on the cardiac phase from a plurality of recorded images that are associated with different cardiac phases of the heart before said aligning; and
    aligning the real time image with the recorded image through correlation of imaging data from the real time image and the recorded image to determine a spatial relation between the real time image and the recorded image.

14. The method of claim 13, wherein the recorded image contains no image of the medical device in the portion of the anatomy.

15. The method of claim 13, wherein the correlation includes searching for a maximum correlation value; and the method further comprises:
    displaying an indication of a degree of alignment between the real time image and the recorded image during said searching;
    wherein the degree of alignment between the real time image and the recorded image is indicated in one of:
    an image color change,
    a label, and
    a weight to blend the real time image and the recorded image.

16. The method of claim 13, wherein said correlation comprises:
    detecting anatomical features in the real time image and the recorded image; and
    matching the anatomical features to improve alignment between the real time image and the recorded image.

17. A non-transitory machine readable storage medium containing executable computer program instructions which when executed by a data processing system cause said system to perform a method to guide a medical operation, the method comprising:
    obtaining a plurality of first images of an anatomy;
    combining the plurality of first images of the anatomy into a recorded image of the anatomy, the recorded image having a field of view of the anatomy larger than each of the plurality of first images;
    obtaining a real time image of the anatomy during the medical operation, the real time image having a field of view of the anatomy smaller than the recorded image, the real time image containing an image of a medical device used in the medical operation in a portion of the anatomy;
    receiving real measurements of a cardiac parameter;
    determining a cardiac phase in which the real image corresponds to based on the real time measurements of a cardiac parameter
    selecting the recorded image based on the cardiac phase from a recorded images that are associated with different cardiac phases of the heart before said aligning; and
    aligning the real time image with the recorded image through correlation of imaging data from the real time image and the recorded image to determine a spatial relation between the real time image and the recorded image.

18. The medium of claim 17, wherein the recorded image contains no image of the medical device in the portion of the anatomy and wherein the anatomy includes a heart; and the method further comprises:
    receiving real time measurements of a cardiac parameter;
    determining a cardiac phase in which the real time image corresponds to based on the real time measurements of a cardiac parameter; and
    selecting the recorded image based on the cardiac phase from a plurality of recorded images that are associated with different cardiac phase of the heart before said aligning;
    displaying at least a portion of the anatomy based on both the real time image and the recorded image;
    wherein the portion of the anatomy is displayed with a portion of the real time image superimposed on the recorded image, or on a display surface in an way alternating between the real time image and the recorded image with anatomically correct alignment on the display surface; and
    wherein both the first images and the real time image are obtained from a same ultrasound imaging system; and
    the ultrasound imaging system captures an image from the group consisting of: transthoracic echocardiogram (TTE) images, transesophageal echocardiogram (TEE) images, and intracardiac echocardiogram (ICE) images.

19. The medium or claim 17, wherein the correlation includes searching for a maximum correlation value; and the method further comprises:
    displaying at least a portion of the real time image blended with the recorded image aligned according to a currently determined spatial relation between the real time image and the recorded image, a weight for blending the real time image and the recorded image being a function of a degree of correlation between the real time image and the recorded image.

20. The medium of claim 17 wherein the medical device is a needle catheter, and wherein the recorded image comprises guide information and is an ultrasonic image of the patient's coronary anatomy indicating a spatial record of sites treated by the needle catheter.

21. The medium of claim 17 wherein the recorded image is generated by producing 3-D echo images of the patient's heart with a TTE echo probe at different positions on the patient, and assembling the 3-D echo images to provide a recorded ultrasonic image of the patient's heart.

22. The medium of claim 21, the method including processing the 3-D echo images to indicate on the recorded ultrasonic image of the patient's heart a degree of heart wall motion and/or wall thickness for various locations of the heart wall.

23. The medium of claim 22 wherein the medical device comprises a needle catheter having an echogenic spherical distal tip, and wherein the obtaining of the real time image comprises ultrasonic imaging at least the spherical distal tip of the needle catheter using the TTE echo probe.

24. The medium of claim 23 wherein the spherical distal tip of the needle catheter comprises an electrode, and wherein the method further includes positioning the spherical distal tip at a desired location against a wall of the patient's heart to generate an ECG, and performing a diagnosis of tissue forming the heart wall at the desired location based on at least one of the ECG amplitude at the desired location and the degree of heart wall motion and/or wall thickness at the desired location on the recorded ultrasonic image.

25. The medium of claim 24 wherein the method further includes after performing the diagnosis of the tissue forming the heart wall at the desired location, treating the desired location by slidably advancing a needle from the spherical distal tip of the needle catheter and injecting the tissue with an agent delivered from the needle to thereby produce a treatment location, and including recording the treatment location on the first recorded image.

26. The medium of claim 25 wherein the method further includes guiding the production of one or more additional treatment locations by comparing a diagnosis of the one or more additional treatment locations with a diagnosis of previous treatment locations indicated on the first recorded image.

27. The medium of claim 17 wherein the medical device comprises a needle catheter having a shaft with a distal section which has a plurality of rotational orientation echogenic portions, and wherein the obtaining of the real time images comprises ultrasonic imaging at least the distal section of the needle catheter shaft positioned within a coronary blood vessel of the patient.

28. The medium of claim 27 wherein the method further includes adjusting the rotational orientation of the distal section of the needle catheter within the blood vessel, slidably advancing a needle from the distal section of the needle catheter, and injecting tissue of the patient's heart with an agent delivered from the needle to thereby produce a treatment location, and including recording the treatment location.

* * * * *